United States Patent
Bennett et al.

(10) Patent No.: US 10,883,103 B2
(45) Date of Patent: Jan. 5, 2021

(54) COMPOSITIONS AND METHODS FOR DELIVERY OF A POLYNUCLEOTIDE INTO A PLANT

(71) Applicant: MONSANTO TECHNOLOGY LLC, St. Louis, MO (US)

(72) Inventors: Michael J. Bennett, San Francisco, CA (US); Shihshieh Huang, Woodland, CA (US); Alberto B. Iandolino, Davis, CA (US); Heather A. Lindfors, Winters, CA (US); Janette V. Oakes, Davis, CA (US); Gregory John Peel, Davis, CA (US); Sharon E. Radke, Davis, CA (US); Steven H. Schwartz, Davis, CA (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

(21) Appl. No.: 15/579,125

(22) PCT Filed: Jun. 2, 2016

(86) PCT No.: PCT/US2016/035435
§ 371 (c)(1),
(2) Date: Dec. 1, 2017

(87) PCT Pub. No.: WO2016/196738
PCT Pub. Date: Dec. 8, 2016

(65) Prior Publication Data
US 2018/0163203 A1 Jun. 14, 2018

Related U.S. Application Data

(60) Provisional application No. 62/170,002, filed on Jun. 2, 2015, provisional application No. 62/170,447, filed on Jun. 3, 2015.

(51) Int. Cl.
| | | |
|---|---|---|
| C12N 15/87 | (2006.01) | |
| C12N 15/113 | (2010.01) | |
| C12N 15/82 | (2006.01) | |
| C12N 9/22 | (2006.01) | |

(52) U.S. Cl.
CPC .............. *C12N 15/113* (2013.01); *C12N 9/22* (2013.01); *C12N 15/8206* (2013.01); *C12N 15/8207* (2013.01); *C12N 15/8218* (2013.01); *C12N 15/87* (2013.01); *C12N 2310/20* (2017.05)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,469,863 A | 9/1984 | Ts'o et al. |
| 4,476,301 A | 10/1984 | Imbach et al. |
| 4,535,060 A | 8/1985 | Comai |
| 4,581,847 A | 4/1986 | Hibberd et al. |
| 4,666,828 A | 5/1987 | Gusella |
| 4,683,202 A | 7/1987 | Mullis |
| 4,761,373 A | 8/1988 | Anderson et al. |
| 4,769,061 A | 9/1988 | Comai |
| 4,801,531 A | 1/1989 | Frossard |
| 4,810,648 A | 3/1989 | Stalker |
| 4,879,219 A | 11/1989 | Wands et al. |
| 4,940,835 A | 7/1990 | Shah et al. |
| 4,971,908 A | 11/1990 | Kishore et al. |
| 5,004,863 A | 4/1991 | Umbeck |
| 5,011,771 A | 4/1991 | Bellet et al. |
| 5,013,659 A | 5/1991 | Bedbrook et al. |
| 5,015,580 A | 5/1991 | Christou et al. |
| 5,023,243 A | 6/1991 | Tullis |
| 5,034,506 A | 7/1991 | Summerton et al. |
| 5,094,945 A | 3/1992 | Comai |
| 5,141,870 A | 8/1992 | Bedbrook et al. |
| 5,145,783 A | 9/1992 | Kishore et al. |
| 5,159,135 A | 10/1992 | Umbeck |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,642 A | 2/1993 | Shah et al. |

(Continued)

FOREIGN PATENT DOCUMENTS

| | | |
|---|---|---|
| AU | 2008258254 B2 | 7/2014 |
| AU | 2014262189 B2 | 11/2014 |

(Continued)

OTHER PUBLICATIONS

Tenllado et al. (BMC biotechnology 3.1 (2003): 3) (Year: 2003).*

(Continued)

*Primary Examiner* — Charles Logsdon
(74) *Attorney, Agent, or Firm* — Arnold & Porter Kaye Scholer LLP; Amanda Carmany-Rampey; David R. Marsh

(57) ABSTRACT

The present disclosure provides compositions and methods for delivering a polynucleotide from the exterior surface of a plant or plant part into the interior of a plant cell. More specifically, the present disclosure relates to compositions comprising at least one polynucleotide and at least one agent that is able to disrupt at least one barrier of the plant or plant part.

8 Claims, 2 Drawing Sheets

(56) References Cited

U.S. PATENT DOCUMENTS

| | | |
|---|---|---|
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. |
| 5,276,019 A | 1/1994 | Cohen et al. |
| 5,281,521 A | 1/1994 | Trojanowski et al. |
| 5,286,634 A | 2/1994 | Stadler et al. |
| 5,286,717 A | 2/1994 | Cohen et al. |
| 5,304,732 A | 4/1994 | Anderson et al. |
| 5,310,667 A | 5/1994 | Eichholtz et al. |
| 5,312,910 A | 5/1994 | Kishore et al. |
| 5,321,131 A | 6/1994 | Agrawal et al. |
| 5,331,107 A | 7/1994 | Anderson et al. |
| 5,339,107 A | 8/1994 | Henry et al. |
| 5,346,107 A | 9/1994 | Bouix et al. |
| 5,378,824 A | 1/1995 | Bedbrook et al. |
| 5,384,253 A | 1/1995 | Krzyzek et al. |
| 5,390,667 A | 2/1995 | Kumakura et al. |
| 5,392,910 A | 2/1995 | Bell et al. |
| 5,393,175 A | 2/1995 | Courville |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,459,127 A | 10/1995 | Felgner et al. |
| 5,460,667 A | 10/1995 | Moriyuki et al. |
| 5,462,910 A | 10/1995 | Ito et al. |
| 5,463,174 A | 10/1995 | Moloney et al. |
| 5,463,175 A | 10/1995 | Barry et al. |
| 5,466,677 A | 11/1995 | Baxter et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,518,908 A | 5/1996 | Corbin et al. |
| 5,519,126 A | 5/1996 | Hecht |
| 5,536,821 A | 7/1996 | Agrawal et al. |
| 5,538,880 A | 7/1996 | Lundquist et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,550,398 A | 8/1996 | Kocian et al. |
| 5,550,468 A | 8/1996 | Häberlein et al. |
| 5,558,071 A | 9/1996 | Ward et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,597,717 A | 1/1997 | Guerineau et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,719,046 A | 2/1998 | Guerineau et al. |
| 5,721,138 A | 2/1998 | Lawn |
| 5,731,180 A | 3/1998 | Dietrich |
| 5,739,180 A | 4/1998 | Taylor-Smith |
| 5,746,180 A | 5/1998 | Jefferson et al. |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,837,848 A | 11/1998 | Ely et al. |
| 5,859,347 A | 1/1999 | Brown et al. |
| 5,866,775 A | 2/1999 | Eichholtz et al. |
| 5,874,265 A | 2/1999 | Adams et al. |
| 5,879,903 A | 3/1999 | Strauch et al. |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,089 A | 7/2000 | Mine et al. |
| 6,084,155 A | 7/2000 | Volrath et al. |
| 6,118,047 A | 9/2000 | Anderson et al. |
| 6,121,513 A | 9/2000 | Zhang et al. |
| 6,130,366 A | 10/2000 | Herrera-Estrella et al. |
| 6,140,078 A | 10/2000 | Sanders et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,194,636 B1 | 2/2001 | McElroy et al. |
| 6,225,105 B1 | 5/2001 | Sathasivan et al. |
| 6,225,114 B1 | 5/2001 | Eichholtz et al. |
| 6,232,526 B1 | 5/2001 | McElroy et al. |
| 6,245,968 B1 | 6/2001 | Boudec et al. |
| 6,248,876 B1 | 6/2001 | Barry et al. |
| 6,252,138 B1 | 6/2001 | Karimi et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,426,446 B1 | 7/2002 | McElroy et al. |
| 6,433,252 B1 | 8/2002 | Kriz et al. |
| 6,437,217 B1 | 8/2002 | McElroy et al. |
| 6,453,609 B1 | 9/2002 | Soll et al. |
| 6,479,291 B2 | 11/2002 | Kumagai et al. |
| 6,506,559 B1 | 1/2003 | Fire et al. |
| 6,506,599 B1 | 1/2003 | Yoon |
| 6,642,435 B1 | 11/2003 | Rafalski et al. |
| 6,644,341 B1 | 11/2003 | Chemo et al. |
| 6,645,914 B1 | 11/2003 | Woznica et al. |
| 6,768,044 B1 | 7/2004 | Boudec et al. |
| 6,992,237 B1 | 1/2006 | Habben et al. |
| 7,022,896 B1 | 4/2006 | Weeks et al. |
| 7,026,528 B2 | 4/2006 | Cheng et al. |

(56) References Cited

U.S. PATENT DOCUMENTS

| | | |
|---|---|---|
| RE39,247 E | 8/2006 | Barry et al. |
| 7,105,724 B2 | 9/2006 | Weeks et al. |
| 7,119,256 B2 | 10/2006 | Shimizu et al. |
| 7,138,564 B2 | 11/2006 | Tian et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,392,379 B2 | 6/2008 | Le Pennec et al. |
| 7,405,347 B2 | 7/2008 | Hammer et al. |
| 7,406,981 B2 | 8/2008 | Hemo et al. |
| 7,462,379 B2 | 12/2008 | Fukuda et al. |
| 7,485,777 B2 | 2/2009 | Nakajima et al. |
| 7,525,013 B2 | 4/2009 | Hildebrand et al. |
| 7,550,578 B2 | 6/2009 | Budworth et al. |
| 7,622,301 B2 | 11/2009 | Ren et al. |
| 7,657,299 B2 | 2/2010 | Huizenga et al. |
| 7,671,254 B2 | 3/2010 | Tranel et al. |
| 7,714,188 B2 | 5/2010 | Castle et al. |
| 7,738,626 B2 | 6/2010 | Weese et al. |
| 7,807,791 B2 | 10/2010 | Sekar et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,090,164 B2 | 1/2012 | Bullitt et al. |
| 8,143,480 B2 | 3/2012 | Axtell et al. |
| 8,226,938 B1 | 7/2012 | Meikle et al. |
| 8,548,778 B1 | 10/2013 | Hart et al. |
| 8,554,490 B2 | 10/2013 | Tang et al. |
| 9,121,022 B2 | 9/2015 | Sammons et al. |
| 9,422,557 B2 | 8/2016 | Ader |
| 9,445,603 B2 | 9/2016 | Baum et al. |
| 9,777,288 B2 | 10/2017 | Beattie et al. |
| 9,850,496 B2 | 12/2017 | Beattie et al. |
| 9,856,495 B2 | 1/2018 | Beattie et al. |
| 2001/0006797 A1 | 7/2001 | Kumagai et al. |
| 2001/0042257 A1 | 11/2001 | Connor-Ward et al. |
| 2002/0069430 A1 | 6/2002 | Kiaska et al. |
| 2002/0106653 A1 | 8/2002 | Kurane et al. |
| 2002/0114784 A1 | 8/2002 | Li et al. |
| 2003/0150017 A1 | 8/2003 | Mesa et al. |
| 2003/0154508 A1 | 8/2003 | Stevens et al. |
| 2003/0167537 A1 | 9/2003 | Jiang |
| 2003/0221211 A1 | 11/2003 | Rottmann et al. |
| 2004/0029275 A1 | 2/2004 | Brown et al. |
| 2004/0053289 A1 | 3/2004 | Allen et al. |
| 2004/0055041 A1 | 3/2004 | Labate et al. |
| 2004/0072692 A1 | 4/2004 | Hoffman et al. |
| 2004/0082475 A1 | 4/2004 | Hoffman et al. |
| 2004/0123347 A1 | 6/2004 | Hinchey et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0216189 A1 | 10/2004 | Houmard et al. |
| 2004/0244075 A1 | 12/2004 | Cai et al. |
| 2004/0250310 A1 | 12/2004 | Shukla et al. |
| 2005/0005319 A1 | 1/2005 | della-Cioppa et al. |
| 2005/0044591 A1 | 2/2005 | Yao et al. |
| 2005/0215435 A1 | 9/2005 | Menges et al. |
| 2005/0223425 A1 | 10/2005 | Clinton et al. |
| 2005/0246784 A1 | 11/2005 | Plesch et al. |
| 2005/0250647 A1 | 11/2005 | Hills et al. |
| 2005/0289664 A1 | 12/2005 | Moshiri et al. |
| 2006/0009358 A1 | 1/2006 | Kibler et al. |
| 2006/0021087 A1 | 1/2006 | Baum et al. |
| 2006/0040826 A1 | 2/2006 | Eaton et al. |
| 2006/0111241 A1 | 5/2006 | Gerwick, III et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0223708 A1 | 10/2006 | Hoffman et al. |
| 2006/0223709 A1 | 10/2006 | Helmke et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011775 A1 | 1/2007 | Allen et al. |
| 2007/0021360 A1 | 1/2007 | Nyce et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0250947 A1 | 10/2007 | Boukharov et al. |
| 2007/0259785 A1 | 11/2007 | Heck et al. |
| 2007/0269815 A1 | 11/2007 | Rivory et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0113351 A1 | 5/2008 | Naito et al. |
| 2008/0155716 A1 | 6/2008 | Sonnewald et al. |
| 2008/0214443 A1 | 9/2008 | Baum et al. |
| 2009/0011934 A1 | 1/2009 | Zawierucha et al. |
| 2009/0018016 A1 | 1/2009 | Duck et al. |
| 2009/0036311 A1 | 2/2009 | Witschel et al. |
| 2009/0054240 A1 | 2/2009 | Witschel et al. |
| 2009/0075921 A1 | 3/2009 | Ikegawa et al. |
| 2009/0094717 A1 | 4/2009 | Troukhan et al. |
| 2009/0098614 A1 | 4/2009 | Zamore et al. |
| 2009/0118214 A1 | 5/2009 | Paldi et al. |
| 2009/0137395 A1 | 5/2009 | Chicoine et al. |
| 2009/0144848 A1 | 6/2009 | Kovalic et al. |
| 2009/0165153 A1 | 6/2009 | Wang et al. |
| 2009/0165166 A1 | 6/2009 | Feng et al. |
| 2009/0172838 A1 | 7/2009 | Axtell et al. |
| 2009/0188005 A1 | 7/2009 | Boukharov et al. |
| 2009/0205079 A1 | 8/2009 | Kumar et al. |
| 2009/0215628 A1 | 8/2009 | Witschel et al. |
| 2009/0285784 A1 | 11/2009 | Raemaekers et al. |
| 2009/0293148 A1 | 11/2009 | Ren et al. |
| 2009/0298787 A1 | 12/2009 | Raemaekers et al. |
| 2009/0306189 A1 | 12/2009 | Raemaekers et al. |
| 2009/0307803 A1 | 12/2009 | Baum et al. |
| 2010/0005551 A1 | 1/2010 | Roberts et al. |
| 2010/0048670 A1 | 2/2010 | Biard et al. |
| 2010/0068172 A1 | 3/2010 | Van De Craen |
| 2010/0071088 A1 | 3/2010 | Sela et al. |
| 2010/0099561 A1 | 4/2010 | Selby et al. |
| 2010/0100988 A1 | 4/2010 | Tranel et al. |
| 2010/0152443 A1 | 6/2010 | Hirai et al. |
| 2010/0154083 A1 | 6/2010 | Ross et al. |
| 2010/0192237 A1 | 7/2010 | Ren et al. |
| 2010/0247578 A1 | 9/2010 | Salama |
| 2010/0248373 A1 | 9/2010 | Baba et al. |
| 2011/0015084 A1 | 1/2011 | Christian et al. |
| 2011/0015284 A1 | 1/2011 | Dees et al. |
| 2011/0028412 A1 | 2/2011 | Cappello et al. |
| 2011/0035836 A1 | 2/2011 | Eudes et al. |
| 2011/0041400 A1 | 2/2011 | Trias Vila et al. |
| 2011/0053226 A1 | 3/2011 | Rohayem |
| 2011/0098180 A1 | 4/2011 | Michel et al. |
| 2011/0105327 A1 | 5/2011 | Nelson |
| 2011/0105329 A1 | 5/2011 | Song et al. |
| 2011/0112570 A1 | 5/2011 | Mannava et al. |
| 2011/0126310 A1 | 5/2011 | Feng et al. |
| 2011/0126311 A1 | 5/2011 | Velcheva et al. |
| 2011/0152339 A1 | 6/2011 | Brown et al. |
| 2011/0152346 A1 | 6/2011 | Karleson et al. |
| 2011/0152353 A1 | 6/2011 | Koizumi et al. |
| 2011/0160082 A1 | 6/2011 | Woo et al. |
| 2011/0166022 A1 | 7/2011 | Israels et al. |
| 2011/0166023 A1 | 7/2011 | Nettleton-Hammond et al. |
| 2011/0171176 A1 | 7/2011 | Baas et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |
| 2011/0191897 A1 | 8/2011 | Poree et al. |

(56) References Cited

U.S. PATENT DOCUMENTS

| | | | |
|---|---|---|---|
| 2011/0201501 A1 | 8/2011 | Song et al. | |
| 2011/0203013 A1 | 8/2011 | Peterson et al. | |
| 2011/0296555 A1 | 12/2011 | Ivashuta et al. | |
| 2011/0296556 A1* | 12/2011 | Sammons | A01N 63/02 800/298 |
| 2012/0036594 A1 | 2/2012 | Cardoza et al. | |
| 2012/0107355 A1 | 5/2012 | Harris et al. | |
| 2012/0108497 A1 | 5/2012 | Paldi et al. | |
| 2012/0137387 A1 | 5/2012 | Baum et al. | |
| 2012/0150048 A1 | 6/2012 | Kang et al. | |
| 2012/0156784 A1 | 6/2012 | Adams, Jr. et al. | |
| 2012/0157512 A1 | 6/2012 | Ben-Chanoch et al. | |
| 2012/0164205 A1 | 6/2012 | Baum et al. | |
| 2012/0174262 A1 | 7/2012 | Azhakanandam et al. | |
| 2012/0185967 A1 | 7/2012 | Sela et al. | |
| 2012/0198586 A1 | 8/2012 | Narva et al. | |
| 2012/0230565 A1 | 9/2012 | Steinberg et al. | |
| 2012/0258646 A1 | 10/2012 | Sela et al. | |
| 2013/0003213 A1 | 1/2013 | Kabelac et al. | |
| 2013/0041004 A1 | 2/2013 | Drager et al. | |
| 2013/0047297 A1 | 2/2013 | Sammons et al. | |
| 2013/0047298 A1 | 2/2013 | Tang | |
| 2013/0060133 A1 | 3/2013 | Kassab et al. | |
| 2013/0067618 A1 | 3/2013 | Ader et al. | |
| 2013/0084243 A1 | 4/2013 | Goetsch et al. | |
| 2013/0096073 A1 | 4/2013 | Sidelman | |
| 2013/0097726 A1 | 4/2013 | Ader et al. | |
| 2013/0212739 A1 | 8/2013 | Giritch et al. | |
| 2013/0226003 A1 | 8/2013 | Edic et al. | |
| 2013/0247247 A1 | 9/2013 | Ader et al. | |
| 2013/0254940 A1 | 9/2013 | Ader et al. | |
| 2013/0254941 A1 | 9/2013 | Ader et al. | |
| 2013/0288895 A1 | 10/2013 | Ader et al. | |
| 2013/0318657 A1 | 11/2013 | Avniel et al. | |
| 2013/0318658 A1 | 11/2013 | Ader et al. | |
| 2013/0324842 A1 | 12/2013 | Mittal et al. | |
| 2013/0326731 A1 | 12/2013 | Ader et al. | |
| 2014/0018241 A1 | 1/2014 | Sammons et al. | |
| 2014/0057789 A1 | 2/2014 | Sammons et al. | |
| 2014/0109258 A1 | 4/2014 | Van De Craen et al. | |
| 2014/0230090 A1 | 8/2014 | Avniel et al. | |
| 2014/0274712 A1 | 9/2014 | Finnessy et al. | |
| 2014/0275208 A1 | 9/2014 | Hu et al. | |
| 2014/0296503 A1 | 10/2014 | Avniel et al. | |
| 2015/0096079 A1 | 4/2015 | Avniel et al. | |
| 2015/0143580 A1 | 5/2015 | Beattie et al. | |
| 2015/0159156 A1 | 6/2015 | Inberg et al. | |
| 2015/0203867 A1 | 7/2015 | Beattie et al. | |
| 2015/0240258 A1 | 8/2015 | Beattie et al. | |
| 2016/0015035 A1 | 1/2016 | Tao | |
| 2016/0029644 A1 | 2/2016 | Tao | |
| 2017/0114351 A1* | 4/2017 | Mahfouz | C12N 9/22 |

FOREIGN PATENT DOCUMENTS

| | | |
|---|---|---|
| CN | 101279950 A | 10/2008 |
| CN | 101279951 A | 10/2008 |
| CN | 101892247 A | 11/2010 |
| CN | 101914540 A | 12/2010 |
| CN | 102154364 A | 8/2011 |
| CN | 102481311 A | 5/2012 |
| CN | 102822350 A | 12/2012 |
| CN | 102906263 A | 1/2013 |
| DE | 288618 A5 | 4/1991 |
| DE | 10000600 A1 | 7/2001 |
| DE | 10116399 A1 | 10/2002 |
| DE | 10256353 A1 | 6/2003 |
| DE | 10256354 A1 | 6/2003 |
| DE | 10256367 A1 | 6/2003 |
| DE | 10204951 A1 | 8/2003 |
| DE | 10234875 A1 | 2/2004 |
| DE | 10234876 A1 | 2/2004 |
| DE | 102004054666 A1 | 5/2006 |
| DE | 102005014638 A1 | 10/2006 |
| DE | 102005014906 A1 | 10/2006 |
| DE | 102007012168 A1 | 9/2008 |
| DE | 102010042866 A1 | 5/2011 |
| EP | 0 804 600 A1 | 11/1997 |
| EP | 1 155 615 A1 | 11/2001 |
| EP | 1 157 991 A2 | 11/2001 |
| EP | 1 238 586 A1 | 9/2002 |
| EP | 1 416 049 A1 | 5/2004 |
| EP | 1 496 123 A1 | 1/2005 |
| EP | 1 889 902 A1 | 2/2008 |
| EP | 1 964 919 A1 | 9/2008 |
| EP | 2 147 919 A1 | 1/2010 |
| EP | 2 160 098 B1 | 11/2010 |
| EP | 2 530 159 A1 | 3/2011 |
| EP | 2 305 813 A2 | 4/2011 |
| EP | 2 473 024 A2 | 7/2012 |
| EP | 2 545 182 A1 | 1/2013 |
| JE | 2001-253874 A | 9/2001 |
| JP | 2001253874 A | 9/2001 |
| JP | 2002-080454 A | 3/2002 |
| JP | 2002080454 A | 3/2002 |
| JP | 2002-138075 A | 5/2002 |
| JP | 2002-145707 A | 5/2002 |
| JP | 2002138075 A | 5/2002 |
| JP | 2002145707 A | 5/2002 |
| JP | 2002-220389 A | 8/2002 |
| JP | 2002220389 A | 8/2002 |
| JP | 2003-064059 A | 3/2003 |
| JP | 2003064059 A | 3/2003 |
| JP | 2003-096059 A | 4/2003 |
| JP | 2003096059 A | 4/2003 |
| JP | 2004-051628 A | 2/2004 |
| JP | 2004051628 A | 2/2004 |
| JP | 2004-107228 A | 4/2004 |
| JP | 2004107228 A | 4/2004 |
| JP | 2005-008583 A | 1/2005 |
| JP | 2005008583 A | 1/2005 |
| JP | 2005-239675 A | 9/2005 |
| JP | 2005239675 A | 9/2005 |
| JP | 2005-314407 A | 11/2005 |
| JP | 2005314407 A | 11/2005 |
| JP | 2006-232824 A | 9/2006 |
| JP | 2006232824 A | 9/2006 |
| JP | 2006-282552 A | 10/2006 |
| JP | 2006282552 A | 10/2006 |
| JP | 2007-153847 A | 6/2007 |
| JP | 2007-161701 A | 6/2007 |
| JP | 2007153847 A | 6/2007 |
| JP | 2007161701 A | 6/2007 |
| JP | 2007-182404 A | 7/2007 |
| JP | 2007182404 A | 7/2007 |
| JP | 2008-074840 A | 4/2008 |
| JP | 2008-074841 A | 4/2008 |
| JP | 2008074840 A | 4/2008 |
| JP | 2008074841 A | 4/2008 |
| JP | 2008-133207 A | 6/2008 |
| JP | 2008-133218 A | 6/2008 |
| JP | 2008133207 A | 6/2008 |
| JP | 2008133218 A | 6/2008 |
| JP | 2008-169121 A | 7/2008 |
| JP | 2008169121 A | 7/2008 |
| JP | 2009-508481 A | 3/2009 |
| JP | 2009-067739 A | 4/2009 |
| JP | 2009067739 A | 4/2009 |
| JP | 2009-114128 A | 5/2009 |
| JP | 2009114128 A | 5/2009 |
| JP | 2009-126792 A | 6/2009 |
| JP | 2009-137851 A | 6/2009 |
| JP | 2009126792 A | 6/2009 |
| JP | 2009137851 A | 6/2009 |
| JP | 2016-532440 A | 10/2015 |
| RU | 2 291 613 C1 | 1/2007 |
| RU | 2 337 529 C1 | 11/2008 |
| WO | WO 89/11789 A1 | 12/1989 |
| WO | WO 95/34659 A1 | 12/1995 |
| WO | WO 95/34668 A2 | 12/1995 |
| WO | WO 96/005721 A1 | 2/1996 |
| WO | WO 96/033270 A1 | 10/1996 |
| WO | WO 96/038567 A2 | 12/1996 |

(56) References Cited

FOREIGN PATENT DOCUMENTS

| | | |
|---|---|---|
| WO | WO 96/040964 A2 | 12/1996 |
| WO | WO 97/49816 A1 | 12/1997 |
| WO | WO 99/14348 A1 | 3/1999 |
| WO | WO 99/024585 A1 | 5/1999 |
| WO | WO 99/26467 A1 | 6/1999 |
| WO | WO 99/27116 A2 | 6/1999 |
| WO | WO 99/32619 A1 | 7/1999 |
| WO | WO 99/61631 A1 | 12/1999 |
| WO | WO 99/67367 A1 | 12/1999 |
| WO | WO 00/32757 A2 | 6/2000 |
| WO | WO 00/044914 A1 | 8/2000 |
| WO | WO 01/07601 A2 | 2/2001 |
| WO | WO 2001/085970 A2 | 11/2001 |
| WO | WO 02/14472 A2 | 2/2002 |
| WO | WO 02/066660 A2 | 8/2002 |
| WO | WO 03/000679 A2 | 1/2003 |
| WO | WO 03/004649 | 1/2003 |
| WO | WO 03/006422 A1 | 1/2003 |
| WO | WO 03/012052 A2 | 2/2003 |
| WO | WO 03/013247 A1 | 2/2003 |
| WO | WO 03/016308 A1 | 2/2003 |
| WO | WO 2003/014357 A1 | 2/2003 |
| WO | WO 03/020704 A1 | 3/2003 |
| WO | WO 03/022051 A1 | 3/2003 |
| WO | WO 03/022831 A1 | 3/2003 |
| WO | WO 03/022843 A1 | 3/2003 |
| WO | WO 03/029243 A2 | 4/2003 |
| WO | WO 03/037085 A1 | 5/2003 |
| WO | WO 03/037878 A1 | 5/2003 |
| WO | WO 03/045878 A2 | 6/2003 |
| WO | WO 03/050087 A2 | 6/2003 |
| WO | WO 03/051823 A1 | 6/2003 |
| WO | WO 03/051824 A1 | 6/2003 |
| WO | WO 03/051846 A2 | 6/2003 |
| WO | WO 03/064625 A2 | 8/2003 |
| WO | WO 03/076409 A1 | 9/2003 |
| WO | WO 03/077648 A2 | 9/2003 |
| WO | WO 03/087067 A1 | 10/2003 |
| WO | WO 03/090539 A1 | 11/2003 |
| WO | WO 03/091217 A1 | 11/2003 |
| WO | WO 03/093269 A2 | 11/2003 |
| WO | WO 03/104206 A2 | 12/2003 |
| WO | WO 2004/002947 A1 | 1/2004 |
| WO | WO 2004/002981 A2 | 1/2004 |
| WO | WO 2004/005485 A2 | 1/2004 |
| WO | WO 2004/009761 A2 | 1/2004 |
| WO | WO 2004/011429 A1 | 2/2004 |
| WO | WO 2004/022771 A2 | 3/2004 |
| WO | WO 2004/029060 A1 | 4/2004 |
| WO | WO 2004/035545 A2 | 4/2004 |
| WO | WO 2004/035563 A1 | 4/2004 |
| WO | WO 2004/035564 A1 | 4/2004 |
| WO | WO 2004/037787 A1 | 5/2004 |
| WO | WO 2004/049806 A1 | 6/2004 |
| WO | WO 2004/062351 A2 | 7/2004 |
| WO | WO 2004/067518 A1 | 8/2004 |
| WO | WO 2004/067527 A1 | 8/2004 |
| WO | WO 2004/074443 A2 | 9/2004 |
| WO | WO 2004/077950 A1 | 9/2004 |
| WO | WO 2005/000824 A1 | 1/2005 |
| WO | WO 2005/003362 A2 | 1/2005 |
| WO | WO 2005/007627 A1 | 1/2005 |
| WO | WO 2005/007860 A1 | 1/2005 |
| WO | WO 2005/040152 A1 | 5/2005 |
| WO | WO 2005/047233 A1 | 5/2005 |
| WO | WO 2005/047281 A1 | 5/2005 |
| WO | WO 2005/061443 A2 | 7/2005 |
| WO | WO 2005/061464 A1 | 7/2005 |
| WO | WO 2005/068434 A1 | 7/2005 |
| WO | WO 2005/070889 A1 | 8/2005 |
| WO | WO 2005/089551 A1 | 9/2005 |
| WO | WO 2005/095335 A1 | 10/2005 |
| WO | WO 2005/107437 A2 | 11/2005 |
| WO | WO 2005/110068 A2 | 11/2005 |
| WO | WO 2006/006569 A1 | 1/2006 |
| WO | WO 2006/024820 A1 | 3/2006 |
| WO | WO 2006/029828 A1 | 3/2006 |
| WO | WO 2006/029829 A1 | 3/2006 |
| WO | WO 2006/037945 A1 | 4/2006 |
| WO | WO 2006/050803 A1 | 5/2006 |
| WO | WO 2006/074400 A2 | 7/2006 |
| WO | WO 2006/090792 A1 | 8/2006 |
| WO | WO 2006/123088 A2 | 11/2006 |
| WO | WO 2006/125687 A1 | 11/2006 |
| WO | WO 2006/125688 A1 | 11/2006 |
| WO | WO 2006/132270 A1 | 12/2006 |
| WO | WO 2006/138638 A1 | 12/2006 |
| WO | WO 2007/003294 A1 | 1/2007 |
| WO | WO 2007/007316 A1 | 1/2007 |
| WO | WO 2007/024783 | 3/2007 |
| WO | WO 2007/026834 A1 | 3/2007 |
| WO | WO 2007/035650 A2 | 3/2007 |
| WO | WO 2007/038788 A2 | 4/2007 |
| WO | WO 2007/039454 A1 | 4/2007 |
| WO | WO 2007/050715 A2 | 5/2007 |
| WO | WO 2007/051462 A2 | 5/2007 |
| WO | WO 2007/070389 A2 | 6/2007 |
| WO | WO 2007/071900 A1 | 6/2007 |
| WO | WO 2007/074405 A2 | 7/2007 |
| WO | WO 2007/077201 A1 | 7/2007 |
| WO | WO 2007/077247 A1 | 7/2007 |
| WO | WO 2007/080126 A2 | 7/2007 |
| WO | WO 2007/080127 A2 | 7/2007 |
| WO | WO 2007/083193 A2 | 7/2007 |
| WO | WO 2007/096576 A1 | 8/2007 |
| WO | WO 2007/051462 A3 | 10/2007 |
| WO | WO 2007/119434 A1 | 10/2007 |
| WO | WO 2007/134984 A1 | 11/2007 |
| WO | WO 2008/007100 A2 | 1/2008 |
| WO | WO 2008/009908 A1 | 1/2008 |
| WO | WO 2008/029084 A1 | 3/2008 |
| WO | WO 2008/042231 A2 | 4/2008 |
| WO | WO 2008/059948 A1 | 5/2008 |
| WO | WO 2008/063203 A2 | 5/2008 |
| WO | WO 2008/071918 A1 | 6/2008 |
| WO | WO 2008/074991 A1 | 6/2008 |
| WO | WO 2008/084073 A1 | 7/2008 |
| WO | WO 2008/100426 A2 | 8/2008 |
| WO | WO 2008/102908 A1 | 8/2008 |
| WO | WO 2008/148223 A1 | 12/2008 |
| WO | WO 2008/152072 A2 | 12/2008 |
| WO | WO 2008/152073 A2 | 12/2008 |
| WO | WO 2009/000757 A1 | 12/2008 |
| WO | WO 2009/005297 A2 | 1/2009 |
| WO | WO 2009/029690 A1 | 3/2009 |
| WO | WO 2009/035150 A2 | 3/2009 |
| WO | WO 2009/037329 A2 | 3/2009 |
| WO | WO 2009/046384 A1 | 4/2009 |
| WO | WO 2009/060429 A2 | 5/2009 |
| WO | WO 2009/063180 A1 | 5/2009 |
| WO | WO 2009/068170 A2 | 6/2009 |
| WO | WO 2009/068171 A2 | 6/2009 |
| WO | WO 2009/086041 A1 | 7/2009 |
| WO | WO 2009/090401 A2 | 7/2009 |
| WO | WO 2009/090402 A2 | 7/2009 |
| WO | WO 2009/115788 A1 | 9/2009 |
| WO | WO 2009/116558 A1 | 9/2009 |
| WO | WO 2009/125401 A2 | 10/2009 |
| WO | WO 2009/144079 A1 | 12/2009 |
| WO | WO 2009/152995 A1 | 12/2009 |
| WO | WO 2009/153607 A1 | 12/2009 |
| WO | WO 2009/158258 A1 | 12/2009 |
| WO | WO 2010/012649 A1 | 2/2010 |
| WO | WO 2010/026989 A1 | 3/2010 |
| WO | WO 2010/034153 A1 | 4/2010 |
| WO | WO 2010/049270 A1 | 5/2010 |
| WO | WO 2010/049369 A1 | 5/2010 |
| WO | WO 2010/049405 A1 | 5/2010 |
| WO | WO 2010/049414 A1 | 5/2010 |
| WO | WO 2010/056519 A1 | 5/2010 |
| WO | WO 2010/063422 A1 | 6/2010 |
| WO | WO 2010/069802 A1 | 6/2010 |
| WO | WO 2010/078906 A2 | 7/2010 |
| WO | WO 2010/078912 A1 | 7/2010 |

(56) References Cited

FOREIGN PATENT DOCUMENTS

| | | |
|---|---|---|
| WO | WO 2010/093788 A2 | 8/2010 |
| WO | WO 2010/104217 A1 | 9/2010 |
| WO | WO 2010/108611 A1 | 9/2010 |
| WO | WO 2010/112826 A2 | 10/2010 |
| WO | WO 2010/116122 A2 | 10/2010 |
| WO | WO 2010/119906 A1 | 10/2010 |
| WO | WO 2010/130970 A1 | 11/2010 |
| WO | WO 2011/001434 A1 | 1/2011 |
| WO | WO 2011/003776 A2 | 1/2011 |
| WO | WO 2011/028836 A2 | 3/2011 |
| WO | WO 2011/035874 A1 | 3/2011 |
| WO | WO 2011/045796 A1 | 4/2011 |
| WO | WO 2011/065451 A1 | 6/2011 |
| WO | WO 2011/067745 A2 | 6/2011 |
| WO | WO 2011/075188 A1 | 6/2011 |
| WO | WO 2011/080674 A2 | 7/2011 |
| WO | WO 2011/112570 A1 | 9/2011 |
| WO | WO 2011/132127 A1 | 10/2011 |
| WO | WO 2012/001626 A1 | 1/2012 |
| WO | WO 2012/056401 A1 | 5/2012 |
| WO | WO 2012/092580 A2 | 7/2012 |
| WO | WO 2012/156342 A1 | 11/2012 |
| WO | WO 2012/164100 A2 | 12/2012 |
| WO | WO 2013/010691 A1 | 1/2013 |
| WO | WO 2013/025670 A1 | 2/2013 |
| WO | WO 2013/039990 A1 | 3/2013 |
| WO | WO 2013/040005 A1 | 3/2013 |
| WO | WO 2013/040021 A1 | 3/2013 |
| WO | WO 2013/040033 A1 | 3/2013 |
| WO | WO 2013/040049 A1 | 3/2013 |
| WO | WO 2013/040057 A1 | 3/2013 |
| WO | WO 2013/040116 A9 | 3/2013 |
| WO | WO 2013/040117 A9 | 3/2013 |
| WO | WO 2013/098244 A1 | 7/2013 |
| WO | WO 2013/141680 A1 | 9/2013 |
| WO | WO 2013/142578 A1 | 9/2013 |
| WO | WO 2013/153553 A2 | 10/2013 |
| WO | WO 2013/175480 A1 | 11/2013 |
| WO | WO 2013/176772 A1 | 11/2013 |
| WO | WO 2014/022739 A2 | 2/2014 |
| WO | WO 2014/062775 A2 | 4/2014 |
| WO | WO 2014/093622 A2 | 6/2014 |
| WO | WO 2014/106837 A2 | 7/2014 |
| WO | WO 2014/106838 A2 | 7/2014 |
| WO | WO 2014/151255 A1 | 9/2014 |
| WO | WO 2014/164761 A1 | 10/2014 |
| WO | WO 2014/164797 A2 | 10/2014 |
| WO | WO 2015/010026 A2 | 1/2015 |
| WO | WO 2015/200539 A1 | 12/2015 |

OTHER PUBLICATIONS

Subramoni, S., Z. R. Suárez-Moreno, and V. Venturi. "Lipases as pathogenicity factors of plant pathogens." Handbook of hydrocarbon and lipid microbiology (2010): 3269-3277. (Year: 2010).*
Walton (Plant Physiol. (1994) 104: 1113-1118). (Year: 1994).*
Gao et al., "DNA-guided genome editing using the *Natronobacterium gregoryi* Argonaute," Nature Biotechnology, 34(7):768-773 (2016).
Hsu et al., "DNA targeting specificity of RNA-guided Cas9 nucleases," Nature Biotechnology, 31:827-832 (2013).
International Search Report dated Oct. 6, 2016, in International Patent Application No. PCT/US2016/035435.
Kaya et al., "A bacterial Argonaute with noncanonical guide RNA specificity," Proc. Natl. Acad. Sci., 113(5):4037-4062 (2016).
Liu et al., "DNAzyme-mediated recovery of small recombinant RNAs from a 5S rRNA-derived chimera expressed in *Escherichia coli*," BMC Biotechnology, 10:85 (2010).
Luo et al., "Synthetic DNA delivery systems," Nature Biotechnology, 18:33-37 (2000).
Pei et al., "On the art of identifying effective and specific siRNAs," Nature Methods, 3(9):670-676 (2006).
Qi et al., "RNA processing enables predictable programming of gene expression," Nature Biotechnology, 30:1002-1007 (2012).
Reynolds et al., "Rational siRNA design for RNA interference," Nature Biotechnology, 22:326-330 (2004).
Swarts et al., "DNA-guided DNA interference by a prokaryotic Argonaute," Nature, 507(7491):258-61 (2014).
Swarts et al., "Argonaute of the archaeon *Pyrococcus furiosus* is a DNA-guided nuclease that targets cognate DNA," Nucleic Acid Res., 43(10):5120-5129 (2015).
Thompson, et al., "CLUSTAL W: improving the sensitivity of progressive multiple sequence alignment through sequence weighting, position-specific gap penalties and weight matrix choice," Nucleic Acids Res., 22:4673-4680 (1994).
Townsend et al., "High frequency modification of plant genes using engineered zinc finger nucleases," Nature, 459:442-446 (2009).
Yin et al., "Production of double-stranded RNA for interference with TMV infection utilizing a bacterial prokaryotic expression system," Appl. Microbiol. Biotechnology, 84:323-333 (2009).
Agricultural Chemical Usage 2006 Vegetables Summary, Agricultural Statistics Herewith Board, NASS, USDA, pp. 1-372 (2007).
Agrios, Plant Pathology (Second Edition), 2:466-470 (1978).
Alarcón-Reverte et al., "Resistance to ACCase-inhibiting herbicides in the weed *Lolium multiflorum*," Comm. Appl. Biol. Sci., 73(4):899-902 (2008).
Al-Kaff et al., "Plants rendered herbicide-susceptible by cauliflower mosaic virus-elicited suppression of a 35S promoter-regulated transgene," Nature Biotechnology, 18:995-999 (2000).
Amarzguioui et al., "An algorithm for selection of functional siRNA sequences," Biochemical and Biophysical Research Communications, 316:1050-1058 (2004).
Ambrus et al., "The Diverse Roles of RNA Helicases in RNAi," Cell Cycle, 8(21):3500-3505 (2009).
An et al., "Transient RNAi Induction against Endogenous Genes in *Arabidopsis* Protoplasts Using in Vitro-Prepared Double-Stranded RNA," Biosci Biotechnol Biochem, 69(2):415-418 (2005).
Andersen et al., "Delivery of siRNA from lyophilized polymeric surfaces," Biomaterials, 29:506-512 (2008).
Andersson et al., "A novel selection system for potato transformation using a mutated AHAS gene," Plant Cell Reports, 22(4):261-267 (2003).
Anonymous, "Resistant Weeds Spur Research Into New Technologies," Grains Research & Development Corporation, 2013.
Anonymous, "A handbook for high-level expression and purification of 6xHis-tagged proteins," The QiaExpressionist, (2003).
Anonymous, "Agronomy Facts 37: Adjuvants for enhancing herbicide performance," n.p., 1-8, (Jan. 26, 2000), Web, (Jan. 21, 2004).
Anonymous, "Devgen, The mini-Monsanto," KBC Securities (2006).
Anonymous, "Do Monsanto have the next big thing?," Austalian Herbicide Resistance Initiative (AHRI), (Apr. 23, 2013) Web. (Jan. 19, 2015).
Aoki et al., "In Vivo Transfer Efficiency of Antisense Oligonucleotides into the Myocardium Using HVJ-Liposome Method," Biochem Biophys Res Commun, 231:540-545 (1997).
Arpaia et al., "Production of transgenic eggplant (*Solanum melongena* L.) resistant to Colorado Potato Beetle (*Leptinotarsa decemlineata* Say)," (1997) Theor. Appl. Genet., 95:329-334 (1997).
Artymovich, "Using RNA interference to increase crop yield and decrease pest damage," MMG 445 Basic Biotech., 5(1):7-12 (2009).
Asad et al., "Silicon Carbide Whisker-mediated Plant Transformation," Properties and Applications of Silicon Carbide, pp. 345-358 (2011).
Ascencio-Ibanez et al., "DNA abrasion onto plants is an effective method for geminivirus infection and virus-induced gene silencing," Journal of Virological Methods, 142:198-203 (2007).
Axtell et al., "A Two-Hit Trigger for siRNA Biogenesis in Plants," Cell, 127:565-577 (2006).
Bachman et al., "Characterization of the spectrum of insecticidal activity of a double-stranded RNA with targeted activity against Western Corn Rootworm (*Diabrotica virgifera virgifera* LeConte)," Transgenic Res., pp. 1-16 (2013).
Baerson et al., "Glyphosate-Resistant Goosegrass. Identification of a Mutation in the Target Enzyme 5-Enolpyruvylshikimate-3-Phosphate Synthase," Plant Physiol., 129(3):1265-1275 (2002).

(56) References Cited

OTHER PUBLICATIONS

Bai et al., "Naturally Occurring Broad-Spectrum Powdery Mildew Resistance in a Central American Tomato Accession is Caused by Loss of Mlo Function," MPMI, 21(1):30-39 (2008).
Baker, "Chlorophyll Fluorescence: A Probe of Photosynthesis In Vivo," Annu. Rev. Plant Biol., 59:89-113 (2008).
Balibrea et al., "Extracellular Invertase is an Essential Component of Cytokinin-Mediated Delay of Senescence," The Plant Cell, 16(5):1276-1287 (2004).
Bannerjee et al., "Efficient production of transgenic potato (*S. tuberosum* L. ssp. *andigena*) plants via *Agrobacterium tumefaciens*-mediated transformation," Plant Sci., 170:732 738 (2006).
Bart et al., "A novel system for gene silencing using siRNAs in rice leaf and stem-derived protoplasts," Plant Methods, 2(13):1-9 (2006).
Basu et al., "Weed genomics: new tools to understand weed biology," TRENDS in Plant Science, 9(8):391-398 (2004).
Bauer et al., "The major protein import receptor of plastids is essential for chloroplast biogenesis," Nature, 403:203-207 (2000).
Baulcombe, "RNA silencing in plants," Nature, 431:356-363 (2004).
Baulcombe, "RNA silencing and heritable epigenetic effects in tomato and *Arabidopsis*," Abstract 13th Annual Fall Symposium, Plant Genomes to Phenomes, Donald Danforth Plant Science Center, 28-30 (2011).
Baum et al., "Progress Towards RNAi-Mediated Insect Pest Management" Advances in Insect Physiology, 47:249-295 (2014).
Bayer et al., "Programmable ligand-controlled riboregulators of eukaryotic gene expression," Nature Biotechnol., 23(3):337-343 (2005).
Beal, et al., "Second Structural Motif for Recognition of DNA by Oligonucleotide-Directed Triple-Helix Formation," Science, 251:1360-1363 (1992).
Becker et al., "Fertile transgenic wheat from microprojectile bombardment of scutellar tissue," The Plant Journal, 5(2):299-307 (1994).
Bedell et al., "Sorghum Genome Sequencing by Methylation Filtration," PLOS Biology, 3(1):E13/104-115 (2005).
Belhadj et al., "Methyl Jasmonate Induces Defense Responses in Grapevine and Triggers Protection against Erysiphe necator," J. Agric Food Chem., 54:9119-9125 (2006).
Bhargava et al., "Long double-stranded RNA-mediated RNA interference as a tool to achieve site-specific silencing of hypothalamic neuropeptides," Brain Research Protocols, 13:115-125 (2004).
Boletta et al., "High Efficient Non-Viral Gene Delivery to the Rat Kidney by Novel Polycationic Vectors," J. Am Soc. Nephrol., 7:1728 (1996).
Bolognesi et al., "Characterizing the Mechanism of Action of Double-Stranded RNA Activity against Western Corn Rootworm(*Diabrotica virgifera virgifera* LeConte)," PLoS ONE 7(10):e47534 (2012).
Bolter et al., "A chloroplastic inner envelope membrane protease is essential for plant development," FEBS Letters, 580:789-794 (2006).
Bourgeois et al., "Field and producer survey of ACCase resistant wild oat in Manitoba," Canadian Journal of Plant Science, 709-715 (1997).
Breaker et al., "A DNA enzyme with Mg2+-dependent RNA phosphoesterase activity," Chemistry and Biology, 2:655-660 (1995).
Brodersen et al., "The diversity of RNA silencing pathways in plants," Trends in Genetics, 22(5):268-280 (2006).
Brugière et al., "Glutamine Synthetase in the Phloem Plays a Major Role in Controlling Proline Production," The Plant Cell, 11:1995-2011 (1999).
Burgos et al., "Review: Confirmation of Resistance to Herbicides and Evaluation of Resistance Levels," Weed Science, 61 (1):4-20 (2013).
Burleigh, "Relative quantitative RT-PCR to study the expression of plant nutrient transporters in arbuscular mycorrhizas," Plant Science, 160:899-904 (2001).
Busch et al., "RNAi for discovery of novel crop protection products," Pflanzenschutz-Nachrichten Bayer, 58(1):34-50 (2005).
Busi et al., "Gene flow increases the initial frequency of herbicide resistance alleles in unselectedpopulations," Agriculture, Ecosystems and Environments, Elsevier, Amsterdam, NL, 142(3):403-409 (2011).
Butler et al., "Priming and re-drying improve the survival of mature seeds of Digitalis purpurea during storage," Annals of Botany, 103:1261-1270 (2009).
Bytebier et al., "T-DNA organization in tumor cultures and transgenic plants of the monocotyledon Asparagus officinalis," Proc. Natl. Acad. Sci. U.S.A., 84:5345-5349 (1987).
Campbell et al., "Gene-knockdown in the honey bee mite *Varroa destructor* by a non-invasive approach: studies on a glutathione S-transferase," Parasites & Vectors, 3(1):73, pp. 1-10 (2010).
Chabannes et al., "In situ analysis of lignins in transgenic tobacco reveals a differential impact of individual transformations on the spatial patterns of lignin deposition at the cellular and subcellular levels," The Plant Journal, 28(3):271-282 (2001).
Chabbouh et al., "Cucumber mosaic virus in artichoke," FAO Plant Protection Bulletin, 38:52-53 (1990).
Chakravarty et al., "Genetic Transformation in Potato: Approaches and Strategies," Amer J Potato Res, 84:301 311 (2007).
Chang et al., "Dual-target gene silencing by using long, sythetic siRNA duplexes without triggering antiviral responses," Molecules and Cells, 27(6) 689-695 (2009).
Chang et al., "Cellular Internalization of Fluorescent Proteins via Arginine-rich Intracellular Delivery Peptide in Plant Cells," Plant Cell Physiol., 46(3):482-488 (2005).
Chee et al., "Transformation of Soybean (*Glycine max*) by Infecting Germinating Seeds with Agrobacterium tumefaciens," Plant Physiol., 91:1212-1218 (1989).
Chen et al., "Exploring MicroRNA-Like Small RNAs in the Filamentous Fungus *Fusarium oxysporum*," PLOS One, 9(8):e104956:1-10 (2014).
Chen et al., "In Vivo Analysis of the Role of atTic20 in Protein Import into Chloroplasts," The Plant Cell, 14:641-654 (2002).
Chen et al., "Transfection and Expression of Plasmid DNA in Plant Cells by an Arginine-Rich Intracellular Delivery Peptide without Protoplast Preparation," FEBS Letters 581, pp. 1891-1897 (2007).
Cheng et al., "Transient Expression of Minimum Linear Gene Cassettes in Onion Epidermal Cells Via Direct Transformation," Appl Biochem Biotechnol, 159:739-749 (2009).
Cheng et al., "Production of fertile transgenic peanut (*Arachis hypogaea* L.) plants using Agrobacterium tumefaciens," Plant Cell Reports, 15:653-657 (1996).
Chi et al., "The Function of RH22, a DEAD RNA Helicase, in the Biogenesis of the 50S Ribosomal Subunits of *Arabidopsis* Chloroplasts," Plant Physiology, 158:693-707 (2012).
Christiaens et al., "The challenge of RNAi-mediated control of hemipterans," Current Opinion in Insect Science, 6:15-21 (2014).
Chupp et al., "Chapter 8: White Rust," Vegetable Diseases and Their Control, The Ronald Press Company, New York, pp. 267-269 (1960).
Clough et al., "Floral dip: a simplified method for Agrobacterium-mediated transformation of *Arabidopsis thaliana*," The Plant Journal, 16(6):735-743.
CN101914540 Patent Diclosure, "Introduction of RNA into plant by interference," (2010).
Colbourne et al., "The Ecoresponsive Genome of Daphnia Pulex," Science, 331(6017):555-561 (2011).
Colliver et al., "Differential modification of flavonoid and isoflavonoid biosynthesis with an antisense chalcone synthase construct in transgenic Lotus corniculatus," Plant Molecular Biology, 35:509-522 (1997).
Communication pursuant to Article 94(3) EPC dated Jan. 14, 2016, in European Patent Application No. 12 832 415.9.
Communication pursuant to Article 94(3) EPC dated Jun. 26, 2015, in European Patent Application No. 11 753 916.3.
Communication pursuant to Article 94(3) EPC dated Mar. 18, 2016, in European Patent Application No. 12 832 160.1.
Communication pursuant to Article 94(3) EPC dated Mar. 24, 2016, in European Patent Application No. 12 831 684.1.
Communication pursuant to Article 94(3) EPC dated Mar. 4, 2016, in European Patent Application No. 12 830 932.5.

(56) References Cited

OTHER PUBLICATIONS

Communication pursuant to Article 94(3) EPC dated Mar. 9, 2016, in European Patent Application No. 12 831 166.9.
Communication pursuant to Article 94(3) EPC dated Oct. 23, 2015, in European Patent Application No. 12 831 945.6.
Communication pursuant to Article 94(3) EPC dated Sep. 5, 2018, in European Patent Application No. 17152830.0.
Concise Descriptions of Relevance filed by a third party on Nov. 29, 2012, in U.S. Appl. No. 13/042,856.
Constan et al., "An outer envelope membrane component of the plastid protein import apparatus plays an essential role in *Arabidopsis*," The Plant Journal, 38:93-106 (2004).
Cooney et al., "Site-Specific Oligonucleotide Binding Represses Transcription of the Human c-myc Gene in Vitro," Science ,241:456-459 (1988).
COST Action FA0806 progress report "Plant virus control employing RNA-based vaccines: A novel non-transgenic strategy" (2010).
Cotichhia et al., "Calmodulin modulates Akt activity in human breast cancer cell lines," Breast Cancer Res. Treat, 115:545-560 (2009).
Dalakouras et al., "Induction of Silencing in Plants by High-Pressure Spraying of In vitro-Synthesized Small RNAs," Frontiers in Plant Science, 7(1327):1-5 (2016).
Dalmay et al., "An RNA-Depenedent RNA Polymerase Gene in *Arabidopsis* is Required for Posttranscriptional Gene Silencing Mediated by a Transgene but Not by a Virus," Cell, 101:543-553 (2000).
Danka et al., "Field Test of Resistance to Acarapis woodi (Acari: Tarsonemidae) and of Colony Production by Four Stocks of Honey Bees (Hymenoptera: Apidae)" Journal of Economic Entomology, 88(3):584-591 (1995).
Database EMBL XP-002781749(BG442539) dated Mar. 20, 2001.
Davidson et al., "Engineering regulatory RNAs," TRENDS in Biotechnology, 23(3):109-112 (2005).
Dawson et al., "cDNA cloning of the complete genome of tobacco mosaic virus and production of infectious transcripts," Proc. Natl. Acad. Sci. USA, 83:1832-1836 (1986).
De Block, et al. "Engineering herbicide resistance in plants by expression of a detoxifying enzyme," EMBO J. 6(9):2513-2519 (1987).
De Framond, "MINI-Ti: A New Vector Strategy for Plant Genetic Engineering," Nature Biotechnology, 1:262-269 (1983).
Declaration of Jerzy Zabkiewicz executed Nov. 28, 2017, as filed by Opponent in Australian Patent Application No. 2014262189, pp. 1-73.
Declaration of Jerzy Zabkiewicz executed Nov. 28, 2017, as filed by Opponent in Australian Patent Application No. 2014262189, pp. 1-4.
Declaration of Neena Mitter executed Nov. 30, 2017, as filed by Opponent in Australian Patent Application No. 2014262189, pp. 1-114.
Declaration of Neena Mitter executed Nov. 30, 2017, as filed by Opponent in Australian Patent Application No. 2014262189, pp. 1-25.
Della-Cioppa et al., "Import of a precursor protein into chloroplasts is inhibited by the herbicide glyphosate," The EMBO Journal, 7(5):1299-1305 (1988).
Delye et al., "PCR-based detection of resistance to acetyl-CoA carboxylase-inhibiting herbicides in black-grass (*Alopecurus myosuroides* Huds) and ryegrass (*Lolium rigidum* Gaud)," Pest Management Science, 58:474-478 (2002).
Delye et al., "Variation in the gene encoding acetolactate-synthase in *Lolium* species and proactive detection of mutant, herbicide-resistant alleles," Weed Research, 49:326-336 (2009).
Desai et al., "Reduction in deformed wing virus infection in larval and adult honey bees (*Apis mellifera* L.) by double-stranded RNA ingestion," Insect Molecular Biology, 21(4):446-455 (2012).
Desveaux et al., "PBF-2 is a Novel Single-Stranded DNA Binding Factor Implicated in PR-10a Gene Activation in Potato," The Plant Cell, 12:1477-1489 (2000).
Di Stilio et al., "Virus-Induced Gene Silencing as a Tool for Comparative Functional Studies in Thalictrum," PLoS One, 5(8):e12064 (2010).
Diallo et al., "Long Endogenous dsRNAs Can Induce Complete Gene Silencing in Mammalian Cells and Primary Cultures," Oligonucleotides, 13:381-392 (2003).
Dietemann et al., "Varroa destructor: research avenues towards sustainable control," Journal of Apicultural Research, 51(1):125-132 (2012).
Dietzgen et al., "Transgenic gene silencing strategies for virus control," Australasian Plant Pathology, 35:605-618 (2006).
Dilpreet et al., "Glyphosate Rsistance in a Johnsongrass (*Sorghum halepense*) Biotype from Arkansas," Weed Science, 59(3):299-304 (2011).
Downey et al., "Single and dual parasitic mite infestations on the honey bee, *Apis mellifera* L.," Insectes Sociaux, 47(2):171-176 (2000).
Drobyazko R.V. "Reliable and environmentally friendly insecticide," Protection and quarantine of plants, 2012 (pp. 52, 53) (in Russian).
Du et al., "A systematic analysis of the silencing effects of an active siRNA at all single-nucleotide mismatched target sites," Nucleic Acids Research, 33(5):1671-1677 (2005).
Duhoux et al., "Reference Genes to Study Herbicide Stress Response in *Lolium sp*.: Up-Regulation of P3450 Genes in Plants Resistant to Acetolactate-Synthase Inhibitors," PLOS One, 8(5):e63576 (2013).
Dunoyer et al., "Small RNA Duplexes Function as Mobile Silencing Signals Between Plant Cells," Science, 328:912-916 (2010).
Eamens et al., "RNA Silencing in Plants: Yesterday, Today, and Tomorrow," Plant Physiology, 147(2):456-468 (2008).
Egli et al., "A Maize Acetyl-Coenzyme A Carboxylase cDNA Sequence," Plant Physiol., 108: 1299-1300 (1995).
Ellington et al., "In vitro selection of RNA molecules that bind specific ligands," Nature, 346:818-822 (1990).
Emery et al., "Radial Patterning of *Arabidopsis* Shoots by Class III HD-ZIP and KANADI Genes," Current Biology, 13:1768-1774 (2003).
Eudes et al., "Cell-penetrating peptides," Plant Signaling & Behavior, 3(8):549-5550 (2008).
European Cooperation in the field of Scientific and Technical Research—Memorandum of Understanding for COST Action FA0806 (2008).
European Search Report dated Sep. 7, 2017, in European Patent Application No. 17152830.0.
Examination Report dated Mar. 1, 2018, in Australian Patent Application No. 2013264742.
Extended European Search Report dated Dec. 19, 2018, in European Patent Application No. 16804395.8.
Extended European Search Report dated Feb. 2, 2015, in European Patent Application No. 12 830 932.5.
Extended European Search Report dated Feb. 27, 2015, in European Patent Application No. 12 832 160.1.
Extended European Search Report dated Feb. 3, 2015, in European Patent Application No. 12 831 945.6.
Extended European Search Report dated Jan. 20, 2016, in European Patent Application No. 13 794 339.5.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Jun. 29, 2015, in European Patent Application No. 12 831 494.5.
Extended European Search Report dated Mar. 17, 2015, in European Patent Application No. 12 831 684.1.
Extended European Search Report dated Mar. 3, 2015, in European Patent Application No. 12 831 166.9.
Extended European Search Report dated Nov. 16, 2018, in European Patent Application No. 18182238.8.
Extended European Search Report dated Nov. 21, 2018, in European Patent Application No. 18175809.5.
Extended European Search Report dated Nov. 7, 2017, in European Patent Application No. 15811092.4.

(56) References Cited

OTHER PUBLICATIONS

Extended European Search Report dated Nov. 8, 2017, in European Patent Application No. 15737282.2.
Extended European Search Report dated Oct. 8, 2013, in European Patent Application No. 11753916.3.
Extended European Search Report dated Sep. 28, 2018, in European Patent Application No. 16740770.9.
Extended European Search Report dated Sep. 29, 2016, in European Patent Application No. 14778840.0.
Extended European Search Report dated Apr. 13, 2018, in European Patent Application No. 15812530.0.
Extended European Search Report dated Mar. 15, 2018, in European Patent Application No. 17181861.0.
Farooq et al., "Rice seed priming," IPRN, 30(2):45-48 (2005).
Fassler, BLAST Glossary, National Center for Biotechnology Information (2011).
Fernandez et al., "Uptake of Hydrophilic Solutes Through Plant Leaves: Current State of Knowledge and Perspectives of Foliar Fertilization," Critical Reviews in Plant Sciences, 28:36-38 (2009).
Feuillet et al., "Crop genome sequencing: lessons and rationales," Trends Plant Sci., 16:77-88 (2011).
Final Office Action dated Apr. 7, 2016, in U.S. Appl. No. 13/619,980.
Final Office Action dated Dec. 17, 2015, in U.S. Appl. No. 14/335,135.
Final Office Action dated Feb. 17, 2016, in U.S. Appl. No. 13/612,929.
Final Office Action dated Feb. 4, 2016, in U.S. Appl. No. 13/612,936.
Final Office Action dated Jun. 30, 2016, in U.S. Appl. No. 13/901,326.
Final Office Action dated Mar. 2, 2016, in U.S. Appl. No. 13/612,995.
Final Office Action dated Mar. 21, 2016, in U.S. Appl. No. 13/612,925.
Final Office Action dated May 26, 2016, in U.S. Appl. No. 14/532,596.
Final Office Action dated Nov. 10, 2015, in U.S. Appl. No. 13/612,985.
Final Office Action dated Nov. 10, 2016, in U.S. Appl. No. 13/583,302.
Final Office Action dated Nov. 19, 2015, in U.S. Appl. No. 13/612,941.
Final Office Action dated Nov. 30, 2015, in U.S. Appl. No. 13/612,948.
Final Office Action dated Nov. 7, 2013, in U.S. Appl. No. 13/042,856.
Final Office Action dated Oct. 20, 2016, in U.S. Appl. No. 14/480,199.
Final Office Action dated Oct. 22, 2015, in U.S. Appl. No. 14/608,951.
Final Office Action dated Sep. 9, 2016, in U.S. Appl. No. 13/612,954.
Final Office Action dated Sep. 9, 2016, in U.S. Appl. No. 14/608,951.
Final Office Action dated Sep. 9, 2016, in U.S. Appl. No. 14/603,347.
Fire et al., "Potent and specific genetic interference by double-stranded RNA in Caenorhabditis elegans," Nature, 391:806-811 (1998).
First Examination Report dated Apr. 23, 2013, in New Zealand Patent Application No. 601784.
First Examination Report dated Jul. 28, 2014, in New Zealand Patent Application No. 627060.
First Office Action dated Aug. 31, 2015, in Chinese Patent Application No. 201280053985.3.
First Office Action dated Feb. 2, 2016, in Chinese Patent Application No. 201380039346.6.
First Office Action dated Jul. 7, 2015, in Chinese Patent Application No. 201280054820.8.
First Office Action dated Mar. 12, 2015, in Chinese Patent Application No. 201280053984.9.
First Office Action dated Mar. 2, 2015, in Chinese Patent Application No. 201280054819.5.
First Office Action dated May 27, 2015, in Chinese Patent Application No. 201280054179.8.
First Office Action dated Sep. 9, 2015, in Chinese Patent Application No. 201280055109.2.
Fraley et al., "Liposome-mediated delivery of tobacco mosaic virus RNA into tobacco protoplasts: A sensitive assay for monitoring liposome-protoplast interactions," Proc Natl Acad Sci U S A., 79(6):1859-1863 (1982).
Friedberg, "Automated protein function prediction—the genomic challenge," Briefings in Bioinformatics, 7(3):225-242 (2006).
Fukuhara et al., "Enigmatic Double-Stranded RNA in Japonica Rice," Plant Molecular Biology, 21:1121-1130 (1993).
Fukuhara et al., "The Unusual Structure of a Novel RNA Replicon in Rice," The Journal of Biological Chemistry, 270(30):18147-18149 (1995).
Fukuhara et al., "The wide distribution of endornaviruses, large double-stranded RNA replicons with plasmid-like properties," Archives of Virology, 151:995-1002 (2006).
Fukunaga et al., "dsRNA with 5' overhangs v contributes to endogenous and antiviral RNA silencing pathways in plants," The EMBO Journal, 28(5):545-555 (2009).
Funke et al., "Molecular basis for herbicide resistance in Roundup Ready crops," PNAS, 103:13010-13015 (2006).
Further Examination Report dated May 16, 2014, in New Zealand Patent Application No. 601784.
Gaines et al., "Gene amplification confers glyphosate resistance in Amaranthus palmeri," Proc. Natl. Acad. Sci. USA, 107(3):1029-1034 (2010).
Gallie et al., "Identification of the motifs within the tobacco mosaic virus 5' leader responsible for enhancing translation," Nucleic Acids Res., 20(17):4631-4638 (1992).
Gan et a., "Bacterially expressed dsRNA protects maize against SCMV infection," Plant Cell Rep, 29(11):1261-1268 (2010).
Gan et al., "Inhibition of Leaf Senescence by Autoregulated Production of Cytokinin," Science, 270:1986-1988 (1995).
Gao et al., "Down-regulation of acetolactate synthase compromises 01-1-mediated resistance to powdery mildew in tomato," BMC Plant Biology, 14(2014).
Gao et al., "Nonviral Methods for siRNA Delivery," Molecular Pharmaceutics, 6(3):651-658 (2008).
Garbian et al., "Bidirectional Transfer of RNAi between Honey Bee and Varroa destructor: Varroa Gene Silencing Reduces Varroa Population," 8(12):1-9:e1003035 (2012).
Gaskin et al., "Novel organosillicone adjuvants to reduce agrochemical spray volumes on row crops," New Zealand Plant Protection, 53:350-354 (2000).
Gasser et al., "Structure, Expression, and Evolution of the 5-Enolpyruvylshikimate-3-phosphate Synthase Genes of Petunia and Tomato," J. Biol. Chem., 263: 4280-4287 (1988).
Ge et al., "Rapid vacuolar sequestration: the horseweed glyphosate resistance mechanism," Pest Management Sci., 66:345-348 (2010).
GenBank Accession No. AY545657.1 (2004).
GenBank Accession No. CB377464, "CmaE1_37_J02_T3 Cowpea weevil larvae Lambda Zap Express Library Callosobruchus maculatus cDNA, mRNA sequence," (2007).
GenBank Accession No. DY640489, "PU2_plate27_F03 PU2 Prunus persica cDNA similar to expressed mRNA inferred from Prunus persica hypothetical domain/motif cont aining IPR011005:Dihydropteroate synthase-like, MRNA sequence" (2006).
GenBank Accession No. EF143582 (2007).
GenBank Accession No. EU024568, "Amaranthus hypochondriacus acetolactate synthase (ALS) gene" (2007).
GenBank Accession No. EW765249, "ST020010B10C12 Normalized and subtracted western corn rootworm female head cDNA library Diabrotica virgifera virgifera cDNA clone STO20010B10C12 5-, mRNA sequence," (2007).
GenBank Accession No. EW771198, "ST020010B10C12 Normalized and subtracted western corn rootworm female head cDNA library Diabrotica virgifera virgifera cDNA clone STO20010B10C12 5-, mRNA sequence," (2007).
GenBank Accession No. FE348695, "CBIB7954.fwd CBIB_Daphnia_pulex_Chosen_One_Library_2 Daphnia pulex cDNA clone CBIB7954 5', mRNA sequence" (2011).
GenBank Accession No. FJ972198, "Solanum lycopersicum cultivar Ailsa Craig dihydropterin pyrophosphokinase-dihydropteroate synthase (HPPK-DHPS) gene, complete cds" (2010).
GenBank Accession No. GI:186478573 (2014).
GenBank Accession No. GU120406, "Chrysomela tremulae ribosomal protein L7 (RpL7) mRNA, complete cds" (2009).
GenBank Accession No. HD315444, "Sequence 192160 from Patent EP2213738" (2010).
GenBank Accession No. Q4GXM3_BIPLU, "Ribosomal protein L7e" (2006).
GenBank Accession No. U87257.1, "Daucus carota 4-hydroxyphenylpyruvate dioxygenase mRNA, complete cds" (1997).

(56) References Cited

OTHER PUBLICATIONS

GenBank Accession No. XM_014456745.1, PREDICTED: Myotis lucifugus ribonucleoprotein, PTB-binding 2 (RAVER2), transcript variant X3, mRNA,: (2015).
GenBank Accession No. Y08611.1, "P.sativum mRNA for dihydropterin pyrophosphokinase/dihydropteroate synthase " (2006).
GenEmbl Accession No. FJ861243 (2010).
Gilmer et al., "Latent Viruses of Apple I. Detection with Woody Indicators," Plant Pathology, 1(10):1-9 (1971).
Gomez-Zurita et al., "Recalibrated Tree of Leaf Beetles (Chrysomelidae) Indicates Independent Diversification of Angiosperms and Their Insect Herbivores," PLoS One, 4(e360):1-8 (2007).
Gong et al., "Silencing of Rieske iron-sulfur protein using chemically synthesised siRNA as a potential biopesticide against Plutella xylostella," Pest Manag Sci, 67:514-520 (2011).
Gossamer Threads, Compendium of Herbicide Adjuvants: Organo-Silicone Surfactant, p. 1-4 (1998).
Gressel et al., "A strategy to provide long-term control of weedy rice while mitigating herbicide resistance transgene flow, and its potential use for other crops with related weeds," Pest Manag Sci, 65(7):723-731 (2009).
Gudkov, "Minireview: The L7/L12 ribosomal domain of the ribosome: structural and functional studies," FEBS Letters, 407:253-256 (1997).
Gutensohn et al., "Functional analysis of the two *Arabidopsis* homologues of Toc34, a component of the chloroplast protein import apparatus," The Plant Journal, 23(6):771-783 (2000).
Guttieri et al., "DNA Sequence Variation in Domain a of the Acetolactate Synthase Genes of Herbicide-Resistant and -Susceptible Weed Biotypes," Weed Science, 40:670-679 (1992).
Hagio, "Chapter 25: Direct Gene Transfer into Plant Mature Seeds via Electroporation After Vacuum Treatment," Electroporation and Sonoporation in Developmental Biology, p. 285-293 (2009).
Haigh, "The Priming of Seeds: Investigation into a method of priming large quantities of seeds using salt solutions," Thesis submitted to Macquarie University (1983).
Hajirezaei et al., "Impact of elevated cytosolic and apoplastic invertase activity on carbon metabolism during potato tuber development," Journal of Experimental Botany, 51:439-445 (2000).
Hamilton et al., "Guidelines for the Identification and Characterization of Plant Viruses," J. gen. Virol., 54:223-241 (1981).
Hamilton et al., "Two classes of short interfering RNA in RNA silencing," EMBO J., 21(17):4671-4679 (2002).
Han et al., "Molecular Basis for the Recognition of Primary microRNAs by the Drosha-DGCR8 Complex," Cell, 125(5):887-901 (2006).
Hannon, "RNA interference," Nature,481:244-251 (2002).
Hardegree, "Drying and storage effects on germination of primed grass seeds," Journal of Range Management, 47(3):196-199 (1994).
Harrison et al., "Does Lowering Glutamine Synthetase Activity in Nodules Modigy Nitrogen Metabolism and Growth of Lotus japonicus? ," Plant Physiology, 133:253-262 (2003).
Heffer et al., "Rapid isolation of gene homologs across taxa: Efficient identification and isolation of gene orthologs from non-model organism genomes, a technical report," EvoDevo Journal, 2(7):1-5 (2011).
Herman et al., "A three-component dicamba O-demethylase from Pseudomonas maltophilia, strain DI-6: gene isolation, characterization, and heterologous expression," J. Biol. Chem., 280: 24759-24767 (2005).
Hess, "Surfactants and Additives," 1999 Proceedings of the California Weed Science Society, 51:156-172 (1999).
Hewezi et al., "Local infiltration of high- and low-molecular-weight RNA from silenced sunflower (*Helianthus annuus* L.) plants triggers post-transcriptional gene silencing in non-silenced plants," Plant Biotechnology Journal, 3:81-89 (2005).
Hidayat et al., "Enhanced Metabolism of Fluazifop Acid in a Biotype of Herewith Digitaria sanguinalis Resistant to the Herbicide Fluazifop-P-Butyl," Pesticide Biochem. Physiol., 57:137-146 (1997).
Himber et al., "Transitivity-dependant and -independent cell-to-cell movement of RNA silencing," The EMBO Journal, 22(17):4523-4533 (2003).
Hirschberg et al., "Molecular Basis of Herbicide Resistance in Amaranthus hybridus," Science, 222:1346-1349 (1983).
Hoekema et al., "A binary plant vector strategy based on separation of vir- and T-region of the Agrobacterium tumefaciens Ti-plasmid," Nature, 303:179-180 (1983).
Hofgen et al., "Repression of Acetolactate Synthase Activity through Antisense Inhibition: Molecular and Biochemical Analysis of Transgenic Potato (*Solanum tuberosum* L. cv Desiree) Plants," Plant Physiol., 107(2):469-477 (1995).
Holtra et al., "Assessment of the Physiological Condition of Salvinia Natans L. Exposed to Copper(II) Ions," Environ. Protect. Eng., 41:147-158 (2015).
Horsch et al., "Inheritance of Functional Foreign Genes in Plants ," Science, 223:496-498 (1984).
Hsieh et al., "A library of siRNA duplexes targeting the phosphoinositide 3-kinase pathway: determinants of gene silencing for use in cell-based screens," Nucleic Acids Res., 32(3):893-901 (2004).
Hu et al., "High efficiency transport of quantum dots into plant roots with the aid of silwet L-77," Plant Physiology and Biochemistry, 48:703-709 (2010).
Huang et al., "In Vivo Analyses of the Roles of Essential Omp85-Related Proteins in the Chloroplast Outer Envelope Membrane," Plant Physiol., 157:147-159 (2011).
Huesken et al., "Design of a genome-wide siRNA library using an artificial neural network," Nature Biotechnology, 23(8): 995-1001 (2005).
Huggett et al., "Real-time RT-PCR normalisation; strategies and considerations," Genes and Immunity, 6:279-284 (2005).
Hunter et al., "RNA Interference Strategy to suppress Psyllids & Leafhoppers," International Plant and Animal Genome XIX, 15-19 (2011).
Ichihara et al., "Thermodynamic instability of siRNA duplex is a prerequisite for dependable prediction of siRNA activities," Nucleic Acids Res., 35(18):e123 (2007).
Inaba et al., "*Arabidopsis* Tic110 is Essential for the Assembly and Function of the Protein Import Machinery of Plastids," The Plant Cell, 17:1482-1496 (2005).
International Preliminary Report on Patentability (Chapter II) dated Jul. 24, 2015, in International Application No. PCT/US2014/047204.
International Preliminary Report on Patentability dated Sep. 11, 2012, in International Application No. PCT/US2011/027528.
International Preliminary Report on Patentability dated Sep. 11, 2014, in International Application No. PCT/IL2013/050447.
International Rice Genome Sequencing Project, The map-based sequence of the rice genome, Nature, 436(11):793-800 (2005).
International Search Report and the Written Opinion dated Feb. 25, 2013, in International Application No. PCT/US2012/054883.
International Search Report and the Written Opinion dated Feb. 27, 2013, in International Application No. PCT/US2012/054814.
International Search Report and the Written Opinion dated Feb. 27, 2013, in International Application No. PCT/US2012/054842.
International Search Report and the Written Opinion dated Feb. 27, 2013, in International Application No. PCT/US2012/054862.
International Search Report and the Written Opinion dated Feb. 27, 2013, in International Application No. PCT/US2012/054894.
International Search Report and the Written Opinion dated Feb. 27, 2013, in International Application No. PCT/US2012/054974.
International Search Report and the Written Opinion dated Feb. 27, 2013, in International Application No. PCT/US2012/054980.
International Search Report and the Written Opinion dated Jul. 15 2014, in International Application No. PCT/US2014/025305.
International Search Report and the Written Opinion dated Jul. 22 2014, in International Application No. PCT/IL2013/051083.
International Search Report and the Written Opinion dated Jul. 22 2014, in International Application No. PCT/IL2013/051085.
International Search Report and the Written Opinion dated Jul. 24 2014, in International Application No. PCT/US2014/026036.
International Search Report and the Written Opinion dated May 10, 2011, in International Application No. PCT/US2011/027528.

(56) References Cited

OTHER PUBLICATIONS

International Search Report and the Written Opinion dated Oct. 1, 2013, in International Application No. PCT/IL2013/050447.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Feb. 23, 2015, in International Application No. PCT/US2014/063832.
International Search Report and Written Opinion dated Jul. 8, 2015, in International Application No. PCT/US2015/011408.
International Search Report and Written Opinion dated Mar. 26, 2015, in International Application No. PCT/US2014/069353.
International Search Report and Written Opinion dated May 26, 2016, in International Application No. PCT/US2016/014344.
International Search Report and Written Opinion dated Nov. 24, 2015, in International Application No. PCT/US2015/037522.
International Search Report and Written Opinion dated Nov. 27, 2015, in International Application No. PCT/US2015/037015.
International Search Report dated Mar. 12, 2013, in International Application No. PCT/US2012/054789.
International Search Report dated Oct. 13, 2016, in International Patent Application No. PCT/US2016/35500.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.
Isaacs et al., "Engineered riboregulators enable post-transcriptional control of gene expression," Nature Biotechnology, 22(7):841-847 (2004).
Ivanova et al., "Members of the Toc159 Import Receptor Family Represent Distinct Pathways for Protein Targeting to Plastids," Molecular Biology of the Cell, 15:3379-3392 (2004).
Jacque et al., "Modulation of HIV-1 replication by RNA interference," Nature, 418, 435-438 (2002).
Jang et al., "Resistance to herbicides caused by single amino acid mutations in acetyl-CoA carboxylase in resistant populations of grassy weeds," New Phytologist, 197(4):1110-1116 (2013).
Jarvis et al, "An *Arabidopsis* mutant defective in the plastid general protein import apparatus," Science, 282:100-103 (1998).
Ji et al., "Regulation of small RNA stability: methylation and beyond," Cell Research, 22:624-636 (2012).
Jiang et al., Chapter III Seeds and Seedlings, Botany, Northwest A&F University Press, pp. 87-92 (2009).
Jin et al., "Posttranslational Elevation of Cell Wall Invertase Activity by Silencing its Inhibitor in Tomato Delays Leaf Senescence and Increases Seed Weight and Fruit Hexose Level," The Plant Cell, 21:2072-2089 (2009).
Jofre-Garfias et al., "Agrobacterium-mediated transformation of Amaranthus hypochondriacus: light- and tissue-specific expression of a pea chlorophyll a/b-binding protein promoter," Plant Cell Reports, 16:847-852 (1997).
Jones-Rhoades et al., "MicroRNAs and Their Regulatory Roles in Plants," Annu Rev. Plant Biol., 57:19-53 (2006).
Josse et al., "A DELLA in Disguise: SPATULA Restrains the Growth of the Developing *Arabidopsis* Seedling," Plant Cell, 23:1337-1351 (2011).
Kaloumenos et al., "Identification of a Johnsongrass (*Sorghum halepense*) Biotype Resistant to ACCase-Inhibiting Herbicides in Northern Greece," Weed Technol, 23:470-476 (2009).
Kam et al., "Nanotube Molecular Transporters: Internalization of Carbon Nanotube—Protein Conjugates into Mammalian Cells," J. Am. Chem. Soc., 126(22):6850-6851 (2004).
Kambiranda et al., "Relationship Between Acid Invertase Activity and Sugar Content in Grape Species," Journal of Food Biochemistry, 35:1646-1652 (2011).
Katoh et al., "Specific residues at every third position of siRNA shape its efficient RNAi activity," Nucleic Acids Res., 35(4): e27 (2007).
Kertbundit et al., "In vivo random β-glucuronidase gene fusions in *Arabidopsis thaliana*," Proc. Natl. Acad. Sci. U S A., 88:5212-5216 (1991).
Khachigian, "DNAzymes: Cutting a path to a new class of therapeutics," Curr Opin Mol Ther 4(2):119-121 (2002).
Khan et al., "Matriconditioning of Vegetable Seeds to Improve Stand Establishment in Early Field Plantings," J. Amer. Soc. Hort. Sci., 117(1):41-47 (1992).
Khanbekova et al., The defeat of the honey bee apis *Melifera caucasica* Gorb. by viruses and parasites, and condition of bee colonies in different ecogeographical conditions of Greater Caucasus, Agricultural Biology. 2013 (p. 43) (in Russian).
Khodakovskaya et al., "Carbon Nanotubes are Able to Penetrate Plant Seed Coat and Dramatically Affect Seed Germination and Plant Growth," ACS Nano, 3(10):3221-3227 (2009).
Kikkert et al., "Stable Transformation of Plant Cells by Particle Bombardment/Biolistics," Methods in Molecular Biology, 286:61-78 (2005).
Kim et al., "Synthesis and characterization of mannosylated pegylated polyethylenimine as a carrier for siRNA," International Journal of Pharmaceutics, 427:123-133 (2012).
Kim et al., "Optimization of Conditions for Transient Agrobacterium-Mediated Gene Expression Assays in *Arabidopsis*," Plant Cell Reports, 28:1159-1167 (2009).
Kim et al., "Synthetic dsRNA Dicer substrates enhance RNAi potency and efficacy," Nature Biotechnology, 23(2):222-226 (2005).
Kirkwood, "Herbicides and Plants," Botanical Journal of Scotland, 46(3):447-462 (1993).
Kirkwood, "Recent developments in our understanding of the plant cuticle as a barrier to the foliar uptake of pesticides," Pestic Sci, 55:69-77 (1999).
Kirkwood, "Use and Mode of Action of Adjuvants for Herbicides: A Review of some Current Work," Pestic. Sci., 38:93-102 (1993).
Klahre et al., "High molecular weight RNAs and small interfering RNAs induce systemic posttranscriptional gene silencing in plants," Proc. Natl. Acad. Sci. USA, PNAS, 99(18):11981-11986 (2002).
Knudsen, "Promoter2.0: for the recognition of PolI promoter sequences," Bioniformatics, 15(5):356-361 (1999).
Kovacheva et al., "Further in vivo studies on the role of the molecular chaperone, Hsp93, in plastid protein import," The Plant Journal, 50:364-379 (2007).
Kovacheva et al., "In vivo studies on the roles of Tic100, Tic40 and Hsp93 during chloroplast protein import," The Plant Journal, 41:412-428 (2005).
Kronenwett et al., "Oligodeoxyribonucleotide Uptake in Primary Human Hematopoietic Cells is Enhanced by Cationic Lipids and Depends on the Hematopoietic Cell Subset." Blood. (1(3):852-862 (1998).
Kumar et al., "Sequencing, De Novo Assembly and Annotation of the Colorado Potato Beetle, *Leptinotarsa decemlineata*, Transcriptome," PLoS One, 9(1):e86012 (2014).
Kusaba et al., "Low glutelin content1: A Dominant Mutation That Suppresses the Glutelin Multigene Family via RNA Silencing ni Rice," The Plant Cell, 15(6):1455-1467 (2003).
Kusaba, "RNA interference in crop plants," Curr Opin Biotechnol, 15(2):139-143 (2004).
Lavigne et al., "Enhanced antisense inhibition of human immunodeficiency virus type 1 in cell cultures by DLS delivery system," Biochem Biophys Res Commun, 237:566-571 (1997).
Lee et al., "Aptamer Database," Nucleic Acids Research, 32:D95-D100 (2004).
Lein et al., "Target-based discovery of novel herbicides," Current Opinion in Plant Biology, 7:219-225 (2004).
Leopold et al., "Chapter 4: Moisture as a Regulator of Physiological Reaction in Seeds," Seed Moisture, CSSA Special Publication No. 14, pp. 51-69 (1989).

(56) References Cited

OTHER PUBLICATIONS

Lermontova et al., "Reduced activity of plastid protoporphyrinogen oxidase causes attenuated photodynamic damage during high-light compared to low-light exposure," The Plant Journal, 48(4):499-510 (2006).
Lesnik et al., "Prediction of rho-independent transcriptional terminators in *Escherichia coli*," Nucleic Acids Research, 29(17):3583-3594 (2001).
Li et al., "A Simplified Seed Transformation Method for Obtaining Transgenic *Brassica napus* Plants," Agricultural Sciences in China, 8(6):658-663 (2009).
Li et al., "Establishment of a highly efficient transformation system for pepper (*Capsicum annuum* L.)," Plant Cell Reports, 21: 785-788 (2003).
Li et al., "The FAST technique: a simplified Agrobacterium-based transformation method for transient gene expression analysis in seedlings of *Arabidopsis* and other plant species," Plant Methods, 5(6):1-15 (2009).
Li et at., "Long dsRNA but not siRNA initiates RNAi in western corn rootworm larvae and adults," Journal of Applied Entomology, 139(6):432-445 (2015).
Liu et al, "The Helicase and RNaseIIIa Domains of *Arabidopsis* Dicer-Like1 Modulate Catalytic Parameters during MicroRNA Biogenesis," Plant Physiology, 159:748-758 (2012).
Liu et al., "Carbon Nanotubes as Molecular Transporters for Walled Plant Cells," Nano Letters, 9(3):1007-1010 (2009).
Liu et al., "Comparative study on the interaction of DNA with three different kinds of surfactants and the formation of multilayer films," Bioelectrochemistry, 70:301-307 (2007).
Liu et al., "Identification and Application of a Rice Senescence-Associated Promoter," Plant Physiology, 153:1239-1249 (2010).
Liu, "Calmodulin and Cell Cycle," Foreign Medical Sciences Section of Pathophysiology and Clinical Medicine, 18(4):322-324 (1998).
Liu, "Confocal laser scanning microscopy—an attractive tool for studying the uptake of xenobiotics into plant foliage," Journal of Microscopy, 213(Pt 2):87-93 (2004).
Liu, "Influence of Sugars on the Foliar Uptake of Bentazone and Glyphosate," New Zealand Plant Protection, 55:159-162 (2002).
Liu, "The Transformation of Nucleic Acid Degradants in Plants," China Organic Fertilizers, Agriculture Press, ISBN: 7-1091634 (1991) (with English translation).
Llave et al., "Endogenous and Silencing-Associated Small RNAs in Plants," The Plant Cell, 14:1605-1619 (2002).
Lodish et al., Molecular Cell Biology, Fourth Edition, p. 210 (2000).
Lu et al., "OligoWalk: an online siRNA design tool utilizing hybridization thermodynamics," Nucleic Acids Research, 36:W104-W108 (2008).
Lu et al., "RNA silencing in plants by the expression of siRNA duplexes," Nucleic Acids Res., 32(21):e171 (2004).
Lucas et al., "Plasmodesmata—bridging the gap between neighboring plant cells," Trends in Cell Biology, 19:495-503 (2009).
Luft, "Making sense out of antisense oligodeoxynucleotide delivery: getting there is half the fun," J Mol Med, 76:75-76 (1998).
Luque et al., "Water Permeability of Isolated Cuticular Membranes: A Structural Analysis," Archives of Biochemistry and Biophysics, 317(2):417-422 (1995).
Maas et al., "Mechanism and optimized conditions for PEG mediated DNA transfection into plant protoplasts," Plant Cell Reports, 8:148-149 (1989).
MacKenzie et al., "Transgenic Nicotiana debneyii expressing viral coat protein are resistant to potato virus S infection," Journal of General Virology, 71:2167-2170 (1990).
Maher III et al "Inhibition of DNA binding proteins by oligonucleotide-directed triple helix formation," Science, 245(4919):725-730 (1989).
Makkouk et al., "Virus Diseases of Peas, Beans, and Faba Bean in the Mediterranean region," Adv Virus Res, 84:367-402 (2012).
Mandal et al., "Adenine riboswitches and gene activation by disruption of a transcription terminator," Nature Struct. Mol. Biol., 11(1):29-35 (2004).

Mandal et al., "Gene Regulation by Riboswitches," Nature Reviews | Molecular Cell Biology, 5:451-463 (2004).
Manoharan, "Oligonucleotide Conjugates as Potential Antisense Drugs with Improved Uptake, Biodistribution, Targeted Delivery, and Mechanism of Action," Antisense & Nucleic Acid Drug Development, 12:103-128 (2002).
Maori et al., "IAPV, a bee-affecting virus associated with Colony Collapse Disorder can be silenced by dsRNA ingestion," Insect Molecular Biology, 18(1):55-60 (2009).
Masoud, "Constitutive expression of an inducible β-1,3-glucanase in alfalfa reduces disease severity caused by the oomycete pathogen *Phytophthora megasperma* f. sp *medicaginis* . . . ," Trans Res, 5:313-323 (1996).
Matveeva et al., "Prediction of antisense oligonucleotide efficacy by in vitro methods," Nature Biotechnology, 16:1374-1375 (1998).
McGinnis, "RNAi for functional genomics in plants," Brief Funct Genomics, 9(2):111-7 (2010).
Meinke, et al., "Identifying essential genes in *Arabidopsis thaliana*," Trends Plant Sci., 13(9):483-491 (2008).
Meins et al., "RNA Silencing Systems and Their Relevance to Plant Development," Annu. Rev. Cell Dev. Biol., 21:297-318 (2005).
Melnyk et al., "Intercellular and systemic movement of RNA silencing signals," The EMBO Journal, 30:3553-3563 (2011).
Migge et al., "Greenhouse-grown conditionally lethal tobacco plants obtained by expression of plastidic glutamine synthetase antisense RNA may contribute to biological safety," Plant Science 153:107-112 (2000).
Misawa, "Expression of an Erwinia phytoene desaturase gene not only confers multiple resistance to herbicides interfering with carotenoid biosynthesis but also alters xanthophyll metabolism . . . ," The Plant Jrnl, 6(4):481-489 (1994).
Misawa, "Functional expression of the Erwinia uredovora carotenoid biosynthesis gene crtI in transgenic plants showing an increase of β-carotene biosynthesis activity and resistance ...," The Plant Jrnl, 4(5):833-840 (1993).
Miura et al., "The Balance between Protein Synthesis and Degradation in Chloroplasts Determines Leaf Variegation in *Arabidopsis* yellow variegated Mutants," The Plant Cell, 19:1313-1328 (2007).
Molina et al., "Inhibition of protoporphyrinogen oxidase expression in *Arabidopsis* causes a lesion-mimic phenotype that induces systemic acquired resistance," The Plant Journal, 17(6):667-678 (1999).
Molnar et al., "Plant Virus-Derived Small Interfering RNAs Originate redominantly from Highly Structured Single-Stranded Viral RNAs," Journal of Virology, 79(12):7812-7818 (2005).
Molnar et al., "Small Silencing RNAs in Plants are Mobile and Direct Epigenetic Modification in Recipient Cells," Science, 328:872-875 (2010).
Mora et al., "How Many Species are There on Earth and in the Ocean?," PLOS Biol., 9(8):e100127, p. 1-8 (2011).
Moriyama et al., "Double-stranded RNA in rice: a novel RNA replicon in plants," Molecular & General Genetics, 248(3):364-369 (1995).
Moriyama et al., "Stringently and developmentally regulated levels of a cytoplasmic double-stranded RNA and its high-efficiency transmission via egg and pollen in rice," Plant Molecular Biology, 31:713-719 (1996).
Morozov et al., "Evaluation of Preemergence Herbicides for Control of Diclofop-resistant Italian Ryegrass (*Lolium multiflorum*) in Virginia," Virginia Polytechnic Institute and State University, pp. 43-71 (2004).
Morrissey et al., "Potent and persistent in vivo anti-HBV activity of chemically modified siRNAs," Nat Biotechnol. 23(8):1002-1007 (2005).
Moser et al., "Sequence—Specific Cleavage of Double Helical DNA by Triple Helix Formation," Science, 238:645-646 (1987).
Mount et al., "Gene and Metabolite Regulatory Network Analysis of Early Developing Fruit Tissues Highlights New Candidate Genes for the Control of Tomato Fruit Composition and Development," Plant Physiology, 149:1505-1528 (2009).
Nemeth, "Virus, mycoplasma and rickettsia diseases of fruit trees," Martinus Nijhoff Publishers, 197-204 (1986).
Non-Final Office Action dated Apr. 11, 2013, in U.S. Appl. No. 13/042,856.

(56) References Cited

OTHER PUBLICATIONS

Non-Final Office Action dated Apr. 29, 2016, in U.S. Appl. No. 13/583,302.
Non-Final Office Action dated Aug. 10, 2016, in U.S. Appl. No. 13/612,995.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Aug. 19, 2016, in U.S. Appl. No. 13/612,925.
Non-Final Office Action dated Aug. 19, 2016, in U.S. Appl. No. 13/612,929.
Non-Final Office Action dated Aug. 3, 2016, in U.S. Appl. No. 14/015,715.
Non-Final Office Action dated Aug. 5, 2016, in U.S. Appl. No. 14/015,785.
Non-Final Office Action dated Aug. 8, 2016, in U.S. Appl. No. 13/612,936.
Non-Final Office Action dated Dec. 17, 2015, in U.S. Appl. No. 14/532,596.
Non-Final Office Action dated Feb. 10, 2016, in U.S. Appl. No. 13/901,326.
Non-Final Office Action dated Feb. 23, 2016, in U.S. Appl. No. 14/603,347.
Non-Final Office Action dated Feb. 23, 2016, in U.S. Appl. No. 14/608,951.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated Mar. 1, 2016, in U.S. Appl. No. 13/612,954.
Non-Final Office Action dated Mar. 21, 2018, in U.S. Appl. No. 13/619,980.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Non-Final Office Action dated Nov. 9, 2016, in U.S. Appl. No. 14/901,003.
Non-Final Office Action dated Oct. 3, 2016, in U.S. Appl. No. 14/403,491.
Non-Final Office Action dated Sep. 1, 2015, in U.S. Appl. No. 13/612,954.
Non-Final Office Action dated Sep. 11, 2015, in U.S. Appl. No. 13/612,925.
Non-Final Office Action dated Sep. 4, 2015, in U.S. Appl. No. 13/612,995.
Non-Final Office Action dated Sep. 6, 2016, in U.S. Appl. No. 14/335,135.
Nookaraju et al., "Molecular approaches for enhancing sweetness in fruits and vegetables," Scientia Horticulture, 127:1-15 (2010).
Nord-Larsen et al., "Cloning, characterization and expression analysis of tonoplast intrinsic proteins and glutamine synthetase in ryegrass (*Lolium perenne* L.)," Plant Cell Reports, 28(10):1549-1562 (2009).
Notice of Allowance dated Apr. 11, 2016, in U.S. Appl. No. 13/612,985.
Notice of Allowance dated Apr. 19, 2016, in U.S. Appl. No. 13/612,941.
Notice of Allowance dated Apr. 20, 2016, in U.S. Appl. No. 13/612,948.
Notice of Allowance dated Feb. 23, 2015, in U.S. Appl. No. 13/042,856.
Notice of Allowance dated Jun. 2, 2015, in U.S. Appl. No. 13/042,856.
Notice of Allowance dated Oct. 5, 2015, in U.S. Appl. No. 13/583,302.
Nowak et al., "A new and efficient method for inhibition of RNA viruses by DNA interference," The FEBS Journal, 276:4372-4380 (2009).
N-TER Nanoparticle siRNA, Sigma Aldrich TM website, Web. Nov. 20, 2018 <https://www.sigmaaldrich.com/life-science/custom-oligos/sirna-oligos/n-ter-nanoparticle.html>.
Office Action dated Apr. 13, 2016, in Chinese Patent Application No. 201280053985.3.
Office Action dated Aug. 1, 2017, in European Patent Application No. 12 830 932.5.
Office Action dated Aug. 14, 2017, in Israeli Patent Application No. 235878.
Office Action dated Aug. 22, 2017, in Korean Patent Application No. 10-2012-7023415.
Office Action dated Aug. 25, 2016, in Eurasian Patent Application No. 201201264.
Office Action dated Aug. 28, 2013, in Chinese Patent Application No. 201180012795.2.
Office Action dated Aug. 3, 2017, in Chinese Patent Application No. 201480014392.5 (with English translation).
Office Action dated Aug. 3, 2017, in European Patent Application No. 12 831 684.1.
Office Action dated Aug. 8, 2017, in Chilean Patent Application No. 201501874.
Office Action dated Aug. 9, 2018, in Canadian Patent Application No. 2,848,371.
Office Action dated Dec. 13, 2016, in Ukrainian Patent Application No. a 2014 03843.
Office Action dated Dec. 14, 2016, in Ukrainian Patent Application No. a 2014 03850.
Office Action dated Dec. 15, 2016, in Ukrainian Patent Application No. a 2014 03845.
Office Action dated Dec. 15, 2016, in Ukrainian Patent Application No. a 2014 03852.
Office Action dated Dec. 15, 2016, in Ukrainian Patent Application No. a 2014 03849.
Office Action dated Dec. 27, 2016, in Ukrainian Patent Application No. a 2012 11548.
Office Action dated Dec. 5, 2017, in Japanese Patent Application No. 2016-502033.
Office Action dated Feb. 17, 2014, in Mexican Patent Application No. MX/a/2012/010479.
Office Action dated Feb. 21, 2018, in Mexican Patent Application No. MX/a/2015/012632 (with English translation).
Office Action dated Feb. 24, 2014, in Eurasian Patent Application No. 201201264.
Office Action dated Jul. 11, 2017, in Mexican Patent Application No. MX/a/2015/013118 (with English translation).
Office Action dated Jul. 18, 2016, in Indonesian Patent Application No. W00201203610.
Office Action dated Jul. 23, 2015, in Ukrainian Patent Application No. 201211548.
Office Action dated Jul. 3, 2017, in Mexican Patent Application No. MX/a/2015/012632 (with English translation).
Office Action dated Jul. 30, 2018, in Canadian Patent Application No. 2,848,576.
Office Action dated Jul. 6, 2017, in Mexican Patent Application No. MX/a/2015/013103 (with English translation).
Office Action dated Jun. 20, 2016, in Chinese Patent Application No. 201280054819.5.
Office Action dated Jun. 24, 2016, in Chinese Patent Application No. 201280053984.9.
Office Action dated Mar. 16, 2017, in Chinese Patent Application No. 201280054819.5.
Office Action dated Mar. 8, 2018 (with English translation), in Chilean Patent Application No. 201403192.
Office Action dated May 3, 2016, in Chilean Patent Application No. 201601057.

(56) References Cited

OTHER PUBLICATIONS

Office Action dated Nov. 15, 2016, in Mexican Patent Application No. MX/a/2014/003068 (with English translation).
Office Action dated Sep. 20, 2018, in Chilean Patent Application No. 201601440 (with English translation).
Office Action dated Sep. 5, 2016, in Ukrainian Patent Application No. a 2014 03846.
Office Action dated Sep. 6, 2017, in Chinese Patent Application No. 2014800154012 (with English translation).
Office Action dated Nov. 3, 2014, in Chinese Patent Application No. 201180012795.2.
Office Action dated Jan. 6, 2015, in Japanese Patent Application No. 2012-557165.
Office Action dated Nov. 19, 2014, in Eurasian Patent Application No. 201201264/28.
Office Action dated Oct. 5, 2015, in Eurasian Patent Application No. 201201264/28.
Ongvarrasopone et al., "A Simple and Cost Effective Method to Generate dsRNA for RNAi Studies in Invertebrates," Science Asia, 33:35-39 (2007).
Orbović et al., "Foliar-Applied Surfactants and Urea Temporarily Reduce Carbon Assimilation of Grapefruit Leaves," J. Amer. Soc. Hort. Sci., 126(4):486-490 (2001).
Ouellet et al., "Members of the Acetohydroxyacid Synthase Muligene Family of *Brassica napus* Have Divergent Patterns of Expression," The Plant Journal, Blackwell Scientific Publications, Oxford, GB, 2(3):321-330 (1992).
Paddison et al., "Stable suppression of gene expression by RNAi in mammalian cells," Proc. Natl Acad. Sci. USA, 99(3):1443-1448 (2002).
Palauqui et al., "Activation of systemic acquired silencing by localised introduction of DNA," Current Biology, 9:59-66 (1999).
Parera et al., "Dehydration Rate after Solid Matrix Priming Alters Seed Performance of Shrunken-2 Corn," J. Amer. Soc. Hort. Sci., 119(3):629-635 (1994).
Partial European Search Report dated Jun. 29, 2018, in European Patent Application No. 18157745.3.
Partial European Search Report dated Dec. 6, 2017, in European Patent Application No. 17181861.0.
Partial Supplementary European Search Report dated Jan. 11, 2018, in European Patent Application No. 15812530.2.
Partial Supplementary European Search Report dated Mar. 2, 2015, in European Patent Application No. 12 831 494.5.
Partial Supplementary European Search Report dated Jan. 11, 2018, in European Patent Application No. 15812530.0.
Patent Examination Report No. 1 dated Feb. 8, 2016, in Australian Patent Application No. 2014262189.
Patent Examination Report No. 1 dated Jun. 17, 2016, in Australian Patent Application No. 2012308659.
Patent Examination Report No. 1 dated Jun. 17, 2016, in Australian Patent Application No. 2012308660.
Patent Examination Report No. 1 dated Jun. 8, 2017, in Australian Patent Application No. 2012308686.
Patent Examination Report No. 1 dated Nov. 11, 2013, in Australian Patent Application No. 2011224570.
Paungfoo-Lonhienne et al., "DNA is Taken up by Root Hairs and Pollen, and Stimulates Root and Pollen Tube Growth," Plant Physiology, 153:799-805 (2010).
Paungfoo-Lonhienne et al., "DNA uptake by *Arabidopsis* induces changes in the expression of CLE peptides which control root morphology," Plant Signaling & Behavior, 5(9):1112-1114 (2010).
Peretz et al., "A Universal Expression/Silencing Vector in Plants," Plant Physiology, 145:1251-1263 (2007).
Pornprom et al., "Glutamine synthetase mutation conferring target-site-based resistance to glufosinate in soybean cell selections," Pest Manag Sci, 2009; 65(2):216-222 (2009).
Powles et al., "Evolution in Action: Plants Resistant to Herbicides," Annual Review of Plant Biology, 61(1):317-347 (2010).
Pratt et al., "Sorghum Expressed Sequence Tags Identify Signature Genes for Drought, Pathogenesis, and Skotomorphogenesis from a Milestone Set of 16,801 Unique Transcripts," Plant Physiology, 139:869-884 (2005).
Pratt et al., "Amaranthus rudis and A. tuberculatus, One Species or Two?," Journal of the Torrey Botanical Society, 128(3):282-296 (2001).
Preston et al., "Multiple effects of a naturally occurring proline to threonine substitution within acetolactate synthase in two herbicide-resistant populations of Lactuca serriola," Pesticide Biochem. Physiol., 84(3):227-235 (2006).
Promoter Prediction for SEQ ID No. 1702 from 13/612929/MK/, Promoter 2.0 Prediction Results, pp. 1-4 (2016).
Promoter Prediction for SEQ ID No. 4 from 13/612995/MK/, Promoter 2.0 Prediction Results, pp. 1-3 (2016).
Promoter Prediction for SEQ ID No. 7 from 13/612936/MK/, Promoter 2.0 Prediction Results, pp. 1-2 (2016).
Promoter Prediction for SEQ ID No. 8 from 13/612,925/MK/, Promoter 2.0 Prediction Results, pp. 1-6 (2016).
Qiwei,"Advance in Dna interference," Progress in Veterinary Medicine, 30(1):71-75 (2009).
Rajur et al., "Covalent Protein—Oligonucleotide Conjugates for Efficient Delivery of Antisense Molecules," Bioconjug Chem., 8:935-940 (1997).
Rakoczy-Trojanowska, "Alternative Methods of Plant Transformation—a short review," Cellular & Molecular Biology Letters, 7:849-858 (2002).
Reddy et al "Organosilicone Adjuvants Increased the Efficacy of Glyphosate for Control of Weeds in Citrus (*Citrus* spp.)" HortScience 27(9):1003-1005 (1992).
Reddy et al., "Aminomethylphosphonic Acid Accumulation in Plant Species Treated with Glyphosate," J. Agric. Food Chem., 56(6):2125-2130 (2008).
Regalado,"The Next Great GMO Debate," MIT Technology Review,pp. 1-19 (2015) <https://www.technologyreview.com/s/540136/the-next-great-gmo-debate/>.
Reither et al., "Specificity of DNA triple helix formation analyzed by a FRET assay," BMC Biochemistry, 3:27 (2002).
Restriction Requirement dated Apr. 21, 2015, in U.S. Appl. No. 13/612,954.
Restriction Requirement dated Feb. 12, 2015, in U.S. Appl. No. 13/612,985.
Restriction Requirement dated Jul. 15, 2016, in U.S. Appl. No. 14/143,748.
Restriction Requirement dated Jul. 18, 2016, in U.S. Appl. No. 14/143,836.
Restriction Requirement dated Mar. 12, 2015, in U.S. Appl. No. 13/612,948.
Restriction Requirement dated Mar. 4, 2015, in U.S. Appl. No. 13/612,941.
Restriction Requirement dated May 4, 2015, in U.S. Appl. No. 13/612,929.
Restriction Requirement dated May 5, 2015, in U.S. Appl. No. 13/612,936.
Restriction Requirement dated May 7, 2015, in U.S. Appl. No. 13/612,925.
Restriction Requirement dated May 7, 2015, in U.S. Appl. No. 13/612,995.
Restriction Requirement dated Oct. 13, 2016, in U.S. Appl. No. 14/206,707.
Restriction Requirement dated Oct. 2, 2012, in U.S. Appl. No. 13/042,856.
Restriction Requirement dated Oct. 21, 2014, in U.S. Appl. No. 13/583,302.
Restriction Requirement dated Oct. 28, 2015, in U.S. Appl. No. 14/603,347.
Restriction Requirement dated Sep. 2, 2015, in U.S. Appl. No. 14/532,596.
Rey et al., "Diversity of Dicotyledenous-Infecting Geminiviruses and Their Associated DNA Molecules in Southern Africa, Including the South-West Indian Ocean Islands," Viruses, 4:1753-1791 (2012).

(56) References Cited

OTHER PUBLICATIONS

Riar et al., "Glyphosate Resistance in a Johnsongrass (*Sorghum halepense*) Biotype from Arkansas," Weed Science, 59:299-304 (2011).
Richardson et al., "Targeting and assembly of components of the TOC protein import complex at the chloroplast outer envelope membrane," Frontiers in Plant Science, 5:1-14 (2014).
Riggins et al., "Characterization of de novo transcriptome for waterhemp (*Amaranthus tuberculatus*) using GS-FLX 454 pyrosequencing and its application for studies of herbicide target-site genes," Pest Manag. Sci., 66:1042-1052 (2010).
Roberts, "Fast-track applications: The potential for direct delivery of proteins and nucleic acids to plant cells for the discovery of gene function," Plant Methods, 1(12):1-3 (2005).
Robson et al., "Leaf senescence is delayed in maize expressing the Agrobacterium IPT gene under the control of a novel maize senescence-enhanced promoter," Plant Biotechnology Journal, 2:101-112 (2004).
Roitsch et al., "Extracellular invertase: key metabolic enzyme and PR protein," Journal of Experimental Botany, 54(382):513-524 (2003).
Roitsch et al., "Function and regulation of plant invertases: sweet sensations," Trades in Plant Science, 9(12):606-613 (2004).
Rose et al., "Functional polarity is introduced by Dicer processing of short substrate RNAs," Nucleic Acids Research, 33(13):4140-4156 (2005).
Rothnie et al., Pararetroviruses and Retroviruses: A Comparative Review of Viral Structure and Gene Expression Strategies, Advances in Virus Research, 44:1-67 (1994).
Ruan et al., "Suppression of Sucrose Synthase Gene Expression Represses Cotton Fiber Cell Initiation, Elongation, and Seed Development," The Plant Cell, 15:952-964 (2003).
Ryabov et al., "Cell-to-Cell, but Not Long-Distance, Spread of RNA Silencing That Is Induced in Individual Epidermal Cells," Journal of Virology, 78(6):3149-3154 (2004).
Ryan, "Human endogenous retroviruses in health and disease: a symbiotic perspective," Journal of the Royal Society of Medicine, 97:560-565 (2004).
Salanenka et al., "Seedcoat Permeability: Uptake and Post-germination Transport of Applied Model Tracer Compounds," HortScience, 46(4):622-626 (2011).
Santoro et al., "A general purpose RNA-cleaving DNA enzyme," Proc. Natl. Acad. Sci. USA, 94:4262-4266 (1997).
Sathasivan et al., "Nucleotide sequence of a mutant acetolactate synthase gene from an imidazolinone-resistant *Arabidopsis thaliana* var. Columbia," Nucleic Acids Research, 18(8):2188-2193 (1990).
Schönherr et al., "Size selectivity of aqueous pores in astomatous cuticular membranes isolated from Populus canescens (Aiton) Sm. Leaves," Planta, 219:405-411 (2004).
Schönherr, "Water Permeability of Isolated Cuticular Membranes: The Effect of pH and Cations on Diffusion, Hydrodynamic Permeability and Size of Polar Pores in the Cutin Matrix," Planta, 128:113-126 (1976).
Schwab et al., "RNA silencing amplification in plants: Size matters," PNAS, 107(34):14945-14946 (2010).
Schweizer et al., "Double-stranded RNA interferes with gene function at the single-cell level in cereals," The Plant Journal, 24(6):895-903 (2000).
Schwember et al., "Drying Rates following Priming Affect Temperature Sensitivity of Germination and Longevity of Lettuce Seeds," HortScience, 40(3):778-781 (2005).
Scott et al., Botanical Insecticides for Controlling Agricultural Pests: Piperamides and the Colorado Potato Beetle *Leptinotarsa decemlineata* Say (Coleoptera: Chrysomelidae), Archives of Insect Biochemistry and Physiology, 54:212-225 (2003).
Search Report dated Jul. 24, 2017, in Chinese Patent Application No. 201480014392.5 (with English translation).
Search Report dated Oct. 20, 2017, in Chinese Patent Application No. 201380039346.6.

Second Chinese Office Action dated Jun. 10, 2014, in Chinese Patent Application No. 201180012795.2.
Second Office Action dated Feb. 25, 2016, in Chinese Patent Application No. 201280054179.8.
Second Office Action dated Mar. 4, 2016, in Chinese Patent Application No. 201280054820.8.
Seidman et al., "The potential for gene repair via triple helix formation," J Clin Invest., 112(4):487-494 (2003).
Selvarani et al., "Evaluation of seed priming methods to improve seed vigour of onion (*Allium cepa* cv. Aggregatum) and carrot (*Daucus carota*)," Journal of Agricultural Technology, 7(3):857-867 (2011).
Senthil-Kumar et al., "A systematic study to determine the extent of gene silencing in *Nicotiana benthamiana* and other Solanaceae species when heterologous gene sequences are used for virus-induced gene silencing," New Phytologist, 176:782-791 (2007).
Sharma et al., "A simple and efficient Agrobacterium-mediated procedure for transformation of tomato," J. Biosci., 34(3):423 433 (2009).
Shintani et al., "Antisense Expression and Overexpression of Biotin Carboxylase in Tobacco Leaves," Plant Physiol., 114:881-886 (1997).
Showalter, "Structure and Function of Plant Cell Wall Proteins," The Plant Cell, 5:9-23 (1993).
Sijen et al. "On the Role of RNA Amplification in dsRNA-Triggered Gene Silencing," Cell, 107:465-476 (2001).
Silwet L-77 Spray Adjuvant for agricultural applications, product description from Momentive Performance Materials, Inc. (2003).
Simeoni et al., "Insight into the mechanism of the peptide-based gene delivery system MPG: implications for delivery of siRNA into mammalian cells," Nucleic Acids Research, 31(11):2717-2724 (2003).
Singh et al., "Absorption and translocation of glyphosate with conventional and organosilicone adjuvants," Weed Biology and Management, 8:104-111 (2008).
Small, "RNAi for revealing and engineering plant gene functions," Current Opinion in Biotechnology, 18:148-153 (2007).
Snead et al., "Molecular basis for improved gene silencing by Dicer substrate interfering RNA compared with other siRNA variants," Nucleic Acids Research, 41(12):6209-6221 (2013).
Song et al., "Herbicide," New Heterocyclic Pesticide, Chemical Industry Press, 354-356 (2011).
Statement of Grounds and Particulars dated Sep. 1, 2017, in Australian Patent No. 2014262189.
Steeves et al., "Transgenic soybeans expressing siRNAs specific to a major sperm protein gene suppress Heterodera glycines reproduction," Funct. Plant Biol., 33:991-999 (2006).
Stevens et al., "New Formulation Technology—SILWET® Organosilicone Surfactants Have Physical and Physiological Properties Which Enhance the Performance of Sprays," Proceedings of the 9th Australian Weeds Conference, pp. 327-331 (1990).
Stevens, "Formulation of Sprays to Improve the Efficacy of Foliar Fertilisers," New Zealand Journal of Forestry Science, 24(1):27-34 (1994).
Stevens, "Organosilicone Surfactants as Adjuvants for Agrochemicals," Journal of Pesticide Science, 38:103-122 (1993).
Stock et al., "Possible Mechanisms for Surfactant-Induced Foliar Uptake of Agrochemicals," Pestic. Sci., 38:165-177 (1993).
Strat et al., "Specific and nontoxic silencing in mammalian cells with expressed long dsRNAs," Nucleic Acids Research, 34(13):3803-3810 (2006).
Street "Why is DNA (and not RNA) a stable storage form for genetic information?," Biochemistry Revisited, pp. 1-4 (2008).
Sudarsan et al., "Metabolite-binding RNA domains are present in the genes of eukaryotes," RNA, 9:644-647 (2003).
Summons to Attend Oral Proceedings Pursuant to Rule 115(1) EPC, dated Aug. 7, 2017, in European Patent Application No. 12832160.1.
Sun et al., "A Highly efficient Transformation Protocol for Micro-Tom, a Model Cultivar for Tomato Functional Genomics," Plant Cell Physiol., 47(3):426-431 (2006).
Sun et al., "Antisense oligodeoxynucleotide inhibition as a potent strategy in plant biology: identification of SUSIBA2 as a transcriptional activator in plant sugar signalling," The Plant Journal, 44:128-138 (2005).

(56) References Cited

OTHER PUBLICATIONS

Sun et al., "Sweet delivery—sugar translocators as ports of entry for antisense oligodeoxynucleotides in plant cells," The Plant Journal, 52:1192-1198 (2007).
Sun, "Characterization of Organosilicone Surfactants and Their Effects on Sulfonylurea Herbicide Activity," Thesis Submitted to the Faculty of the Virginia Polytechnic Institute and State University dated Apr. 5, 1996.
Sutton et al., "Activity of mesotrione on resistant weeds in maize," Pest Manag. Sci., 58:981-984 (2002).
Takasaki et al., "An Effective Method for Selecting siRNA Target Sequences in Mammalian Cells," Cell Cycle, 3:790-795 (2004).
Tang et al., "Efficient delivery of small interfering RNA to plant cells by a nanosecond pulsed laser-induced stress wave for post-transcriptional gene silencing," Plant Science, 171:375-381 (2006).
Tank Mixing Chemicals Applied to Peanut Crops: Are the Chemicals Compatible?, College of Agriculture & Life Sciences, NC State University, AGW-653, pp. 1-11 (2004).
Taylor, "Seed Storage, Germination and Quality," The Physiology of Vegetable Crops, pp. 1-36 (1997).
Temple et al., "Can glutamine synthetase activity levels be modulated in transgenic plants by the use of recombinant DNA technology?" Transgenic Plants and Plant Biochemistry, 22(4):915-920 (1994).
Temple et al., "Down-regulation of specific members of the glutamine synthetase gene family in Alfalfa by antisense RNA technology," Plant Molecular Biology, 37:535-547 (1998).
Templeton et al., "Improved DNA: liposome complexes for increased systemic delivery and gene expression," Nature Biotechnology, 15:647-652 (1997).
Teng et al., "Tic21 is an Essential Translocon Component for Protein Translocation across the Chloroplast Inner Envelope Membrane," The Plant Cell, 18:2247-2257 (2006).
Tenllado et al., "Crude extracts of bacterially expressed dsRNA can be used to protect plants against virus infections," BMC Biotechnology, 3:1-11 (2003).
Tenllado et al, "Double-Stranded RNA-Mediated Interference with Plant Virus Infection," Journal of Virology, 75(24):12288-12297 (2001).
Tenllado et al., "RNA interference as a new biotechnological tool for the control of virus diseases in plants," Virus Research, 102:85-96 (2004).
Tepfer, "Risk assessment of virus resistant transgenic plants," Annual Review of Phytopathology, 40:467-491 (2002).
The Seed Biology Place, Website Gerhard Leubner Lab Royal Holloway, University of London, <http://www.seedbiology.de/seedtechnology.asp.
Third Party Submission filed on Nov. 29, 2012 in U.S. Appl. No. 13/042,856.
Thomas et al., "Size constraints for targeting post-transcriptional gene silencing and for RNA-directed methylation in Nicotiana benthamiana using a potato virus X vector," The Plant Journal, 25(4):417-425 (2001).
Thompson, et al., "CLUSTAL W: improving the sensitivity of progressive multiple sequence alignment through sequence weighting, position-specific gap penalties and weight matrix choice," Nucl. Acids Res., 22(22):4673-4680 (1994).
Tice, "Selecting the right compounds for screening: does Lipinski's Rule of 5 for pharmaceuticals apply to agrochemicals?" Pest Management Science, 57(1):3-16 (2001).
Timmons et al., "Specific interference by ingested dsRNA," Nature, 395:854 (1998).
Tomari et al., "Perspective: machines for RNAi," Genes & Dev., 19:517-529 (2005).
Tomlinson, "Evidence that the hexose-to-sucrose ratio does not control the switch to storage product accumulation in oilseeds: analysis of tobacco seed development and effects . . . ," Jrnl of Exper Bot, 55(406):2291-2303 (2004).
Töpfer et al., "Uptake and Transient Expression of Chimeric Genes in Seed-Derived Embryos," Plant Cell, 1:133-139 (1989).
Toriyama et al., "Transgenic Rice Plants After Direct Gene Transfer Into Protoplasts," Bio/Technology, 6:1072-1074 (1988).
Townsend et al., "High frequency modification of plant genes using engineered zinc finger nucleases," Nature, 459:442-445 (2009).
Tran et al., "Control of specific gene expression in mammalian cells by co-expression of long complementary RNAs," FEBS Lett.;573(1-3):127-134 (2004).
Tranel et al., "Resistance of weeds to ALS-inhibiting herbicides: what have we learned?," Weed Science, 50:700-712 (2002).
TransIT-TKO® Transfection Reagent, Frequently Asked Questions, Web. 2019 <https://www.mirusbio.com/tech-resources/faqs/transit-tko-faqs>.
Trucco et al., "Amaranthus hybridus can be pollinated frequently by A. tuberculatus under filed conditions," Heredity, 94:64-70 (2005).
Tsugawa et al., "Efficient transformation of rice protoplasts mediated by a synthetic polycationic amino polymer," Theor Appl Genet, 97:1019-1026 (1998).
Turina et al., "Tospoviruses in the Mediterranean Area," Advances in Virus Research, 84:403-437 (2012).
Tuschl, "Expanding small RNA interference," Nature Biotechnol., 20: 446-448 (2002).
Tuschl, "RNA Interference and Small Interfering RNAs," ChemBiochem. 2(4):239-245 (2001).
Ui-Tei et al., "Guidelines for the selection of highly effective siRNA sequences for mammalian and chick RNA interference," Nucleic Acids Res., 32(3): 936-948 (2004).
Ulrich et al., "Large scale RNAi screen in Tribolium reveals novel target genes for pest control and the proteasome as prime target," BMC genomics, 16(1):671 (2015).
Unnamalai et al., "Cationic oligopeptide-mediated delivery of dsRNA for post-transcriptional gene silencing in plant cells," FEBS Letters, 566:307-310 (2004).
Unniraman et al., "Alternate Paradigm for Intrinsic Transcription Termination in Eubacteria," The Journal of Biological Chemistry, 276(45)(9):41850-41855 (2001).
Unniraman et al., "Conserved Economics of Transcription Termination in Eubacteria," Nucleic Acids Research, 30(3):675-684 (2002).
Urayama et al., "Knock-down of OsDCL2 in Rice Negatively Affects Maintenance of the Endogenous dsRNA Virus, *Oryza sativa* Endornavirus," Plant and Cell Physiology, 51(1):58-67 (2010).
Van de Wetering et al., "Specific inhibition of gene expression using a stably integrated, inducible small-interfering-RNA vector," EMBO Rep., 4(6):609-615 (2003).
Van der Meer et al., "Promoted analysis of the chalcone synthase (chs A) gene of Petunia hybrid: a 67 bp promoter region directs flower-specific expression," Plant Mol. Biol., 15:95-109 (1990).
Vasil et al., "Herbicide Resistant Fertile Transgenic Wheat Plants Obtained by Microprojectile Bombardment of Regenerable Embryogenic Callus," Bio/Technology,10:667-674 (1992).
Vaucheret, "Post-transcriptional small RNA pathways in plants: mechanisms and regulations," Genes Dev., 20:759-771 (2006).
Vencill et al., "Resistance of Weeds to Herbicides," Herbicides and Environment, 29:585-594 (2011).
Verma et al., "Modified oligonucleotides: synthesis and strategy for users," Annu Rev. Biochem., 67:99-134 (1998).
Vermeulen et al., "The contributions of dsRNA structure to Dicer specificity and efficiency," RNA, 11(5):674-682 (2005).
Vert et al., "An accurate and interpretable model for siRNA efficacy prediction," BMC Bioinformatics, 7:520 (2006).
Vila-Aiub et al., "Glyphosate resistance in perennial *Sorghum halepense* (Johnsongrass), endowed by reduced glyphosate translocation and leaf uptake," Pest Manag Sci, 68:430-436 (2012).
Voinnet et al., "Systemic Spread of Sequence-Specific Transgene RNA Degradation in Plants is Initiated by Localized Introduction of Ectopic Promoterless DNA," Cell, 95:177-187 (1998).
Voinnet, "Origin, Biogenesis, and Activity of Plant MicroRNAs," Cell, 136:669-687 (2009).
Wakelin et al., "A target-site mutation is present in a glyphosate-resistant Lolium rigidum population," Weed Res. (Oxford), 46(5):432-440 (2006).
Walton et al., "Prediction of antisense oligonucleotide binding affinity to a structured RNA target," Biotechnol Bioeng 65(1):1-9 (1999).

(56) References Cited

OTHER PUBLICATIONS

Wan et al., "Generation of Large Numbers of Independently Transformed Fertile Barley Plants," Plant Physiol., 104:37-48 (1994).
Wang et al., "Foliar uptake of pesticides—Present status and future challenge," ScienceDirect, 87:1-8 (2007).
Wang et al., "Principle and technology of genetic engineering in plants," in Plant genetic engineering principles and techniques, Beijing: Science Press, pp. 313-315 (1998).
Wardell, "Floral Induction of Vegetative Plants Supplied a Purified Fraction of Deoxyribonucleic Acid from Stems of Flowering Plants," Plant Physiol, 60:885-891 (1977).
Wardell, "Floral Activity in Solutions of Deoxyribonucleic Acid Extracted from Tobacco Stems," Plant Physiol, 57:855-861 (1976).
Waterhouse et al., "Virus resistance and gene silencing in plants can be induced by simultaneous expression of sense and antisense RNA," Proc Natl Acad Sci USA, 95 13959-13964 (1998).
Watson et al., "RNA silencing platforms in plants," FEBS Letters, 579:5982-5987 (2005).
Welch et al., "Expression of ribozymes in gene transfer systems to modulate target RNA levels," Curr Opin Biotechnol. 9(5):486-496 (1998).
Widholm et al., "Glyphosate selection of gene amplification in suspension cultures of 3 plant species," Phyisologia Plantarum, 112:540-545 (2001).
Wiesman et al., "Novel cationic vesicle platform derived from vernonia oil for efficient delivery of DNA through plant cuticle membranes," Journal of Biotechnology, 130:85-94 (2007).
Wild Carrot Noxious Weed Control Board (NWCB) of Washington State (2010) <www.nwcb.wa.gov/detail.asp?weed=46>.
Wilson, et al., "Transcription termination at intrinsic terminators: The role of the RNA hairpin," Proc. Natl. Acad. Sci. USA, 92:8793-8797 (1995).
Winkler et al., "Thiamine derivatives bind messenger RNAs directly to regulate bacterial gene expression," Nature, 419:952-956 (2002).
Wool et al., "Structure and evolution of mammalian ribosomal proteins," Biochem. Cell Biol., 73:933-947 (1995).
Written Opinion dated Apr. 7, 2016, in Singapore Patent Application No. 201206152-9.
Written Opinion dated Mar. 6, 2017, in Singaporean Patent Application No. 2012061529.
Written Opinion dated May 8, 2014, in International Application No. PCT/IL2013/050447.
Written Opinion dated Sep. 1, 2014, in Singapore Patent Application No. 201206152-9.
Xu et al., "Characterization and Functional Analysis of the Calmodulin-Binding Domain of Rac1 GTPase," PLoS One, 7(8):e42975 (2012).
Yan et al., Seed Science, China Agriculture Press, pp. 101-103, Tables 2-37 (2001).
Yin et al., "Production of double-stranded RNA for interference with TMV infection utilizing a bacterial prokaryotic expression system," Appl. Microbiol. Biotechnol., 84(2):323-333 (2009).
YouTube video by General Electric Company "Silwet Surfactants," screen shot taken on Jan. 11, 2012 of video of www.youtube.com/watch?v=WBw7nXMqHk8 (uploaded Jul. 13, 2009).
Yu et al., "Diversity of Acetyl-Coenzyme A Carboxylase Mutations in Resistant Lolium Populations: Evaluation Using Clethodim," Plant Physiology, 145:547-558 (2007).
Yu et al., "Glyphosate, paraquat and ACCase multiple herbicide resistance evolved in a Lolium rigidum biotype," Planta, 225:499-513 (2007).
Zabkiewicz, "Adjuvants and herbicidal efficacy—present status and future prospects," Weed Research, 40:139-149 (2000).
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," PNAS, 98(12):6617-6622 (2001).

Zhang et al., "Development and Validation of Endogenous Reference Genes for Expression Profiling of Medaka (*Oryzias latipes*) Exposed to Endocrine Disrupting Chemicals by Quantitative Real-Time RT-PCR," Toxicological Sciences, 95(2):356-368 (2007).
Zhang et al., "Progress in research of honey bee mite Varro destructor," Journal of Environmental Entomology, 34(3):345-353 (2012).
Zhang et al., "A novel rice gene, NRR responds to macronutrient deficiency and regulates root growth," Mol Plant, 5(1):63-72 (2012).
Zhang et al., "Agrobacterium-mediated transformation of *Arabidopsis thaliana* using the floral dip method," Nature Protocols, 1(2):1-6 (2006).
Zhang et al., "Cationic lipids and polymers mediated vectors for delivery of siRNA," Journal of Controlled Release, 123:1-10 (2007).
Zhang et al., "DEG: a database of essential genes," Nucleic Acids Res., 32:D271-D272 (2004).
Zhang et al., "Transgenic rice plants produced by electroporation-mediated plasmid uptake into protoplasts," The Plant Cell Rep., 7:379-384 (1988).
Zhang, "Artificial trans-acting small interfering RNA: a tool for plant biology study and crop improvements," Planta, 239:1139-1146 (2014).
Zhang, Chapter 10: New Characteristics of Pesticide Research & Development, p. 209 (2010).
Zhao et al., "PsOr1, a potential target for RNA interference based pest management," Insect Molecular Biology, 20(1):97-104 (2011).
Zhao et al., "Phyllotreta striolata (Coleoptera: Chrysomelidae):Arginine kinase cloning and RNAi-based pest control," European Journal of Entomology, 105(5):815-822 (2008).
Zhao et al., "Vegetable Statdardized Production Technology," Hangzhou: Zhejiang Science and Technology Press, p. 19 (2008).
Zhong et al., "A forward genetic screen to explore chloroplast protein import in vivo identifies Moco sulfurase, pivotal for ABA and IAA biosynthesis and purine turnover," The Plant Journal, 63:44-59 (2010).
Zhong et al., "A pea antisense gene for the chloroplast stromal processing peptidase yields seedling lethals in *Arabidopsis*: survivors show defective GFP import in vivo," The Plant Journal, 34:802-812 (2003).
Zhu et al., "Ingested RNA interference for managing the populations of the Colorado potato beetle, Leptinotarsa decemlineata," Pest Manag Sci, 67:175-182 (2010).
Zidack et al., "Promotion of Bacterial Infection of Leaves by an Organosilicone Surfactant: Implications for Biological Weed Control," Biological Control, 2:111-117 (1992).
Zipperian et al., "Silicon Carbide Abrasive Grinding," Quality Matters Newsletter, PACE Technologies 1(2):1-3 (2002).
Zotti et al., "RNAi technology for insect management and protection of beneficial insects from diseases: lessons, challenges and risk assessments," Neotropical Entomology, 44(3):197-213 (2015).
Bragiere et al., "Glutamine Synthetase in the Phloem Plays a Major Role in Controlling Praline Production," *The Plant Cell*, 11:195-2011 (1999).
Chang et al., "Dual-target gene silencing by using long, synthetic siRNA duplexes without triggeriing antiviral responses," *Molecules and Cells*, 27(6):689-695 (2009).
Communication pursuant to Article 94(3) EPC dated Mar. 16, 2020, in European Patent Application No. 17194281.6.
Communication pursuant to Article 94(3) EPC dated Mar. 27, 2020, in European Patent Application No. 15811092.4.
Cong et al., "Multiplex Genome Engineering Using CRISPR/Cas Systems," *Science*, 339:819-823 (2013).
Danka et al., "Field Test of Resistance to Acarapis wood: (Acari: Tarsonemidae) and of Colony Production by Four Stocks of Honey Bees (Hymenoptera: Apidae)" *Journal of Economic Entomology*, 88(3):584-591 (1995).
Decision to Grant dated Feb. 24, 2020, in Ukrainian Patent Application No. a 2016 08743 (with English language translation).
Declaration of Professor Robert James Henry executed Mar. 1, 2018, as filed by Applicant in Australian Patent Application No. 2014262189, pp. 1-119.

(56) References Cited

OTHER PUBLICATIONS

Downey et al., "Single and dual parasitic mite infestations on the honey bee, Apis mellifera L.," *Inserter Sociaux*, 47(2):171-176 (2000).

Drobyazko R.V., "Reliable and environmentally Friendly insecticide," Protection and quarantine of plants, pp. 52, 53 (2012) (with English language translations).

Extended European Search Report dated Mar. 25, 2020, in European Patent Application No. 19192942.1.

Hörmann et al., "Tic32, as Essential Component in Chloroplast Biogenesis," *The Journal of Biological Chemistry*, 279(33):34756-34762 (2004).

Hwa et al., "Fixation of hybrid vigor in rice: opportunities and challenges," *Euphytica*, 160:287-293 (2008).

Jasieniuk et al., "Glyphosate-Resistant Italian Ryegrass (*Lotium multiflorum*) in California: Distribution, Response to Glyphosate, and Molecular Evidence for an Altered Target Enzyme," *Weed Science*, 56(4):496-502 (2008).

Khanbekova et al., The defeat of the honey bee alis melifera caucasica Gorb. By viruses and parasites, and condition of bee colonies in different geographical conditions of Greater Caucasus, *Agricultural Biology*. 2013 (p. 43) (with English language translations).

Office Action dated Feb. 20, 2020, in Canadian Patent Application No. 2,905,104.

Office Action dated Feb. 25, 2020, in Japanese Patent Application No. 2017-538699 (with English language translation).

Ossowski et al., "Gene silencing in plants using artificial microRNAs and other small RNAs," *The Plant Journal*, 53:674-690 (2008).

Partial European Search Report dated Dec. 6, 2019, in European Patent Application No. 19185431.4.

Prado et al., "Design and optimization of degenerated universal primers for the cloing of the plant acetolactate synthase conserved domains," *Weed Science*, 52:487-491 (2004).

Reverdatto et al., "A Multisubunit Acetyl Coenzyme A Carboxylase from Soybean," *Plant Physiol.*, 119:961-978 (1999).

Sammataro et al., "Some Volatile Plant Oils as Potential Control Agents for Varroa Mites (Acari: Varroidae) in Honey Bee Colonies (Hymenoptera: Apidae)," *American Bee Journal*, 138(9):681-685 (1998).

Subramoni et al., "Lipases as Pathogenicity Factors of Plant Pathogens," *Handbook of Hydrocarbon and Lipid Microbiology*, 3269-3277 (2010).

Walton, "Deconstructing the Cell Wall," *Plant Physiol.*, 104:1113-1118 (1994).

Wang et al., "Principle and technology of genetic engineering in plants," in Plant genetic engineering principles and techniques, Beijing: Science Press, p. 313-315 (1998).

Yibrah et al., "Antisense RNA inhibition of uidA gene expression in transgenic plants: Evidence for interaction between first and second transformation events," *Hereditas*, 118:273-280 (1993).

\* cited by examiner

COMPOSITIONS AND METHODS FOR DELIVERY OF A POLYNUCLEOTIDE INTO A PLANT

CROSS-REFERENCE TO RELATED APPLICATIONS

This application is a U.S. National Stage of International Application No. PCT/US2016/035435, filed Jun. 2, 2016, which claims benefit of U.S. Provisional Application No. 62/170,002, filed Jun. 2, 2015, and U.S. Provisional Application No. 62/170,447, filed Jun. 3, 2015, all of which are incorporated by reference in their entirety herein.

FIELD

The present disclosure provides compositions and methods for delivering a polynucleotide from the exterior surface of a plant or plant part into the interior of a plant cell.

BACKGROUND

Gene suppression mediated by RNA interference has been developed as a potent tool for silencing genes in a broad range of organisms. There is however a need for compositions and methods to effectively deliver interfering RNAs used for topical application in plants, especially through the multiple protective barriers into the interior of the plant cell.

BRIEF SUMMARY

Several embodiments relate to a composition for delivering a polynucleotide from the exterior surface of a plant or plant part into the interior of a plant cell, comprising at least one polynucleotide and at least one agent that is able to disrupt at least one barrier of said plant or plant part. In some embodiments, the agent comprises one or more of an enzyme and an abrasive. In some embodiments, the enzyme is a hydrolytic enzyme. In some embodiments, the agent comprises more than one enzyme. In some embodiments, the enzyme is selected from the group consisting of cellulase, hemicellulase, pectinase, cutinase, and lipase. In some embodiments, the composition further comprises one or more of an osmolyte and a surfactant. In some embodiments, the composition comprises a polynucleotide and an enzyme. In some embodiments, the composition comprises a polynucleotide, an enzyme and an osmolyte. In some embodiments, the composition comprises a polynucleotide, an enzyme and a surfactant. In some embodiments, the composition comprises a polynucleotide, an enzyme, an osmolyte and a surfactant. In some embodiments, the composition comprises a polynucleotide and an abrasive. In some embodiments, the composition comprises a polynucleotide, an abrasive and an osmolyte. In some embodiments, the composition comprises a polynucleotide, an abrasive and a surfactant. In some embodiments, the composition comprises a polynucleotide, an abrasive, an osmolyte and a surfactant. In some embodiments, the composition comprises a polynucleotide, an abrasive and an enzyme. In some embodiments, the composition comprises a polynucleotide, an enzyme, an abrasive and an osmolyte. In some embodiments, the composition comprises a polynucleotide, an enzyme, an abrasive and a surfactant. In some embodiments, the composition comprises a polynucleotide, an enzyme, an abrasive, an osmolyte and a surfactant. In some embodiments, the polynucleotide is non-transcribable. In some embodiments, the non-transcribable polynucleotide is a trigger polynucleotide. In some embodiments, the polynucleotide is selected from the group consisting of single stranded DNA, single stranded RNA, double stranded DNA, double stranded RNA, and an RNA/DNA hybrid. In some embodiments, the polynucleotide is an interfering RNA. In some embodiments, the polynucleotide is a miRNA. In some embodiments, the polynucleotide is an mRNA. In some embodiments the polynucleotide is transcribable. In some embodiments, the polynucleotide encodes a CRISPR enzyme. In some embodiments, the polynucleotide comprises RNA components of a CRISPR system. In some embodiments, the polynucleotide comprises one or more of a guide sequence capable of hybridizing to a target sequence, a tracr mate sequence, and a tracr sequence. In some embodiments, the plant cell expresses a CRISPR enzyme. In some embodiments, the CRISPR enzyme is selected from the group consisting of Cas9, Cpf1, Csc1 and Csc2.

Several embodiments relate to a composition for delivering a polynucleotide from the exterior surface of a plant or plant part into the interior of a plant cell, comprising at least one polynucleotide and at least one enzyme that is able to disrupt at least one barrier of said plant or plant part. In some embodiments, the enzyme is a hydrolytic enzyme. In some embodiments, the at least one enzyme is independently selected from the group consisting of cellulase, hemicellulase, pectinase, cutinase, and lipase. In some embodiments, the composition further comprises one or more of an osmolyte and a surfactant. In some embodiments, the composition comprises a polynucleotide, an enzyme and an osmolyte. In some embodiments, the composition comprises a polynucleotide, an enzyme and a surfactant. In some embodiments, the composition comprises a polynucleotide, an enzyme, an osmolyte and a surfactant. In some embodiments, the exterior surface of the plant or plant part is abraded prior to applying the composition. In some embodiments, the exterior surface of the plant or plant part is abraded after applying the composition. In some embodiments, the polynucleotide is non-transcribable. In some embodiments, the non-transcribable polynucleotide is a trigger polynucleotide. In some embodiments, the polynucleotide is selected from the group consisting of single stranded DNA, single stranded RNA, double stranded DNA, double stranded RNA, and an RNA/DNA hybrid. In some embodiments, the polynucleotide is an interfering RNA. In some embodiments, the polynucleotide is a miRNA. In some embodiments, the polynucleotide is an mRNA. In some embodiments the polynucleotide is transcribable. In some embodiments, the polynucleotide encodes a CRISPR enzyme. In some embodiments, the polynucleotide comprises RNA components of a CRISPR system. In some embodiments, the polynucleotide comprises one or more of a guide sequence capable of hybridizing to a target sequence, a tracr mate sequence, and a tracr sequence. In some embodiments, the plant cell expresses a CRISPR enzyme. In some embodiments, the CRISPR enzyme is selected from the group consisting of Cas9, Cpf1, Csc1 and Csc2.

Several embodiments to a composition for delivering a polynucleotide from the exterior surface of a plant or plant part into the interior of a plant cell, comprising at least one polynucleotide, an osmolyte and at least one surfactant. In some embodiments, the exterior surface of the plant or plant part is abraded prior to applying the composition. In some embodiments, the exterior surface of the plant or plant part is abraded after applying the composition. In some embodiments, the polynucleotide is non-transcribable. In some embodiments, the non-transcribable polynucleotide is a trigger polynucleotide. In some embodiments, the polynucleotide is selected from the group consisting of single stranded DNA, single stranded RNA, double stranded DNA, double stranded RNA, and an RNA/DNA hybrid. In some embodiments, the polynucleotide is an interfering RNA. In some embodiments, the polynucleotide is a miRNA. In some embodiments, the polynucleotide is an mRNA. In some embodiments the polynucleotide is transcribable. In some embodiments, the polynucleotide encodes a CRISPR enzyme. In some embodiments, the polynucleotide comprises RNA components of a CRISPR system. In some embodiments, the polynucleotide comprises one or more of a guide sequence capable of hybridizing to a target sequence, a tracr mate sequence, and a tracr sequence. In some embodiments, the plant cell expresses a CRISPR enzyme. In some embodiments, the CRISPR enzyme is selected from the group consisting of Cas9, Cpf1, Csc1 and Csc2.

Several embodiments relate to a method for delivering a polynucleotide from the exterior surface of a plant or plant part into the interior of a plant cell, comprising applying to the exterior surface of said plant or plant part at least one polynucleotide and at least one agent that is able to disrupt at least one barrier of said plant or plant part. In some embodiments, the polynucleotide and agent are applied by spraying. In some embodiments, the agent comprises one or more of an enzyme and an abrasive. In some embodiments, the enzyme is a hydrolytic enzyme. In some embodiments, the agent comprises more than one enzyme. In some embodiments, the enzyme is selected from the group consisting of cellulase, hemicellulase, pectinase, cutinase, and lipase. In some embodiments, the method further comprises applying to the exterior surface of said plant or plant part one or more of an osmolyte and a surfactant. In some embodiments, the method comprises applying the agent and the polynucleotide in a single composition. In some embodiments, the method comprises applying the agent and the polynucleotide separately. In some embodiments, the method comprises applying one or more of the osmolyte and the surfactant with the polynucleotide. In some embodiments, the method comprises applying one or more of the osmolyte and the surfactant with the agent. In some embodiments, the method comprises applying the polynucleotide, the agent and one or more of the osmolyte and the surfactant in a single composition. In some embodiments, the polynucleotide is non-transcribable. In some embodiments, the non-transcribable polynucleotide is a trigger polynucleotide. In some embodiments, the polynucleotide is selected from the group consisting of single stranded DNA, single stranded RNA, double stranded DNA, double stranded RNA, and an RNA/DNA hybrid. In some embodiments, the polynucleotide is an interfering RNA. In some embodiments, the polynucleotide is a miRNA. In some embodiments, the polynucleotide is an mRNA. In some embodiments the polynucleotide is transcribable. In some embodiments, the polynucleotide encodes a CRISPR enzyme. In some embodiments, the polynucleotide comprises RNA components of a CRISPR system. In some embodiments, the polynucleotide comprises one or more of a guide sequence capable of hybridizing to a target sequence, a tracr mate sequence, and a tracr sequence. In some embodiments, the plant cell expresses a CRISPR enzyme. In some embodiments, the CRISPR enzyme is selected from the group consisting of Cas9, Cpf1, Csc1 and Csc2.

Several embodiments relate to a method for delivering a polynucleotide from the exterior surface of a plant or plant part into the interior of a plant cell, comprising applying to the exterior surface of said plant or plant part at least one polynucleotide and at least one enzyme that is able to disrupt at least one barrier of said plant or plant part. In some embodiments, the polynucleotide and enzyme are applied by spraying. In some embodiments, the exterior surface of the plant or plant part is abraded prior to applying the polynucleotide and the enzyme. In some embodiments, the exterior surface of the plant or plant part is abraded after applying the polynucleotide and the enzyme. In some embodiments, the enzyme is a hydrolytic enzyme. In some embodiments, the at least one enzyme is selected independently from the group consisting of cellulase, hemicellulase, pectinase, cutinase, and lipase. In some embodiments, the method further comprises applying to the exterior surface of said plant or plant part one or more of an osmolyte and a surfactant. In some embodiments, the method comprises applying the enzyme and the polynucleotide in a single composition. In some embodiments, the method comprises applying the enzyme and the polynucleotide separately. In some embodiments, the method comprises applying one or more of the osmolyte and the surfactant with the polynucleotide. In some embodiments, the method comprises applying one or more of the osmolyte and the surfactant with the enzyme. In some embodiments, the method comprises applying the polynucleotide, the enzyme and one or more of the osmolyte and the surfactant in a single composition. In some embodiments, the polynucleotide is non-transcribable. In some embodiments, the non-transcribable polynucleotide is a trigger polynucleotide. In some embodiments, the polynucleotide is selected from the group consisting of single stranded DNA, single stranded RNA, double stranded DNA, double stranded RNA, and an RNA/DNA hybrid. In some embodiments, the polynucleotide is an interfering RNA. In some embodiments, the polynucleotide is a miRNA. In some embodiments, the polynucleotide is an mRNA. In some embodiments the polynucleotide is transcribable. In some embodiments, the polynucleotide encodes a CRISPR enzyme. In some embodiments, the polynucleotide comprises RNA components of a CRISPR system. In some embodiments, the polynucleotide comprises one or more of a guide sequence capable of hybridizing to a target sequence, a tracr mate sequence, and a tracr sequence. In some embodiments, the plant cell expresses a CRISPR enzyme. In some embodiments, the CRISPR enzyme is selected from the group consisting of Cas9, Cpf1, Csc1 and Csc2.

Several embodiments relate to a method for delivering a polynucleotide from the exterior surface of a plant or plant part into the interior of a plant cell, comprising applying to the exterior surface of said plant or plant part at least one polynucleotide, an osmolyte and at least one surfactant. In some embodiments, the polynucleotide, osmolyte and surfactant are applied by spraying. In some embodiments, the method further comprises abrading the exterior surface of the plant or plant part prior to applying the polynucleotide, osmolyte and surfactant. In some embodiments, the method further comprises abrading the exterior surface of the plant or plant part after applying the polynucleotide, osmolyte and surfactant. In some embodiments, the method comprises applying the osmolytes and surfactant with the polynucleotide. In some embodiments, the polynucleotide is non-transcribable. In some embodiments, the non-transcribable polynucleotide is a trigger polynucleotide. In some embodiments, the polynucleotide is selected from the group consisting of single stranded DNA, single stranded RNA, double stranded DNA, double stranded RNA, and an RNA/DNA hybrid. In some embodiments, the polynucleotide is an interfering RNA. In some embodiments, the polynucleotide is a miRNA. In some embodiments, the polynucleotide is an mRNA. In some embodiments the polynucleotide is transcribable. In some embodiments, the polynucleotide encodes a CRISPR enzyme. In some embodiments, the polynucleotide comprises one or more RNA components of a CRISPR system. In some embodiments, the polynucleotide comprises one or more of a guide sequence capable of hybridizing to a target sequence, a tracr mate sequence, and a tracr sequence. In some embodiments, the plant cell expresses a CRISPR enzyme. In some embodiments, the CRISPR enzyme is selected from the group consisting of Cas9, Cpf1, Csc1 and Csc2.

Several embodiments relate to a method for delivering a polynucleotide from the exterior surface of a plant or plant part into the interior of a plant cell, comprising abrading the surface of said plant or plant part and topically applying onto said surface at least one polynucleotide. In some embodiments, the at least one polynucleotide is applied by spraying. In some embodiments, the method further comprises applying to the exterior surface of said plant or plant part one or more of an osmolyte and a surfactant. In some embodiments, the at least one polynucleotide, and one or more of the osmolyte and surfactant are applied by spraying. In some embodiments, the polynucleotide is non-transcribable. In some embodiments, the non-transcribable polynucleotide is a trigger polynucleotide. In some embodiments, the polynucleotide is selected from the group consisting of single stranded DNA, single stranded RNA, double stranded DNA, double stranded RNA, and an RNA/DNA hybrid. In some embodiments, the polynucleotide is an interfering RNA. In some embodiments, the polynucleotide is a miRNA. In some embodiments, the polynucleotide is an mRNA. In some embodiments, the polynucleotide is transcribable. In some embodiments, the polynucleotide encodes a CRISPR enzyme. In some embodiments, the polynucleotide comprises one or more RNA components of a CRISPR system. In some embodiments, the polynucleotide comprises one or more of a guide sequence capable of hybridizing to a target sequence, a tracr mate sequence, and a tracr sequence. In some embodiments, the plant cell expresses a CRISPR enzyme. In some embodiments, the CRISPR enzyme is selected from the group consisting of Cas9, Cpf1, Csc1 and Csc2.

Several embodiments relate to an herbicidal composition adapted for topical application onto an exterior surface of a weed or a volunteer plant, the composition comprising: at least one non-transcribable polynucleotide and at least one agent that is able to disrupt at least one barrier of said weed or volunteer plant, wherein said at least one non-transcribable polynucleotide comprises a sequence essentially identical or essentially complementary to a coding or non-coding sequence of an endogenous gene of said weed or volunteer plant or a messenger RNA that is transcribed from an endogenous gene of said weed or volunteer plant; and wherein said endogenous gene: (i) is an essential gene for maintaining the growth or life of said weed or volunteer plant, (ii) encodes a protein that provides herbicide resistance to said weed or volunteer plant, or (iii) transcribes to an RNA regulatory agent. In some embodiments, the herbicidal composition is applied by spraying the herbicidal composition onto an exterior surface of a weed or a volunteer plant. In some embodiments, the agent comprises one or more of an enzyme and an abrasive. In some embodiments, the agent comprises more than one enzyme. In some embodiments, the enzyme is selected from the group consisting of cellulase, hemicellulase, pectinase, cutinase, and lipase. In some embodiments, the enzyme is a hydrolytic enzyme. In some embodiments, the herbicidal composition further comprises one or more of an osmolyte and a surfactant. In some embodiments, the herbicidal composition comprises at least one non-transcribable polynucleotide and an enzyme. In some embodiments, the herbicidal composition comprises at least one non-transcribable polynucleotide, an enzyme and an osmolyte. In some embodiments, the herbicidal composition comprises at least one non-transcribable polynucleotide, an enzyme and a surfactant. In some embodiments, the herbicidal composition comprises at least one non-transcribable polynucleotide, an enzyme, an osmolyte and a surfactant. In some embodiments, the herbicidal composition comprises at least one non-transcribable polynucleotide and an abrasive. In some embodiments, the herbicidal composition comprises at least one non-transcribable polynucleotide, an abrasive and an osmolyte. In some embodiments, the herbicidal composition comprises at least one non-transcribable polynucleotide, an abrasive and a surfactant. In some embodiments, the herbicidal composition comprises at least one non-transcribable polynucleotide, an abrasive, an osmolyte and a surfactant. In some embodiments, the herbicidal composition comprises at least one non-transcribable polynucleotide, an abrasive and an enzyme. In some embodiments, the herbicidal composition comprises at least one non-transcribable polynucleotide, an enzyme, an abrasive and an osmolyte. In some embodiments, the herbicidal composition comprises at least one non-transcribable polynucleotide, an enzyme, an abrasive and a surfactant. In some embodiments, the herbicidal composition comprises at least one non-transcribable polynucleotide, an enzyme, an abrasive, an osmolyte and a surfactant. In some embodiments, the non-transcribable polynucleotide is a trigger polynucleotide. In some embodiments, the non-transcribable polynucleotide is selected from the group consisting of single stranded DNA, single stranded RNA, double stranded DNA, double stranded RNA, and an RNA/DNA hybrid. In some embodiments, the polynucleotide is an interfering RNA. In some embodiments, the polynucleotide is a miRNA.

Several embodiments relate to a herbicidal composition adapted for topical application onto an exterior surface of a weed or a volunteer plant, the composition comprising at least one non-transcribable polynucleotide polynucleotide and at least one enzyme that is able to disrupt at least one barrier of said weed or volunteer plant, wherein said at least one non-transcribable polynucleotide comprises a sequence essentially identical or essentially complementary to a coding or non-coding sequence of an endogenous gene of said weed or volunteer plant or a messenger RNA that is transcribed from an endogenous gene of said weed or volunteer plant; and wherein said endogenous gene: (i) is an essential gene for maintaining the growth or life of said weed or volunteer plant, (ii) encodes a protein that provides herbicide resistance to said weed or volunteer plant, or (iii) transcribes to an RNA regulatory agent. In some embodiments, the herbicidal composition is applied by spraying the herbicidal composition onto an exterior surface of a weed or a volunteer plant. In some embodiments, the enzyme is a hydrolytic enzyme. In some embodiments, the at least one enzyme is independently selected from the group consisting of cellulase, hemicellulase, pectinase, cutinase, and lipase. In some embodiments, the herbicidal composition further comprises one or more of an osmolyte and a surfactant. In some embodiments, the herbicidal composition comprises a non-transcribable polynucleotide, an enzyme and an osmolyte. In some embodiments, the herbicidal composition comprises a polynucleotide, an enzyme and a surfactant. In some embodiments, the herbicidal composition comprises a non-transcribable polynucleotide, an enzyme, an osmolyte and a surfactant. In some embodiments, the exterior surface of the weed or volunteer plant is abraded prior to applying the composition. In some embodiments, the exterior surface of the weed or volunteer part is abraded after applying the composition. In some embodiments, the non-transcribable polynucleotide is a trigger polynucleotide. In some embodiments, the non-transcribable polynucleotide is selected from the group consisting of single stranded DNA, single stranded RNA, double stranded DNA, double stranded RNA, and an RNA/DNA hybrid. In some embodiments, the non-transcribable polynucleotide is an interfering RNA. In some embodiments, the non-transcribable polynucleotide is a miRNA.

Several embodiments to a herbicidal composition adapted for topical application onto an exterior surface of a weed or a volunteer plant, the composition comprising: at least one non-transcribable polynucleotide, an osmolyte and at least one surfactant, wherein said at least one non-transcribable polynucleotide comprises a sequence essentially identical or essentially complementary to a coding or non-coding sequence of an endogenous gene of said weed or volunteer plant or a messenger RNA that is transcribed from an endogenous gene of said weed or volunteer plant; and wherein said endogenous gene: (i) is an essential gene for maintaining the growth or life of said weed or volunteer plant, (ii) encodes a protein that provides herbicide resistance to said weed or volunteer plant, or (iii) transcribes to an RNA regulatory agent. In some embodiments, the herbicidal composition is applied by spraying the herbicidal composition onto an exterior surface of a weed or a volunteer plant. In some embodiments, the exterior surface of the plant or plant part is abraded prior to applying the herbicidal composition. In some embodiments, the exterior surface of the plant or plant part is abraded after applying the herbicidal composition. In some embodiments, the non-transcribable polynucleotide is a trigger polynucleotide. In some embodiments, the non-transcribable polynucleotide is selected from the group consisting of single stranded DNA, single stranded RNA, double stranded DNA, double stranded RNA, and an RNA/DNA hybrid. In some embodiments, the non-transcribable polynucleotide is an interfering RNA. In some embodiments, the non-transcribable polynucleotide is a miRNA.

Several embodiments relate to a method for selectively controlling a targeted herbicide-resistant weed or volunteer plant comprising topically applying onto a surface of said weed or volunteer plant at least one non-transcribable polynucleotide and at least one agent that is able to disrupt at least one barrier of said weed or volunteer plant; wherein said at least one non-transcribable polynucleotide comprises a sequence essentially identical or essentially complementary to a coding or non-coding sequence of an endogenous gene of said weed or volunteer plant or a messenger RNA that is transcribed from an endogenous gene of said weed or volunteer plant; and wherein said endogenous gene: (i) is an essential gene for maintaining the growth or life of said weed or volunteer plant, (ii) encodes a protein that provides herbicide resistance to said weed or volunteer plant, or (iii) transcribes to an RNA regulatory agent. In some embodiments, the non-transcribable polynucleotide and agent are applied by spraying. In some embodiments, the agent comprises one or more of an enzyme and an abrasive. In some embodiments, the agent comprises more than one enzyme. In some embodiments, the enzyme is selected from the group consisting of cellulase, hemicellulase, pectinase, cutinase, and lipase. In some embodiments, the enzyme is a hydrolytic enzyme. In some embodiments, the method further comprises applying to the exterior surface of said plant or plant part one or more of an osmolyte and a surfactant. In some embodiments, the method comprises applying the agent and at least one non-transcribable polynucleotide in a single composition. In some embodiments, the method comprises applying the agent and at least one non-transcribable polynucleotide separately. In some embodiments, the method comprises applying one or more of the osmolyte and the surfactant with at least one non-transcribable polynucleotide. In some embodiments, the method comprises applying one or more of the osmolyte and the surfactant with the agent. In some embodiments, the method comprises applying the non-transcribable polynucleotide, the agent and one or more of the osmolyte and the surfactant in a single composition. In some embodiments, the non-transcribable polynucleotide is a trigger polynucleotide.

Several embodiments relate to a method for selectively controlling a targeted herbicide-resistant weed or volunteer plant comprising topically applying onto a surface of said weed or volunteer plant at least one non-transcribable polynucleotide and at least one enzyme that is able to disrupt at least one barrier of said weed or volunteer plant; wherein said at least one non-transcribable polynucleotide comprises a sequence essentially identical or essentially complementary to a coding or non-coding sequence of an endogenous gene of said weed or volunteer plant or a messenger RNA that is transcribed from an endogenous gene of said weed or volunteer plant; and wherein said endogenous gene: (i) is an essential gene for maintaining the growth or life of said weed or volunteer plant, (ii) encodes a protein that provides herbicide resistance to said weed or volunteer plant, or (iii) transcribes to an RNA regulatory agent. In some embodiments, the non-transcribable polynucleotide and enzyme are applied by spraying. In some embodiments, the exterior surface of the weed or volunteer plant is abraded prior to applying at least one non-transcribable polynucleotide and the enzyme. In some embodiments, the exterior surface of the weed or volunteer plant is abraded after applying at least one non-transcribable polynucleotide and the enzyme. In some embodiments, the enzyme is a hydrolytic enzyme. In some embodiments, the at least one enzyme is independently selected from the group consisting of cellulase, hemicellulase, pectinase, cutinase, and lipase. In some embodiments, the method further comprises applying to the exterior surface of said weed or volunteer plant one or more of an osmolyte and a surfactant. In some embodiments, the method comprises applying the enzyme and at least one non-transcribable polynucleotide in a single composition. In some embodiments, the method comprises applying the enzyme and at least one non-transcribable polynucleotide separately. In some embodiments, the method comprises applying one or more of the osmolyte and the surfactant with at least one non-transcribable polynucleotide. In some embodiments, the method comprises applying one or more of the osmolyte and the surfactant with the enzyme. In some embodiments, the method comprises applying at least one non-transcribable polynucleotide, the enzyme and one or more of the osmolyte and the surfactant in a single composition. In some embodiments, the non-transcribable polynucleotide is a trigger polynucleotide.

Several embodiments relate to a method for selectively controlling a targeted herbicide-resistant weed or volunteer plant comprising topically applying onto a surface of said weed or volunteer plant at least one non-transcribable polynucleotide, an osmolyte and a surfactant; wherein said at least one non-transcribable polynucleotide comprises a sequence essentially identical or essentially complementary to a coding or non-coding sequence of an endogenous gene of said weed or volunteer plant or a messenger RNA that is transcribed from an endogenous gene of said weed or volunteer plant; and wherein said endogenous gene: (i) is an essential gene for maintaining the growth or life of said weed or volunteer plant, (ii) encodes a protein that provides herbicide resistance to said weed or volunteer plant, or (iii) transcribes to an RNA regulatory agent. In some embodiments, the non-transcribable polynucleotide, osmolyte and surfactant are applied by spraying. In some embodiments, the exterior surface of the weed or volunteer plant is abraded prior to applying at least one non-transcribable polynucleotide, the osmolyte and the surfactant. In some embodiments, the exterior surface of the weed or volunteer plant is abraded after applying at least one non-transcribable polynucleotide, the osmolyte and the surfactant. In some embodiments, the method comprises applying the osmolyte, surfactant and at least one non-transcribable polynucleotide in a single composition. In some embodiments, the method comprises applying the surfactant and at least one non-transcribable polynucleotide separately. In some embodiments, the non-transcribable polynucleotide is a trigger polynucleotide.

Several embodiments relate to a method for selectively controlling a targeted herbicide-resistant weed or volunteer plant comprising abrading the surface of said weed or volunteer plant and topically applying onto said surface at least one non-transcribable polynucleotide; wherein said at least one non-transcribable polynucleotide comprises a sequence essentially identical or essentially complementary to a coding or non-coding sequence of an endogenous gene of said weed or volunteer plant or a messenger RNA that is transcribed from an endogenous gene of said weed or volunteer plant; and wherein said endogenous gene: (i) is an essential gene for maintaining the growth or life of said weed or volunteer plant, (ii) encodes a protein that provides herbicide resistance to said weed or volunteer plant, or (iii) transcribes to an RNA regulatory agent. In some embodiments, the method further comprises applying to the exterior surface of said weed or volunteer plant one or more of an osmolyte and a surfactant. In some embodiments, the polynucleotide, osmolyte and surfactant are applied by spraying. In some embodiments, the non-transcribable polynucleotide is a trigger polynucleotide.

Several embodiments relate to a method for delivering one or more elements of a CRISPR system from the exterior surface of a plant or plant part into the interior of a plant cell, comprising applying to the exterior surface of said plant or plant part at least one polynucleotide encoding one or more elements of the CRISPR system and at least one agent that is able to disrupt at least one barrier of said plant or plant part. In some embodiments, the plant cell expresses a Cas enzyme and the at least one polynucleotide encodes one or more RNA components of the CRISPR system. In some embodiments, the polynucleotide and agent are applied by spraying. In some embodiments, the agent comprises one or more of an enzyme and an abrasive. In some embodiments, the agent comprises more than one enzyme. In some embodiments, the enzyme is selected from the group consisting of cellulase, hemicellulase, pectinase, cutinase, and lipase. In some embodiments, the enzyme is a hydrolytic enzyme. In some embodiments, the method further comprises applying to the exterior surface of said plant or plant part one or more of an osmolyte and a surfactant. In some embodiments, the method comprises applying the agent and at least one polynucleotide encoding one or more elements of the CRISPR system in a single composition. In some embodiments, the method comprises applying the agent and at least one polynucleotide encoding one or more elements of the CRISPR system separately. In some embodiments, the method comprises applying one or more of the osmolyte and the surfactant with at least one polynucleotide encoding one or more elements of the CRISPR system. In some embodiments, the method comprises applying one or more of the osmolyte and the surfactant with the agent. In some embodiments, the method comprises applying the polynucleotide encoding one or more elements of the CRISPR system, the agent and one or more of the osmolyte and the surfactant in a single composition. In some embodiments, the polynucleotide encodes one or more of a Cas enzyme, a guide sequence, a tracr-mate sequence, and a tracr sequence. In some embodiments, the polynucleotide encodes a guide sequence linked to a tracr-mate sequence. In some embodiments, the Cas enzyme is selected from the group consisting of Cas9, Cpf1, Csc1 and Csc2.

Several embodiments relate to a method for delivering one or more elements of a CRISPR system from the exterior surface of a plant or plant part into the interior of a plant cell, comprising applying to the exterior surface of said plant or plant part at least one polynucleotide encoding one or more elements of the CRISPR system and at least one enzyme that is able to disrupt at least one barrier of said plant or plant part. In some embodiments, the plant cell expresses a Cas enzyme and the at least one polynucleotide encodes one or more RNA components of the CRISPR system. In some embodiments, the polynucleotide and agent are applied by spraying. In some embodiments, the exterior surface of the plant or plant part is abraded prior to applying the polynucleotide encoding one or more elements of the CRISPR system and the enzyme. In some embodiments, the exterior surface of the plant or plant part is abraded after applying the polynucleotide encoding one or more elements of the CRISPR system and the enzyme. In some embodiments, the enzyme is a hydrolytic enzyme. In some embodiments, the at least one enzyme is independently selected from the group consisting of cellulase, hemicellulase, pectinase, cutinase, and lipase. In some embodiments, the method further comprises applying to the exterior surface of said plant or plant part one or more of an osmolyte and a surfactant. In some embodiments, the method comprises applying the enzyme and at least one polynucleotide encoding one or more elements of the CRISPR system in a single composition. In some embodiments, the method comprises applying the enzyme and at least one polynucleotide encoding one or more elements of the CRISPR system separately. In some embodiments, the method comprises applying one or more of the osmolyte and the surfactant with at least one polynucleotide encoding one or more elements of the CRISPR system. In some embodiments, the method comprises applying one or more of the osmolyte and the surfactant with the enzyme. In some embodiments, the method comprises applying the polynucleotide encoding one or more elements of the CRISPR system, the enzyme and one or more of the osmolyte and the surfactant in a single composition. In some embodiments, the polynucleotide encodes one or more of a Cas enzyme, a guide sequence, a tracr-mate sequence, and a tracr sequence. In some embodiments, the polynucleotide encodes a guide sequence linked to a tracr-mate sequence. In some embodiments, the Cas enzyme is selected from the group consisting of Cas9, Cpf1, Csc1 and Csc2.

Several embodiments relate to a method for delivering one or more elements of a CRISPR system from the exterior surface of a plant or plant part into the interior of a plant cell, comprising applying to the exterior surface of said plant or plant part at least one polynucleotide encoding one or more elements of the CRISPR system, an osmolyte and a surfactant. In some embodiments, the plant cell expresses a Cas enzyme and the at least one polynucleotide encodes one or more RNA components of the CRISPR system. In some embodiments, the non-transcribable polynucleotide, osmolyte and surfactant are applied by spraying. In some embodiments, the exterior surface of the plant or plant part is abraded prior to applying the polynucleotide, the osmolyte and the surfactant. In some embodiments, the exterior surface of the weed or volunteer plant is abraded after applying the polynucleotide, the osmolyte and the surfactant. In some embodiments, the method comprises applying the osmolyte, surfactant and the polynucleotide in a single composition. In some embodiments, the method comprises applying the surfactant and the polynucleotide separately. In some embodiments, the polynucleotide encodes one or more of a Cas enzyme, a guide sequence, a tracr-mate sequence, and a tracr sequence. In some embodiments, the polynucleotide encodes a guide sequence linked to a tracr-mate sequence. In some embodiments, the Cas enzyme is selected from the group consisting of Cas9, Cpf1, Csc1 and Csc2.

Several embodiments relate to a method for delivering one or more elements of a CRISPR system from the exterior surface of a plant or plant part into the interior of a plant cell, comprising abrading the surface of said plant or plant part and topically applying onto said surface at least one polynucleotide encoding one or more elements of the CRISPR system. In some embodiments, the plant cell expresses a Cas enzyme and the at least one polynucleotide encodes one or more RNA components of the CRISPR system. In some embodiments, the at least one polynucleotide is applied by spraying. In some embodiments, the method further comprises applying to the exterior surface of said plant or plant part one or more of an osmolyte and a surfactant. In some embodiments, the at least one polynucleotide, and one or more of the osmolyte and surfactant are applied by spraying. In some embodiments, the polynucleotide encodes one or more of a Cas enzyme, a guide sequence, a tracr-mate sequence, and a tracr sequence. In some embodiments, the polynucleotide encodes a guide sequence linked to a tracr-mate sequence. In some embodiments, the Cas enzyme is selected from the group consisting of Cas9, Cpf1, Csc1 and Csc2.

DETAILED DESCRIPTION

Figure 1:
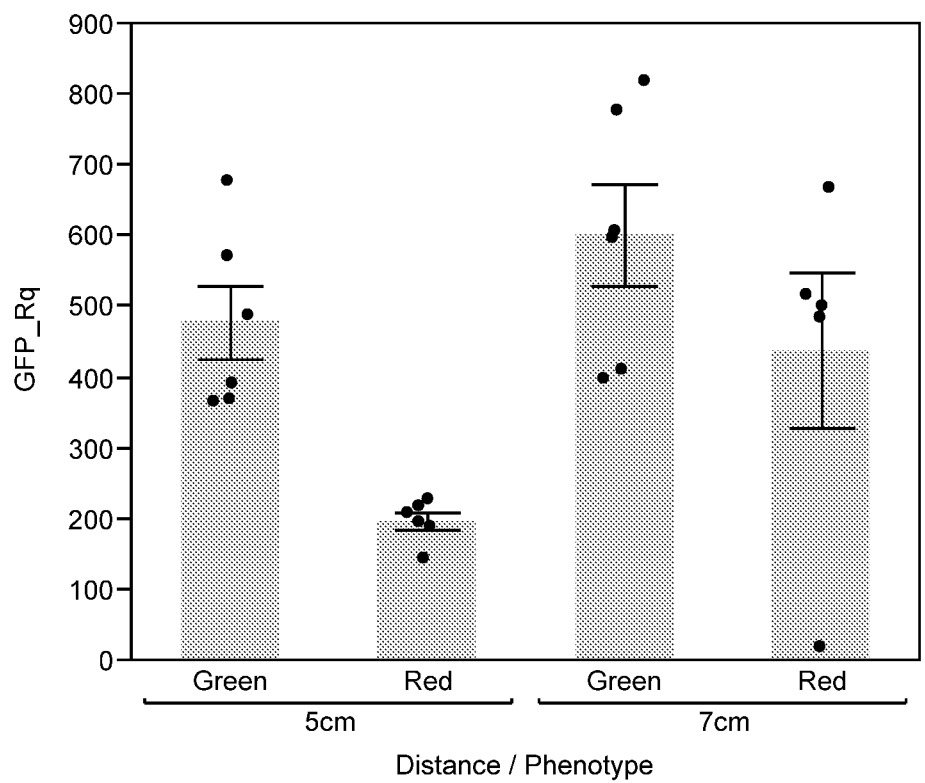
FIG. 1 depicts qPCR measurements of relative abundance of GFP mRNA, correlated to visual phenotype (see Example 28).
Figure 2:
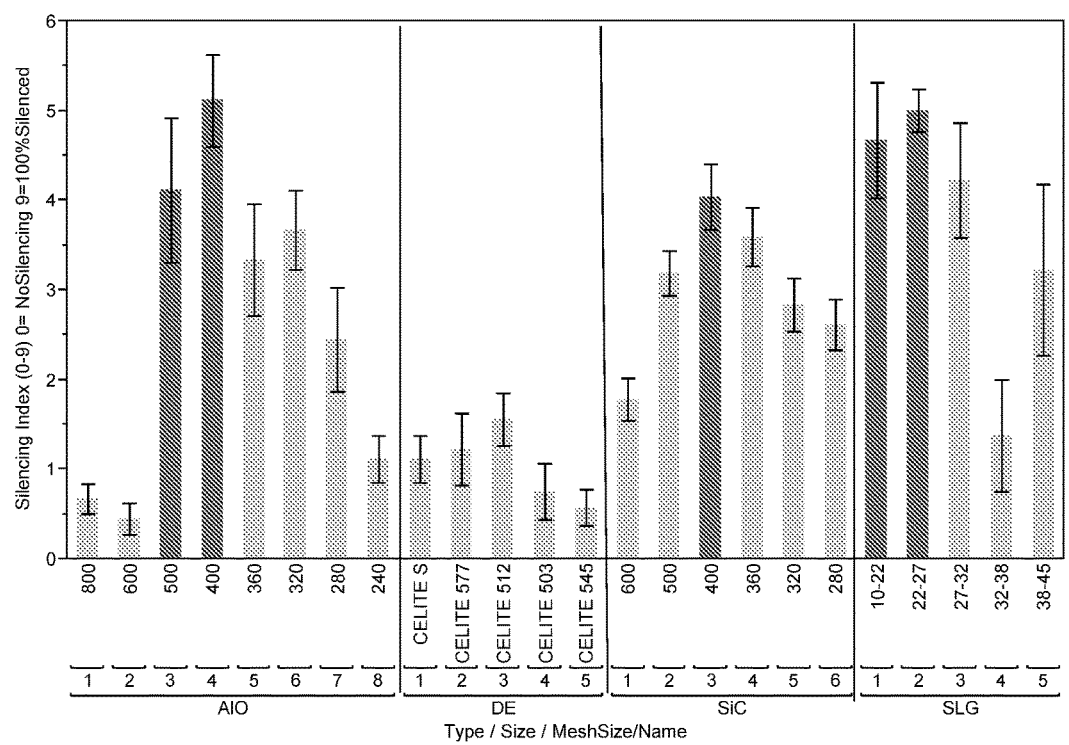
FIG. 2 depicts visual silencing efficacy for the different particulates tested, as described in Example 31. "A10"=aluminum oxide (listed by mesh size), "DE"=diatomaceous earth (listed as Celite grades), "SiC"=silicon carbide (listed by mesh size), "SLG"=soda lime glass (listed by bead diameter range in micrometers).

Unless defined otherwise, all technical and scientific terms used have the same meaning as commonly understood by one of ordinary skill in the art to which this disclosure belongs. Where a term is provided in the singular, the inventors also contemplate aspects described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York). The inventors do not intend to be limited to a mechanism or mode of action. Reference thereto is provided for illustrative purposes only.

Any references cited herein are incorporated by reference in their entireties.

As used herein, the singular form "a," "an," and "the" include plural references unless the context clearly dictates otherwise. For example, the term "a compound" or "at least one compound" may include a plurality of compounds, including mixtures thereof.

As used herein, the term "about" indicates that a value includes the inherent variation of error for the method being employed to determine a value, or the variation that exists among experiments.

Enzymes for Disrupting at Least One Barrier of the Plant Cell

As used herein, the term "enzyme" refers to a protein that is able to catalyze a specific biochemical reaction. As used herein, the term "at least one barrier" of a plant cell refers to the protective layers enclosing the cytoplasm of a plant protoplast, including plant cuticle/wax barrier, plant cell wall, plant plasma membrane, or any combination thereof. Therefore, the term "disrupt at least one barrier" means breaking down at least one component molecule in plant cuticle/wax barrier, plant cell wall, or plant plasma membrane.

In one embodiment, the enzyme is a protein that helps break down at least one component molecule in plant cuticle/wax barrier, plant cell wall, or plant plasma membrane. Examples of component molecules in plant cuticle/wax barrier, plant cell wall, or plant plasma membrane include, but are not limited to, polysaccharides (such as cellulose, hemicellulose and pectin), lipids (such as phospholipids and cutin), and glycopolypeptides. An enzyme can be classified by its substrate or the chemical reaction it catalyzes. The Enzyme Commission number (EC number) is a numerical classification scheme for enzymes based on the chemical reactions they catalyze. The enzyme unit (U) is a unit for the amount of a particular enzyme. One U is defined as the amount of the enzyme that produces a certain amount of enzymatic activity, that is, the amount that catalyzes the conversion of 1 micro mole of substrate per minute.

The enzymes can be derived from a natural biological source or produced recombinantly in a host cell. In one aspect, the enzyme is naturally or recombinantly produced by a microorganism. In some embodiments, the microorganism further produces a polynucleotide that induces an RNA interference (RNAi) response in a target plant. In another aspect, the enzyme is naturally or recombinantly produced by an animal or a plant. In some embodiments, the animal or a plant further produces a polynucleotide that induces an RNA interference (RNAi) response in a target plant. In some embodiments, the microorganism is a fungus. In some embodiments, the microorganism is a bacterium. Examples of microorganisms that can express an enzyme useful in the present disclosure include, but are not limited to, *Botrytis cinerea, Alternaria brassicola, Fusarium solani pisi, Fusarium graminearum, Thermomyces lanuginosus, Trichoderma viride, Myrothecium verrucaria, Phomopsis amaranthicola, Phytophtora cryptogea, Trichoderma viride, Trichoderma harzianum, Trichoderma bervicompactum.*

The enzyme can be used with or without any isolation or purification steps known in the art. In some embodiments, the enzyme is in a lyophilized form before being reconstituted for application. In some embodiments, the enzyme is provided in a liquid solution. In some embodiments, the enzyme is provided in a lyophilized form. In some embodiments, the enzyme is provided as part of a cell lysate. In some embodiments, the enzyme is provided as part of a cell culture broth. In some embodiments, the enzyme is provided as part of bacterial or fungal lysate.

As used herein, the term "cellulase" refers broadly to any enzyme that helps break down cellulose molecules, including a mixture of such enzymes, or any combination thereof. Examples of different cellulases based on the type of reaction catalyzed include, but are not limited to, endocellulases (EC 3.2.1.4), exocellulases or cellobiohydrolases (EC 3.2.1.91), cellobiases (EC 3.2.1.21) or beta-glucosidases, oxidative cellulases, and cellulose phosphorylases. Commercially available cellulases include, for example, those from fungi like *Aspergillus niger* and other *Aspergillus* sp., *Trichoderma viride* and other *Trichoderma* sp., like *Trichoderma reesei* ATCC 26921, *Trichoderma longibrachiatum* and *Trichoderma harzianum*, or bacteria like those from *Clostridium thermocellum* or Dyctioglomus turgid.

Similarly, as used herein, the term "hemicellulase" refers broadly to any enzyme that helps break down hemicellulose molecules, including a mixture of such enzymes, or any combination thereof. Non-limiting examples of hemicellulose include xylan, glucuronoxylan, arabinoxylan, glucomannan, and xyloglucan. Therefore, non-limiting examples of hemicellulase include xylanase, glucuronoxylanase, arabinoxylanase, glucomannanase, and xyloglucanase. Commercially available hemicellulases include, for example, those from fungi like *Aspergillus niger* and other *Aspergillus* sp., *Thermomyces lanuginosus, Trichoderma* sp. like *Trichoderma longibrachiatum* and *Trichoderma viride.*

As used herein, the term "pectinase" refers broadly to any enzyme that helps break down pectin molecules, including a mixture of such enzymes, or any combination thereof. A pectinase may also be referred to as a pectic enzyme. Examples of different pectinases include, but are not limited to, pectolyase (or pectin lyase, EC 4.2.2.10) and polygalacturonase (or pectin depolymerase, PG, pectolase, pectin hydrolase, EC 3.2.1.15). Commercially available pectinases include, for example, those from fungi like *Rhizopus* sp., *Aspergillus niger* and *Aspergillus aculeatus.*

As used herein, the term "cutinase" refers broadly to any enzyme that helps break down cutin molecules, including a mixture of such enzymes, or any combination thereof. A cutinase is a serine esterase. In one aspect, a cutinase catalyzes the hydrolysis of cutin and may also be referred to as cutin hydrolase (EC 3.1.1.74). Commercially available cutinases include, for example, *Fusarium solani pisi.*

As used herein, the term "lipase" refers broadly to any enzyme that helps break down lipid molecules, or a mixture of such enzymes, or any combination thereof. Lipases are a subclass of the esterase. Commercially available lipases include, for example, those from fungi like *Rhizopus oryzae, Aspergillus niger, Mucor javanicus, Penicillium camemberti, Rhizopus niveous, Mucor miehei, Aspergillus aculeatus, Thirchoderma reesei, Rhizomucor miehei, Thermomyces lanuginosus*, yeast like *Candida rugosa* and other *Candida* sp., or bacteria like *Bacillus subtilis*. In some embodiments, Lipases used include commercially available Palatase® (C-PAL), Amano® lipase G (AL-G), *Thermomyces lanuginosus* Phospholipase A1 (TI-PLA1) and the diatomaceous earths immobilized Amano® lipase PS (iAL-PS, from *Burkholderia cepacia*).

Particulate Abrasives Used to Deliver a Nucleic Acid into a Plant

As used herein, the terms "particulate," "abrasive," and "particulate abrasive" can be used interchangeably, and refer to an agent that can physically disrupt at least one barrier of a plant or plant part.

In some embodiments, the instant disclosure provides methods using mechanical disruption of a surface of the plant to assist in delivery of the nucleic acid to the plant, for example by contacting a surface of a plant with an abrasive such as a loose particulate or a particulate supported on a matrix, or by contacting a surface of a plant with a non-particulate microstructure. Generally the abrasion used in the methods superficially disrupts cells in the cuticle or epidermis or both cuticle and epidermis of the plant, but does not damage cells in deeper tissues of the plant.

Particulates useful in the methods disclosed herein include a particulate abrasive selected from the group consisting of a mineral abrasive, a metal abrasive, a synthetic abrasive, and an organic abrasive. Embodiments include particulate abrasives selected from the group consisting of aluminum oxide, silicon carbide ("carborundum", silicon dioxide, soda lime glass, diatomaceous silica ("diatomaceous earth"), flint, quartz, garnet, silicon dioxide, pumice, sand, feldspar, calcite, steel, tungsten, ceramic, boron carbide, tungsten carbide, an organic or biodegradable abrasive, or combinations of these. In embodiments, the particulate is composed of an organic or biodegradable material, such as, but not limited to wood particles, corn cob particles, grain or seed particles, or nut shell particles.

Particulate size is selected according to factors such as compatibility with a given formulation, suitability for use in a given apparatus (such as a spray nozzle), efficiency in delivering the RNA, or for minimizing damage to the treated plants. In embodiments, the particulate is of an average size range from about 2.5 micrometers to about 50 micrometers. In various embodiments, the particulate is of an average size range from 2.5-50, 2.5-40, 2.5-30, 2.5-20, 5-50, 5-40, 5-30, 5-20, 7-50, 7-40, 7-30, 7-20, 8-50, 8-40, 8-30, 8-20, 10-50, 10-40, 10-30, or 10-25 micrometers. The working Examples further illustrate embodiments of useful particulate size ranges.

Also described herein are compositions and apparatuses useful in delivering a nucleic acid into a plant, as well as plants treated by a method or composition as described herein. In embodiments, DNA- or RNA-coated aluminum oxide or silicon carbide particles are delivered into a plant using a pressurized gas. For example, RNA molecules (e. g., synthetic dsRNA, or a dsRNA produced in a bacterial system) or DNA molecules (e. g., a VIGS vector or a plasmid) are coated onto aluminum oxide ($Al_2O_3$) or silicon carbide (SiC, "carborundum") particles and allowed to dry; these nucleic-acid-coated particles are sprayed onto leaves of a plant using pressurized air or other gas and cause silencing of the gene targeted by the nucleic acid. An airbrush (e. g., Master Airbrush Model G78 Single-Action Gravity Feed Air Abrasive Etching Airbrush Gun as used in the experiments described herein) using compressed air is one convenient means of applying the particulates to the plant. Pressurized gas can be provided by any convenient means, such as an air compressor or a compressed gas cylinder; when used with a dry powder composition, preferably a low-humidity pressurized gas is used.

The abrasion used in these methods preferably does minimal damage to the plant. In embodiments, the particulate disrupts cells only in the cuticle, or only in the cuticle and epidermis of the plant. In embodiments, cells deeper than the epidermis are essentially not damaged by the particulate abrasive. In embodiments, the silencing is systemic and the target gene is silenced in at least one location of the plant that is not the location of abrasion.

In contrast to plant transformation techniques using a gene gun, the particulate-assisted delivery methods and compositions described herein use particulates made of materials less expensive than gold or tungsten and of a size range greater than that of the particles used in gene gun transformation, typically use lower pressures, do not require treatment of the plant in a vacuum, and can be carried out in a whole plant or multiple plants. The methods and compositions are scalable so as to be useful in treating multiple plants at one time.

Polynucleotides

As used herein, "polynucleotide" refers to a nucleic acid molecule containing multiple nucleotides and generally refers both to "oligonucleotides" (a polynucleotide molecule of 18-25 nucleotides in length) and polynucleotides of 26 or more nucleotides. Polynucleotides also include molecules containing multiple nucleotides including non-canonical nucleotides or chemically modified nucleotides as commonly practiced in the art; see, e.g., chemical modifications disclosed in the technical manual "RNA Interference (RNAi) and DsiRNAs", 2011 (Integrated DNA Technologies Coralville, Iowa). Generally, polynucleotides as described herein, whether DNA or RNA or both, and whether single- or double-stranded, include at least one segment of 18 or more contiguous nucleotides (or, in the case of double-stranded polynucleotides, at least 18 contiguous base-pairs) that are essentially identical or essentially complementary to a fragment of equivalent size of the DNA of a target gene or the target gene's RNA transcript. Throughout this disclosure, "at least 18 contiguous" means "from 18 to about 10,000, including every whole number point in between". Aspects of this disclosure include compositions including oligonucleotides having a length of 16-25 nucleotides (e.g., 16-mers, 17-mers, 18-mers, 19-mers, 20-mers, 21-mers, 22-mers, 23-mers, 24-mers, or 25-mers), or medium-length polynucleotides having a length of 26 or more nucleotides (e.g., polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length at least about 300 nucleotides (e.g., polynucleotides of from about 300 to about 400 nucleotides, from about 400 to about 500 nucleotides, from about 500 to about 600 nucleotides, from about 600 to about 700 nucleotides, from about 700 to about 800 nucleotides, from about 800 to about 900 nucleotides, from about 900 to about 1000 nucleotides, from about 300 to about 500 nucleotides, from about 300 to about 600 nucleotides, from about 300 to about 700 nucleotides, from about 300 to about 800 nucleotides, from about 300 to about 900 nucleotides, or about 1000 nucleotides in length, or even greater than about 1000 nucleotides in length, for example, up to 2000 nucleotides, 3000 nucleotides, 4000 nucleotides, 5000 nucleotides in length, or up to the entire length of a target gene including coding or non-coding or both coding and non-coding portions of the target gene). Where a polynucleotide is double-stranded, its length can be similarly described in terms of base pairs.

As used herein, the term "non-transcribable polynucleotide" refers to a polynucleotide that does not comprise a complete polymerase II transcription unit. In some embodiments, the polynucleotide in the compositions and methods disclosed herein is a non-transcribable polynucleotide. In other embodiments, the polynucleotide disclosed herein is a transcribable polynucleotide. In some embodiments, the polynucleotide disclosed herein is a plasmid or a viral vector.

As used herein, the term "trigger," "trigger polynucleotide," or "polynucleotide trigger" refers to a bioactive polynucleotide molecule that is substantially homologous or complementary to a polynucleotide sequence of a target gene or an RNA expressed from the target gene or a fragment thereof and functions to suppress the expression of the target gene or produce a knock-down phenotype. Trigger polynucleotides are capable of inhibiting or "silencing" the expression of a target gene. Trigger polynucleotides are generally described in relation to their "target sequence." Trigger polynucleotides may be single-stranded DNA (ssDNA), single-stranded RNA (ssRNA), double-stranded RNA (dsRNA), double-stranded DNA (dsDNA), or double-stranded DNA/RNA hybrids. Trigger polynucleotides may comprise naturally-occurring nucleotides, modified nucleotides, nucleotide analogues or any combination thereof. In some embodiments, a trigger polynucleotide may be incorporated within a larger polynucleotide. In some embodiments, a trigger polynucleotide may be processed into a small interfering RNA (siRNA).

As used herein, the term "target gene" or "target sequence" refers to a nucleotide sequence that occurs in a gene or gene product against which a trigger polynucleotide is directed. In this context, the term "gene" means a locatable region of genomic sequence, corresponding to a unit of inheritance, which includes regulatory regions, such as promoters, enhancers, 5' untranslated regions, intron regions, 3' untranslated regions, transcribed regions, and other functional sequence regions that may exist as native genes or transgenes in a plant genome or the genome of a pathogen. As used herein, the term "pathogen" refers to virus, viroid, bacteria, fungus, oomycetes, protozoa, phytoplasma, and parasitic plants. Depending upon the circumstances, the term target sequence or target gene can refer to the full-length nucleotide sequence of the gene or gene product targeted for suppression or the nucleotide sequence of a portion of the gene or gene product targeted for suppression.

As used herein, a "dsRNA" molecule refers to a molecule comprising two antiparallel ribonucleotide strands bound together by hydrogen bonds, each strand of which comprises ribonucleotides linked by phosphodiester bonds running in the 5'-3' direction in one and in the 3'-5' direction in the other. Two antiparallel strands of a dsRNA can be perfectly complementary to each other or comprise one or more mismatches up to a degree where any one additional mismatch causes the disassociation of the two antiparallel strands. A dsRNA molecule can have perfect complementarity over the entire dsRNA molecule, or comprises only a portion of the entire molecule in a dsRNA configuration. Two antiparallel strands of a dsRNA can also be from a continuous chain of ribonucleotides linked by phosphodiester bonds, e.g., a hairpin-like structure (often also called a stem-loop structure).

As used herein, the terms "homology" and "identity" when used in relation to nucleic acids, describe the degree of similarity between two or more nucleotide sequences. The percentage of "sequence identity" between two sequences is determined by comparing two optimally aligned sequences over a comparison window, such that the portion of the sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. An alignment of two or more sequences may be performed using any suitable computer program. For example, a widely used and accepted computer program for performing sequence alignments is CLUSTALW v1.6 (Thompson, et al. Nucl. Acids Res., 22: 4673-4680, 1994).

As used herein, the term "essentially identical" or "essentially complementary" means that the bioactive polynucleotide trigger (or at least one strand of a double-stranded polynucleotide or portion thereof, or a portion of a single strand polynucleotide) hybridizes under physiological conditions to the target gene, an RNA transcribed there from, or a fragment thereof, to effect regulation or suppression of the target gene. For example, in some embodiments, a bioactive polynucleotide trigger has 100 percent sequence identity or at least about 80, 81, 82, 83, 84, 85, 86, 87, 88, 89, 90, 91, 92, 93, 94, 95, 96, 97, 98, or 99 percent sequence identity when compared to a sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some embodiments, a bioactive polynucleotide trigger has 100 percent sequence complementarity or at least about 80, 81, 82, 83, 84, 85, 86, 87, 88, 89, 90, 91, 92, 93, 94, 95, 96, 97, 98, or 99 percent sequence complementarity when compared to a sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some embodiments, a bioactive polynucleotide trigger has 100 percent sequence identity with or complementarity to one allele or one family member of a given target gene (coding or non-coding sequence of a gene). In some embodiments, a bioactive polynucleotide trigger has at least about 80, 81, 82, 83, 84, 85, 86, 87, 88, 89, 90, 91, 92, 93, 94, 95, 96, 97, 98, or 99 percent sequence identity with or complementarity to multiple alleles or family members of a given target gene. In some embodiments, a bioactive polynucleotide trigger has 100 percent sequence identity with or complementarity to multiple alleles or family members of a given target gene.

The polynucleotides described herein can be single-stranded (ss) or double-stranded (ds). "Double-stranded" refers to the base-pairing that occurs between sufficiently complementary, anti-parallel nucleic acid strands to form a double-stranded nucleic acid structure, generally under physiologically relevant conditions. Embodiments include those wherein the polynucleotide is selected from the group consisting of sense single-stranded DNA (ssDNA), sense single-stranded RNA (ssRNA), double-stranded RNA (dsRNA), double-stranded DNA (dsDNA), a double-stranded DNA/RNA hybrid, anti-sense ssDNA, or anti-sense ssRNA; a mixture of polynucleotides of any of these types can be used. In some embodiments, the polynucleotide is a microRNA (miRNA), miRNA decoy (e.g., as disclosed in US Patent Application Publication 2009/0070898 which is incorporated herein by reference), a miRNA precursor, or a transacting RNA (ta-siRNA). In some embodiments, the polynucleotide is double-stranded RNA of a length greater than that which is typical of naturally occurring regulatory small RNAs (such as endogenously produced siRNAs and mature miRNAs). In some embodiments, the polynucleotide is double-stranded RNA of at least about 30 contiguous base-pairs in length. In some embodiments, the polynucleotide is double-stranded RNA with a length of from about 50 to about 500 base-pairs. In some embodiments, the polynucleotide can include components other than standard ribonucleotides, e. g., an embodiment is an RNA that comprises terminal deoxyribonucleotides.

In various embodiments, the polynucleotide described herein comprise naturally occurring nucleotides, such as those which occur in DNA and RNA. In certain embodiments, the polynucleotide is a combination of ribonucleotides and deoxyribonucleotides, for example, synthetic polynucleotides consisting mainly of ribonucleotides but with one or more terminal deoxyribonucleotides or one or more terminal dideoxyribonucleotides or synthetic polynucleotides consisting mainly of deoxyribonucleotides but with one or more terminal dideoxyribonucleotides. In certain embodiments, the polynucleotide comprises non-canonical nucleotides such as inosine, thiouridine, or pseudouridine. In certain embodiments, the polynucleotide comprises chemically modified nucleotides. Examples of chemically modified oligonucleotides or polynucleotides are well known in the art; see, for example, U.S. Patent Publication 2011/0171287, U.S. Patent Publication 2011/0171176, U.S. Patent Publication 2011/0152353, U.S. Patent Publication 2011/0152346, and U.S. Patent Publication 2011/0160082, which are herein incorporated by reference. Illustrative examples include, but are not limited to, the naturally occurring phosphodiester backbone of an oligonucleotide or polynucleotide which can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labeled with a fluorescent moiety (e. g., fluorescein or rhodamine) or other label (e. g., biotin).

Several embodiments relate to a polynucleotide comprising at least one segment of 18 or more contiguous nucleotides with a sequence of about 80%, about 81%, about 82%, about 83%, about 84%, about 85%, about 86%, about 87%, about 88%, about 89%, about 90%, about 91%, about 92%, about 93%, about 94%, or about 95% to about 100% identity with a fragment of equivalent length of a DNA of a target gene. In some embodiments, the contiguous nucleotides number at least 16, e.g., from 16 to 24, or from 16 to 25, or from 16 to 26, or from 16 to 27, or from 16 to 28. In some embodiments, the contiguous nucleotides number at least 18, e.g., from 18 to 24, or from 18 to 28, or from 20 to 30, or from 20 to 50, or from 20 to 100, or from 50 to 100, or from 50 to 500, or from 100 to 250, or from 100 to 500, or from 200 to 1000, or from 500 to 2000, or even greater. In some embodiments, the contiguous nucleotides number more than 16, e.g., 17, 18, 19, 20, 21, 22, 23, 24, 25, 26, 27, 28, 29, 30, or greater than 30, e.g., about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 350, about 400, about 450, about 500, about 600, about 700, about 800, about 900, about 1000, or greater than 1000 contiguous nucleotides. In some embodiments, the polynucleotide comprises at least one segment of at least 21 contiguous nucleotides with a sequence of 100% identity with a fragment of equivalent length of a DNA of a target gene. In some embodiments, the polynucleotide is a double-stranded nucleic acid (e.g., dsRNA) with one strand comprising at least one segment of at least 21 contiguous nucleotides with 100% identity with a fragment of equivalent length of a DNA of a target gene; expressed as base-pairs, such a double-stranded nucleic acid comprises at least one segment of at least 21 contiguous, perfectly matched base-pairs which correspond to a fragment of equivalent length of a DNA of a target gene, or the DNA complement thereof. In some embodiments, each segment contained in the polynucleotide is of a length greater than that which is typical of naturally occurring regulatory small RNAs, for example, each segment is at least about 30 contiguous nucleotides (or base-pairs) in length. In some embodiments, the total length of the polynucleotide is between about 50 to about 5000 nucleotides (for single-stranded polynucleotides) or base-pairs (for double-stranded polynucleotides). In some embodiments, the polynucleotide is a dsRNA of between about 50 to about 5000 base-pairs.

Methods of making polynucleotides are well known in the art. Chemical synthesis, in vivo synthesis and in vitro synthesis methods and compositions are known in the art and include various viral elements, microbial cells, modified polymerases, and modified nucleotides. Commercial preparation of oligonucleotides often provides two deoxyribonucleotides on the 3' end of the sense strand. Long polynucleotide molecules can be synthesized from commercially available kits, for example, kits from Applied Biosystems/Ambion (Austin, Tex.) have DNA ligated on the 5' end in a microbial expression cassette that includes a bacterial T7 polymerase promoter that makes RNA strands that can be assembled into a dsRNA and kits provided by various manufacturers that include T7 RiboMax Express (Promega, Madison, Wis.), AmpliScribe T7-Flash (Epicentre, Madison, Wis.), and TranscriptAid T7 High Yield (Fermentas, Glen Burnie, Md.). Polynucleotides as described herein can be produced from microbial expression cassettes in bacterial cells (Ongvarrasopone et al. ScienceAsia 33:35-39; Yin, Appl. Microbiol. Biotechnol 84:323-333, 2009; Liu et al., BMC Biotechnology 10:85, 2010). In some embodiments, the bacterial cells have regulated or deficient RNase III enzyme activity. In some embodiments, fragments of target genes are inserted into the microbial expression cassettes in a position in which the fragments are express to produce ssRNA or dsRNA useful in the methods described herein to regulate expression of the target gene. Long polynucleotide molecules can also be assembled from multiple RNA or DNA fragments. In some embodiments design parameters such as Reynolds score (Reynolds et al. Nature Biotechnology 22, 326-330 (2004) and Tuschl rules (Pei and Tuschl, Nature Methods 3(9): 670-676, 2006) are known in the art and are used in selecting polynucleotide sequences effective in gene silencing. In some embodiments random design or empirical selection of polynucleotide sequences is used in selecting polynucleotide sequences effective in gene silencing. In some embodiments the sequence of a polynucleotide is screened against the genomic DNA of the intended plant to minimize unintentional silencing of other genes.

Target Genes and Trigger Polynucleotides

The methods and compositions in the present disclosure can be used for any trigger polynucleotides designed to modulate the expression of a target gene. The target gene can be an endogenous gene, a viral gene or a transgene. The target gene can be an endogenous plant gene, a transgene expressed in a plant cell, an endogenous gene of a plant pathogen, or a transgene expressed in a plant pathogen. The term "pathogen" refers to virus, viroid, bacteria, fungus, oomycetes, protozoa, phytoplasma, and parasitic plants. In some embodiments, the target gene is 1) is an essential gene for maintaining the growth and life of the plant; 2) encodes a protein that provides herbicide resistance to the plant; or 3) transcribes to an RNA regulatory agent. In some embodiments, the target gene is exogenous to the plant in which the trigger polynucleotide is to be introduced, but endogenous to a plant pathogen.

The target gene can be translatable (coding) sequence, or can be non-coding sequence (such as non-coding regulatory sequence), or both. Examples of a target gene include non-translatable (non-coding) sequence, such as, but not limited to, 5' untranslated regions, promoters, enhancers, or other non-coding transcriptional regions, 3' untranslated regions, terminators, and introns. Target genes include genes encoding microRNAs, small interfering RNAs, and other small RNAs associated with a silencing complex (RISC) or an Argonaute protein; RNA components of ribosomes or ribozymes; small nucleolar RNAs; and other non-coding RNAs. Target genes can also include genes encoding transcription factors and genes encoding enzymes involved in the biosynthesis or catabolism of molecules of interest (such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin).

The target gene can include a single gene or part of a single gene that is targeted for suppression, or can include, for example, multiple consecutive segments of a target gene, multiple non-consecutive segments of a target gene, multiple alleles of a target gene, or multiple target genes from one or more species.

In some embodiments, the compositions and methods described herein are useful for transiently silencing one or more genes in a growing plant cell or whole plant to effect a desired phenotype in response to culture conditions, environmental or abiotic or biotic stress, or change in market demand during the growing season or in the post-harvest environment. For example, compositions and methods as described herein are useful for transiently suppressing a biosynthetic or catabolic gene in order to produce a plant or plant product with a desired phenotype, such as a desired nutritional composition of a crop plant product, e. g., suppressing a FAD2 gene to effect a desired fatty acid profile in soybean or canola or other oilseed or suppressing a lignin biosynthetic genes such as COMT and CCOMT to provide more easily digestible forage plants.

Target genes can include genes encoding herbicide-tolerance proteins, non-coding sequences including regulatory RNAs, and essential genes, which are genes necessary for sustaining cellular life or to support reproduction of an organism. Embodiments of essential genes include genes involved in DNA or RNA replication, gene transcription, RNA-mediated gene regulation, protein synthesis, energy production, and cell division. One example of a compendium of essential genes is described in Zhang et al. (2004) Nucleic Acids Res., 32:D271-D272, and is available at tubic.tju. edu.cn/deg/; version DEG 5.4 lists 777 essential genes for *Arabidopsis thaliana*. Examples of essential genes include translation initiation factor (TIF) and ribulose-1,5-bisphosphate carboxylase oxygenase (RuBisCO). Target genes can include genes encoding transcription factors and genes encoding enzymes involved in the biosynthesis or catabolism of molecules in plants such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin.

Specific examples of suitable target genes also include genes involved in amino acid or fatty acid synthesis, storage, or catabolism, genes involved in multi-step biosynthesis pathways, where it may be of interest to regulate the level of one or more intermediate; and genes encoding cell-cycle control proteins. Target genes can include genes encoding undesirable proteins (e. g., allergens or toxins) or the enzymes for the biosynthesis of undesirable compounds (e. g., undesirable flavor or odor components).

Target genes also include essential genes of a plant pathogen. Essential genes include genes that, when silenced or suppressed, result in the death of the pathogen or in the pathogen's inability to successfully reproduce. In some embodiments, the target gene is a sequence from a pathogenic virus. Examples of fungal plant pathogens include, e. g., the fungi that cause powdery mildew, rust, leaf spot and blight, damping-off, root rot, crown rot, cotton boll rot, stem canker, twig canker, vascular wilt, smut, or mold, including, but not limited to, *Fusarium* spp., *Phakospora* spp., *Rhizoctonia* spp., *Aspergillus* spp., *Gibberella* spp., *Pyricularia* spp., and *Alternaria* spp., and the numerous fungal species provided in Tables 4 and 5 of U.S. Pat. No. 6,194,636, which is specifically incorporated in its entirety by reference herein. Examples of plant pathogens include pathogens previously classified as fungi but more recently classified as oomycetes. Specific examples of oomycete plant pathogens of particular interest include members of the genus *Pythium* (e. g., *Pythium aphanidermatum*) and *Phytophthora* (e. g., *Phytophthora infestans, Phytophthora sojae*,) and organisms that cause downy mildew (e. g., *Peronospora farinosa*).

In some embodiments, the compositions and methods described herein are useful for silencing one or more essential Tospovirus genes thereby treating or preventing Tospoviral infection. Several embodiments relate to improving the resistance of a treated plant to Tospovirus infection. Several embodiments relate to methods of improving resistance to Tospovirus infection in a plant comprising: topically applying to said plant a composition as described herein comprising a double-stranded RNA polynucleotide comprising a sequence that is complementary to all or a portion of an essential Tospovirus gene. In some embodiments, the compositions and methods described herein are useful for silencing one or more essential genes of a Tospovirus selected from the group consisting of bean necrotic mosaic virus, *Capsicum* chlorosis virus, groundnut bud necrosis virus, groundnut ringspot virus, groundnut yellow spot virus, *impatiens* necrotic spot virus, iris yellow spot virus, melon yellow spot virus, peanut bud necrosis virus, peanut yellow spot virus, soybean vein necrosis-associated virus, tomato chlorotic spot virus, tomato necrotic ringspot virus, tomato spotted wilt virus, tomato zonate spot virus, watermelon bud necrosis virus, watermelon silver mottle virus, and zucchini lethal chlorosis virus. In some embodiments, polynucleotide triggers provided herein target one or more essential Tospovirus genes selected from the group consisting of: nucleocapsid gene (N), coat protein gene (CP), virulence factors NSm and NSs, and RNA-dependent RNA polymerase L segment (RdRp/L segment).

In some embodiments, the compositions and methods described herein are useful for silencing one or more essential Geminivirus genes thereby treating or preventing Geminivirus infection. Several embodiments relate to improving the resistance of a treated plant to Geminivirus infection. Several embodiments relate to methods of improving resistance to Geminivirus infection in a plant comprising: topically applying to said plant a composition as described herein comprising a double-stranded RNA polynucleotide comprising a sequence that is complementary to all or a portion of an essential Geminivirus gene. In some embodiments, the compositions and methods described herein are useful for silencing one or more essential genes of a Geminivirus selected from the group consisting of Barley yellow dwarf virus, Cucumber mosaic virus, Pepino mosaic virus, Cotton curl leaf virus, Tomato yellow leaf curl virus, Tomato golden mosaic virus, Potato yellow mosaic virus, Pepper leaf curl virus, Bean golden mosaic virus, Bean golden mosaic virus, Tomato mottle virus. In some embodiments, polynucleotide triggers provided herein target one or more essential Geminivirus genes selected from the group consisting of: nucleocapsid gene (N), a coat protein gene (CP), virulence factors NSm and NSs, and RNA-dependent RNA polymerase L segment (RdRp/L segment), a silencing suppressor gene, movement protein (MP), Nia, CP-N, a triple gene block, CP-P3, MP-P4, C2, and AC2.

In some embodiments, the trigger polynucleotide is a DNA, an RNA, or a DNA/RNA hybrid. In some embodiments, the trigger polynucleotide is single-stranded or double-stranded. In some embodiments, the trigger polynucleotide is from 10 to about 5000 nucleotides (nt) in length. In some embodiments, the trigger polynucleotide is from 15 to about 5000 nucleotides (nt) in length. In some embodiments, the trigger polynucleotide is from 10 to about 1500 nucleotides (nt) in length. In some embodiments, the trigger polynucleotide is from 15 to 1500 nucleotides (nt) in length. In some embodiments, the trigger polynucleotide is from about 20 to about 100, about 75 to about 150, about 100 to about 200, about 150 to about 300, about 200 to about 400, about 300 to about 500, about 400 to about 600, about 500 to about 700, about 600 to about 800, about 700 to 1000, about 900 to about 1200, about 1000 to about 1500, about 1200 to about 2000, about 1500 to about 2500, about 2000 to about 3000, about 2500 to about 3500, about 3000 to about 4000, about 3500 to about 4500, or about 4000 to about 5000 nt in length. In some embodiments, the trigger polynucleotide is about 20, about 30, about 40, about 50, about 60, about 80, about 100, about 120, about 140, about 150, about 160, about 180, about 200, about 220, about 224, about 260, about 280, about 300, about 320, about 340, about 360, about 380, about 400, about 420, about 440, about 460, about 480, about 500, about 550, about 600, about 650, about 700, about 750, about 800, about 850, about 900, about 950, about 1000, about 1100, about 1200, about 1300, about 1400, about 1500, about 2000, about 2500, about 3000, about 3500, about 4000, about 4500, or about 5000 nt in length.

In one aspect, the trigger polynucleotide comprises at least one segment of 18 or more contiguous nucleotides with a sequence of about 80%, about 81%, about 82%, about 83%, about 84%, about 85%, about 86%, about 87%, about 88%, about 89%, about 90%, about 91%, about 92%, about 93%, about 94%, or about 95% to about 100% identity with a fragment of equivalent length of a DNA of a target gene. In some embodiments, the contiguous nucleotides number at least 16, e.g., from 16 to 24, or from 16 to 25, or from 16 to 26, or from 16 to 27, or from 16 to 28. In some embodiments, the contiguous nucleotides number at least 18, e.g., from 18 to 24, or from 18 to 28, or from 20 to 30, or from 20 to 50, or from 20 to 100, or from 50 to 100, or from 50 to 500, or from 100 to 250, or from 100 to 500, or from 200 to 1000, or from 500 to 2000, or even greater. In some embodiments, the contiguous nucleotides number more than 16, e.g., 17, 18, 19, 20, 21, 22, 23, 24, 25, 26, 27, 28, 29, 30, or greater than 30, e.g., about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 350, about 400, about 450, about 500, about 600, about 700, about 800, about 900, about 1000, or greater than 1000 contiguous nucleotides. In some embodiments, the trigger polynucleotide comprises at least one segment of at least 21 contiguous nucleotides with a sequence of 100% identity with a fragment of equivalent length of a DNA of a target gene. In some embodiments, the trigger polynucleotide is a double-stranded nucleic acid (e.g., dsRNA) with one strand comprising at least one segment of at least 21 contiguous nucleotides with 100% identity with a fragment of equivalent length of a DNA of a target gene; expressed as base-pairs, such a double-stranded nucleic acid comprises at least one segment of at least 21 contiguous, perfectly matched base-pairs which correspond to a fragment of equivalent length of a DNA of a target gene, or the DNA complement thereof. In some embodiments, each segment contained in the trigger polynucleotide is of a length greater than that which is typical of naturally occurring regulatory small RNAs, for example, each segment is at least about 30 contiguous nucleotides (or base-pairs) in length. In some embodiments, the total length of the trigger polynucleotide is between about 50 to about 5000 nucleotides (for single-stranded polynucleotides) or base-pairs (for double-stranded polynucleotides). In some embodiments, the trigger polynucleotide is a dsRNA of between about 50 to about 5000 base-pairs. In some embodiments, the polynucleotide is topically provided to the surface of a plant.

Effective trigger polynucleotides of any size can be used, alone or in combination, in the various methods and compositions described herein. In some embodiments, a single polynucleotide trigger is used to make a composition (e.g., a composition for topical application, or a recombinant DNA construct useful for making a transgenic plant). In other embodiments, a mixture or pool of different polynucleotide triggers is used; in such cases the polynucleotide triggers can be for a single target gene or for multiple target genes.

It will be appreciated that a trigger polynucleotide, for example dsRNA, of the present disclosure need not be limited to those molecules containing only natural nucleotides, but further encompasses chemically-modified nucleotides and non-nucleotides. Trigger polynucleotide agents of the present disclosure may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia of Polymer Science And Engineering, pages 858-859, Kroschwitz, J. I., ed. John Wiley & Sons, 1990, those disclosed by Englisch et al., Angewandte Chemie, International Edition, 1991, 613, and those disclosed by Sanghvi, Y. S., Chapter 15, Antisense Research and Applications, pages 289-2, Crooke, S. T. and Lebleu, B., ed., CRC Press, 1993. Such bases are particularly useful for increasing the binding affinity of the oligomeric compounds of the disclosure. These include 5-substituted pyrimidines, 6-azapyrimidines and N-2, N-6 and 0-6 substituted purines, including 2-ami nopropyladenine, 5-propynyluracil and 5-propynylcytosine. 5-methylcytosine substitutions have been shown to increase nucleic acid duplex stability by 0.6-1.2° C. (Sanghvi Y S et al. (1993) Antisense Research and Applications, CRC Press, Boca Raton 276-278) and are presently preferred base substitutions, even more particularly when combined with 2'-O-methoxyethyl sugar modifications.

Methods for in vitro and in vivo expression of RNA for large scale production are known in the art. For example, methods for improved production of dsRNA are disclosed in WO 2014/151581.

Following synthesis or production, the trigger polynucleotides may optionally be purified. For example, polynucleotides can be purified from a mixture by extraction with a solvent or resin, precipitation, electrophoresis, chromatography, or a combination thereof. Alternatively, trigger polynucleotides may be used with no, or a minimum of, purification to avoid losses due to sample processing. The trigger polynucleotides may be dried for storage or dissolved in an aqueous solution. The solution may contain buffers or salts to promote annealing, and/or stabilization of the duplex strands.

Delivery of Site-Specific Enzymes

The methods and compositions in the present disclosure can be used to deliver a polynucleotide encoding a site-specific enzyme from the exterior surface of a plant or plant part into the interior of a plant cell. As used herein, the term "site-specific enzyme" refers to any enzyme that can cleave a nucleotide sequence in a site-specific manner. In an aspect, a site-specific enzyme provided herein is selected from the group consisting of an endonuclease (without being limiting, for example, a meganuclease, a zinc-finger nuclease (ZFN), a transcription activator-like effector nucleases (TALEN), an RNA-guided nuclease (without being limiting, for example, a clustered regularly interspaced short palindromic repeats (CRISPR) Cas9 nuclease, or a Cpf1 nuclease), and a DNA-guided nuclease (without being limiting, for example, the *Natronobacterium gregoryi* Argonaute (NgAgo), a prokaryotic Argonaute that binds to single-stranded guide DNA to create site-specific DNA double-strand breaks); a recombinase (without being limiting, for example, a serine recombinase attached to a DNA recognition motif, a tyrosine recombinase attached to a DNA recognition motif); a transposase (without being limiting, for example, a DNA transposase attached to a DNA binding domain); or any combination thereof. In some embodiments, the polynucleotide encoding a site-specific enzyme comprises a comprise a complete polymerase II transcription unit and is transcribable. In some embodiments, the polynucleotide encoding a site-specific enzyme is mRNA. In an aspect, a polynucleotide provided herein can comprise a nucleic acid sequence encoding a zinc finger nuclease. In an aspect, a polynucleotide provided herein can comprise a nucleic acid sequence encoding a transcription activator-like effector nuclease (TALEN). In an aspect, a polynucleotide provided herein can comprise a nucleic acid sequence encoding a meganuclease. In an aspect, a polynucleotide provided herein can comprise a nucleic acid sequence encoding one or more elements of a CRISPR system. In some embodiments, the CRISPR system is a Type 1 CRISPR system. In some embodiments, the CRISPR system is a Type 2 CRISPR system. In an aspect, a polynucleotide provided herein can comprise a nucleic acid sequence encoding a RNA-guided Cas9 nuclease, an RNA-guided Cpf1 nuclease, an RNA-guided Csc1 nuclease, or an RNA-guided Csc2 nuclease. and the guide RNA necessary for targeting the respective nucleases. In an aspect, a polynucleotide provided herein can comprise a nucleic acid sequence encoding one or more elements of a Cascade a RNA-guided nuclease. In some embodiments, the polynucleotide encodes one or more of RNA components of a RNA-guided nuclease. In some embodiments, the polynucleotide encodes one or more of a guide sequence, a tracr-mate sequence, and a tracr sequence. In some embodiments, the polynucleotide encodes a guide sequence linked to a tracr-mate sequence. In one aspect, a polynucleotide provided herein comprises a nucleic acid sequence encoding one or more elements of a NgAgo-gDNA system. In some embodiments, the polynucleotide encodes a prokaryotic Argonaute. In some embodiments, the prokaryotic Argonaute is from *Natronobacterium gregoryi* (NgAgo), *Thermus thermophiles* (TtAgo), or *Pyrococcus furiosus* (PfAgo). See, e.g., Gao et al., *Nat. Biotechnol.*, May 2, 2016, published online; Swarts et al., *Nature*, 2014, 507(7491):258-61; and Swarts et al., *Nucleic Acid Res.*, 2015, 43(10):5120-5129. In some embodiments, the prokaryotic Argonaute target sequences using 5'-phosphorylated guide DNAs, e.g., the NgAgo, the TtAgo, and the PfAgo known in the art. In some embodiments, the prokaryotic Argonaute targets sequences using 5'-hydroxylated guide RNAs, e.g., the *Marinitoga piezophila* Argonaute (MpAgo) known in the art. E.g., Kaya et al., *Proc. Natl. Acad. Sci.*, Mar. 30, 2016, published online. In some embodiments, the polynucleotide encodes a guide sequence used by a prokaryotic Argonaute.

In general, the term "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. Examples of CRISPR systems and their uses are described in WO 2014/093622 (PCT/US2013/074667), WO 2013/141680, WO 2013/142578, WO 2013/098244 and WO 2013/176772.

Similar to Cas9, endonucleases from the Argonaute protein family also use oligonucleotides as guides to degrade invasive genomes. For example, the *Natronobacterium gregoryi* Argonaute (NgAgo) was found to be a DNA-guided endonuclease suitable for genome editing. NgAgo binds 5' phosphorylated single-stranded guide DNA (gDNA) of ~24 nucleotides, efficiently creates site-specific DNA double-strand breaks when loaded with the gDNA. The NgAgo-gDNA system does not require a protospacer-adjacent motif (PAM), as does Cas9, and it has been suggested that it has a low tolerance to guide-target mismatches and high efficiency in editing (G+C)-rich genomic targets. Gao et al., *Nat. Biotechnol.*, May 2, 2016.

In some embodiments, a CRISPR associated nuclease (e.g., Cas9, Cpf1, Csc1, Csc2, Cascade) can be constitutively present in a plant part and the compositions and methods described herein may be used to deliver one or more RNA components of a CRISPR system from the exterior surface of the plant or plant part into the interior of a plant cell. In some embodiments, a CRISPR enzyme mRNA can be delivered prior to one or more of a guide RNA, a tracr-mate RNA, a tracr RNA, and a guide RNA linked to a tracr-mate RNA to give time for CRISPR enzyme to be expressed. In some embodiments, a CRISPR enzyme mRNA might be administered 1-12 hours (preferably around 2-6 hours) prior to the administration of one or more of a guide RNA, a tracr-mate RNA, a tracr RNA, and a guide RNA linked to a tracr-mate RNA. Alternatively, a CRISPR enzyme mRNA and one or more of a guide RNA, a tracr-mate RNA, a tracr RNA, and a guide RNA linked to a tracr-mate RNA can be administered together. In some embodiments, a second booster dose of one or more of a guide RNA, a tracr-mate RNA, a tracr RNA, and a guide RNA linked to a tracr-mate RNA can be administered 1-12 hours (preferably around 2-6 hours) after the initial administration of CRISPR enzyme mRNA+one or more of a guide RNA, a tracr-mate RNA, a tracr RNA, and a guide RNA linked to a tracr-mate RNA. Additional administrations of CRISPR enzyme mRNA and/or one or more of a guide RNA, a tracr-mate RNA, a tracr RNA, and a guide RNA linked to a tracr-mate RNA according to the compositions and methods described herein might be useful to achieve the most efficient levels of genome modification.

In some embodiments, the methods and compositions in the present disclosure can be used to deliver a site-specific enzyme from the exterior surface of a plant or plant part into the interior of a plant cell. In some embodiments, the methods and compositions in the present disclosure can be used to deliver a CRISPR enzyme from the exterior surface of a plant or plant part into the interior of a plant cell. In some embodiments, the CRISPR enzyme is complexed with one or more RNA components of the CRISPR system. In some embodiments, the CRISPR enzyme is complexed with one or more of a guide RNA, a tracr-mate RNA, a tracr RNA, and a guide RNA linked to a tracr-mate RNA. In some embodiments, the CRISPR enzyme is selected from the group consisting of Cas9, Cpf1, Csc1, Csc2, and Cascade. In some embodiments, the methods and compositions in the present disclosure can be used to deliver a prokaryotic Argonaute from the exterior surface of a plant or plant part into the interior of a plant cell. In some embodiments, the prokaryotic Argonaute is complexed with a guide DNA or a guide RNA. In some embodiments, the prokaryotic Argonaute is *Natronobacterium gregoryi* Argonaute (NgAgo).

Compositions and Methods for Delivery of Polynucleotides

The present disclosure provides a composition for delivering a polynucleotide from the exterior surface of a plant or plant part into the interior of a plant cell, comprising at least one polynucleotide and at least one agent that is able to disrupt at least one barrier of said plant or plant part.

The present disclosure also provides a method for delivering a polynucleotide from the exterior surface of a plant or plant part into the interior of a plant cell, comprising applying to the exterior surface of said plant at least one polynucleotide and at least one agent that is able to disrupt at least one barrier of said plant or plant part.

In some embodiments, the agent is selected from one or more enzymes, one or more abrasives, and any combination thereof. In one embodiment, the agent comprises at least one enzyme. In another embodiment, the agent comprises at least one abrasive. In yet another embodiment, the agent comprises at least one enzyme and at least one abrasive. In some embodiments, the composition further comprises one or more osmolytes, one or more surfactants, or any combination thereof. In some embodiments, the method further comprises applying one or more osmolytes, one or more surfactants, or any combination thereof.

The present disclosure also provides a composition for delivering a polynucleotide from the exterior surface of a plant or plant part into the interior of a plant cell, comprising at least one polynucleotide, one or more osmolytes, and one or more surfactants. In some embodiments, the composition further comprises at least one agent that is able to disrupt at least one barrier of the plant or plant part. In some embodiments, the at least one agent is selected from one or more enzymes, one or more abrasives, and any combination thereof.

The present disclosure also provides a method for delivering a polynucleotide from the exterior surface of a plant or plant part into the interior of a plant cell, comprising a) applying onto the surface of the plant or plant part at least one agent that is able to disrupt at least one barrier of the plant or plant part, and b) applying onto the surface of the plant or plant part one or more polynucleotides, wherein steps a) and b) are carried out concurrently or sequentially in any order. In some embodiments, the at least one agent is selected from one or more enzymes, one or more abrasives, and any combination thereof. In some embodiments, the method further comprises applying onto the surface of the plant or plant part one or more osmolytes, one or more surfactants, or both, where the polynucleotides, the abrasives, the enzymes, the osmolytes, and the surfactants are applied concurrently, or sequentially in any order and grouped in any combination thereof.

The present disclosure also provides a method for delivering a polynucleotide from the exterior surface of a plant or plant part into the interior of a plant cell, comprising applying onto the surface of the plant or plant part one or more polynucleotides, one or more osmolytes, and one or more surfactants, where the polynucleotides, the osmolytes, and the surfactants are applied concurrently, or sequentially in any order and grouped in any combination thereof.

The present disclosure further provides an herbicidal composition adapted for topical application onto an exterior surface of a weed or a volunteer plant, the composition comprising: at least one non-transcribable polynucleotide and at least one agent that is able to disrupt at least one barrier of said weed or volunteer plant, wherein said at least one non-transcribable polynucleotide comprises a sequence essentially identical or essentially complementary to a coding or non-coding sequence of an endogenous gene of said weed or volunteer plant or a messenger RNA that is transcribed from an endogenous gene of said weed or volunteer plant; and wherein said endogenous gene: (i) is an essential gene for maintaining the growth or life of said weed or volunteer plant, (ii) encodes a protein that provides herbicide resistance to said weed or volunteer plant, or (iii) transcribes to an RNA regulatory agent. In some embodiments, the agent is selected from at least one enzyme, at least one abrasive, and any combination thereof. In some embodiments, the composition further comprises at least one osmolyte, at least one surfactant, or any combination thereof.

The present disclosure further provides a method for selectively controlling a targeted herbicide-resistant weed or volunteer plant comprising topically applying onto a surface of said weed or volunteer plant at least one non-transcribable polynucleotide and at least one agent that is able to disrupt at least one barrier of said weed or volunteer plant; wherein said at least one non-transcribable polynucleotide comprises a sequence essentially identical or essentially complementary to a coding or non-coding sequence of an endogenous gene of said weed or volunteer plant or a messenger RNA that is transcribed from an endogenous gene of said weed or volunteer plant; and wherein said endogenous gene: (i) is an essential gene for maintaining the growth or life of said weed or volunteer plant, (ii) encodes a protein that provides herbicide resistance to said weed or volunteer plant, or (iii) transcribes to an RNA regulatory agent. In some embodiments, the agent is selected from at least one enzyme, at least one abrasive, and any combination thereof. In some embodiments, the method further comprises applying at least one osmolyte, at least one surfactant, or any combination thereof.

In one aspect, the present disclosure also provides a composition for delivering a polynucleotide from the exterior surface of a plant or plant part into the interior of a plant cell, comprising at least one non-transcribable polynucleotide and at least one osmolyte or at least one surfactant. In some embodiments, the composition further comprises at least one agent that is able to disrupt at least one barrier of a plant or plant part. In other embodiments, the composition does not comprise an agent that is able to disrupt at least one barrier of a plant or plant part. In some embodiments, the composition comprises both at least one osmolyte and at least one surfactant, with or without at least one agent that is able to disrupt at least one barrier or a plant or plant part. In some embodiments, the agent is selected from at least one enzyme, at least one abrasive, and any combination thereof.

In another aspect, the present disclosure also provides a method for delivering a polynucleotide from the exterior surface of a plant or plant part into the interior of a plant cell, comprising applying to the exterior surface of said plant at least one polynucleotide and at least one osmolyte or at least one surfactant. In some embodiments, the at least one osmolyte or at least one surfactant is applied in the same composition as the at least one polynucleotide. In other embodiments, the at least one osmolyte or at least one surfactant is applied in a different composition from the at least one polynucleotide. In some embodiments, the at least one osmolyte and at least one surfactant are applied in the same composition. In other embodiments, the at least one osmolyte are at least one surfactant are applied in different compositions. In some embodiments, the compositions also comprise at least one agent that is able to disrupt at least one barrier or a plant or plant part. In other embodiments, the compositions do not comprise an agent that is able to disrupt at least one barrier or a plant or plant part. In some embodiments, the agent is selected from at least one enzyme, at least one abrasive, and any combination thereof.

In some embodiments, the polynucleotide is a double-stranded RNA, a single-stranded RNA, a double-stranded DNA, a single-stranded DNA, or a double-stranded DNA/RNA hybrid. In some embodiments, the polynucleotide is a non-transcribable polynucleotide. In some embodiments, the non-transcribable polynucleotide is dsRNA. In some embodiments, the non-transcribable polynucleotide comprises a sequence that is essentially identical or essentially complementary to at least 18 contiguous nucleotides of a target gene or the mRNA transcribed thereof. In some embodiments, the non-transcribable polynucleotide suppresses the expression of the target gene. In some embodiments, the non-transcribable polynucleotide is a microRNA (miRNA), miRNA decoy, a miRNA precursor, or a trans-acting RNA (ta-siRNA).

A target gene can be a coding sequence, a non-coding sequence, or both. In some embodiments, the target gene is selected from (a) an endogenous plant gene, (b) a transgene of a transgenic plant, and (c) an endogenous gene of a plant pathogen. In some embodiments, the target gene a) is an essential gene for maintaining the growth and life of the plant; b) encodes a protein that provides herbicide resistance to the plant; or c) transcribes to an RNA regulatory agent. In some embodiments, the target gene is exogenous to the plant in which the trigger polynucleotide is to be introduced, but endogenous to a plant pathogen. In some embodiments, the target gene is an essential gene of the plant pathogen. In some embodiments, the target gene is a viral gene.

In certain embodiments, the plant is selected from: alfalfa, aneth, apple, apricot, artichoke, arugula, asparagus, avocado, banana, barley, beans, beet, blackberry, blueberry, broccoli, brussel sprouts, cabbage, canola, cantaloupe, carrot, cassava, cauliflower, celery, cherry, cilantro, citrus, clementine, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, Loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini plants.

In certain embodiments, the plant is a weedy plant. Weedy plants are plants that compete with cultivated plants, those of particular importance include, but are not limited to important invasive and noxious weeds and herbicide resistant biotypes in crop production, such as, *Amaranthus* species—*A. albus, A. blitoides, A. hybridus, A. palmeri, A. powellii, A. retroflexus, A. spinosus, A. tuberculatus,* and *A. viridis; Ambrosia* species—*A. trifida, A. artemisifolia; Lolium* species—*L. multiflorum, L. rigidium, L perenne; Digitaria* species—*D. insularis; Euphorbia* species—*E. heterophylla; Kochia* species—*K. scoparia*; Sorghum species—*S. halepense; Conyza* species—*C. bonariensis, C. canadensis, C. sumatrensis; Chloris* species—*C. truncate; Echinochola* species—*E. colona, E. crus-galli; Eleusine* species–*E. indica; Poa* species—*P. annua; Plantago* species—*P. lanceolata; Avena* species—*A. fatua; Chenopodium* species—*C. album; Setaria* species—*S. viridis, Abutilon theophrasti, Ipomoea* species, *Sesbania,* species, *Cassia* species, *Sida* species, *Brachiaria,* species and *Solanum* species.

Additional weedy plant species found in cultivated areas include *Alopecurus myosuroides, Avena sterilis, Avena sterilis ludoviciana, Brachiaria plantaginea, Bromus diandrus, Bromus rigidus, Cynosurus echinatus, Digitaria ciliaris, Digitaria ischaemum, Digitaria sanguinalis, Echinochloa oryzicola, Echinochloa phyllopogon, Eriochloa punctata, Hordeum glaucum, Hordeum leporinum, Ischaemum rugosum, Leptochloa chinensis, Lolium persicum, Phalaris minor, Phalaris paradoxa, Rottboellia exalta, Setaria faberi, Setaria viridis var, robusta-alba schreiber, Setaria viridis var, robusta-purpurea, Snowdenia polystachea, Sorghum sudanese, Alisma plantago-aquatica, Amaranthus lividus, Amaranthus quitensis, Ammania auriculata, Ammania coccinea, Anthemis cotula, Apera spica-venti, Bacopa rotundifolia, Bidens pilosa, Bidens subalternans, Brassica tournefortii, Bromus tectorum, Camelina microcarpa, Chrysanthemum coronarium, Cuscuta campestris, Cyperus difformis, Damasonium minus, Descurainia sophia, Diplotaxis tenuifolia, Echium plantagineum, Elatine triandra var, pedicellata, Euphorbia heterophylla, Fallopia convolvulus, Fimbristylis miliacea, Galeopsis tetrahit, Galium spurium, Helianthus annuus, Iva xanthifolia, Ixophorus unisetus, Ipomoea indica, Ipomoea purpurea, Ipomoea sepiaria, Ipomoea aquatic, Ipomoea triloba, Lactuca serriola, Limnocharis flava, Limnophila erecta, Limnophila sessiliflora, Lindernia dubia, Lindernia dubia var, major, Lindernia micrantha, Lindernia procumbens, Mesembryanthemum crystallinum, Monochoria korsakowii, Monochoria vaginalis, Neslia paniculata, Papaver rhoeas, Parthenium hysterophorus, Pentzia suffruticosa, Phalaris minor, Raphanus raphanistrum, Raphanus sativus, Rapistrum rugosum, Rotala indica var, uliginosa, Sagittaria guyanensis, Sagittaria montevidensis, Sagittaria pygmaea, Salsola iberica, Scirpus juncoides var, ohwianus, Scirpus mucronatus, Setaria lutescens, Sida spinosa, Sinapis arvensis, Sisymbrium orientale, Sisymbrium thellungii, Solanum ptycanthum, Sonchus asper, Sonchus oleraceus, Sorghum bicolor, Stellaria media, Thlaspi arvense, Xanthium strumarium, Arctotheca calendula, Conyza sumatrensis, Crassocephalum crepidiodes, Cuphea carthagenenis, Epilobium adenocaulon, Erigeron philadelphicus, Landoltia punctata, Lepidium virginicum, Monochoria korsakowii, Solanum americanum, Solanum nigrum, Vulpia bromoides, Youngia japonica, Hydrilla verticillata, Carduus nutans, Carduus pycnocephalus, Centaurea solstitialis, Cirsium arvense, Commelina diffusa, Convolvulus arvensis, Daucus carota, Digitaria ischaemum, Echinochloa crus-pavonis, Fimbristy-*

*lis miliacea, Galeopsis tetrahit, Galium spurium, Limnophila erecta, Matricaria perforate, Papaver rhoeas, Ranunculus acris, Soliva sessilis, Sphenoclea zeylanica, Stellaria media, Nassella trichotoma, Stipa neesiana, Agrostis stolonifera, Polygonum aviculare, Alopecurus japonicus, Beckmannia syzigachne, Bromus tectorum, Chloris inflate, Echinochloa erecta, Portulaca oleracea*, and *Senecio vulgaris*.

In certain embodiments, the plant pathogen is virus, viroid, bacteria, fungus, oomycetes, protozoa, phytoplasma, or a parasitic plant.

In certain embodiments, the plant part is a leaf, a stem, a flower, a root, or a fruit. In certain embodiments, the plant cell is an epidermal cell. In other embodiments, the plant cell is not an epidermal cell. In some embodiments, the plant cell is a mesophylle cell, a palisade cell, a parenchyma cell, a collenchyma cell, a sclerenchyma cell, a meristematic cell, a cell in the vascular tissue, a cell in the ground tissue, a cell in the woody tissue, or a cell in the storage organs.

In some embodiments, the barrier of a plant cell is the cuticle of the plant or plant part. In some embodiments, the barrier of a plant cell is the epicuticular wax layer of the plant or plant part. In some embodiments, the barrier of a plant cell is the cell wall of the plant cell. In some embodiments, the barrier of a plant cell is the plasma membrane of the plant cell.

In some embodiments, the enzyme is a cuticle- or wax-hydrolyzing enzyme. In some embodiments, the enzyme breaks down at least one component molecule of a plant cell wall. In some embodiments, the enzyme breaks down at least one component molecule of a plant plasma membrane. In some embodiments, the component molecule of plant cell wall or plant plasma membrane is a carbohydrate, a lipid, a protein, or any combination thereof. In some embodiments, the component molecule of plant cell wall is selected from cellulose, hemicellulose, pectin, or any combination thereof. In some embodiments, the component molecule of plant plasma membrane is a phospholipid.

In some embodiments, the enzyme is a hydrolase. In some embodiments, the enzyme is an esterase. In some embodiments, the enzyme is a lipase, a cutinase, or any combination thereof. In some embodiments, the lipase is selected from the group consisting of Lipolase®, Palatase®, Novocor®, a lipase from *Rhizopus oryzae*, Amano Lipase A from *Aspergillus niger*, Amano Lipase M from *Mucor javanicus*, Amano Lipase G from *Penicillium camemberti*, a lipase from *Candida rugosa*, a lipase from *Rhizopus niveus*, a lipase from *Mucor miehei*, and any combination thereof. In some embodiments, the enzyme is a cellulose, a hemicellulose, a pectinase, or any combination thereof. In some embodiments, the enzyme is a cellulose, a hemicellulose, a pectinase, a cutinase, a lipase, or any combination thereof. In one embodiment, the enzyme is a lipase in a composition further comprising another enzyme selected from a cellulase, a hemicellulase, a pectinase, or any combination thereof. In another embodiment, the enzyme is a lipase in a composition further comprising a surfactant. In some embodiments, the surfactant is a bio-surfactant.

In some embodiments, the abrasive is a mineral abrasive, a metal abrasive, a synthetic abrasive, and an organic abrasive. In some embodiments, the abrasive is selected from the group consisting of aluminum oxide, silicon carbide, silicon dioxide, soda lime glass, diatomaceous silica (diatomaceous earth), flint, quartz, garnet, silicon dioxide, pumice, sand, feldspar, calcite, steel, tungsten, ceramic, boron carbide, and tungsten carbide.

In some embodiments, the particulate disclosed herein is of an average size range from about 2.5 micrometers to about 50 micrometers. In some embodiments, the particulate disclosed herein is of an average size range from about 2.5 to about 10, from about 2.5 to about 20, from about 2.5 to about 30, from about 2.5 to about 40, from about 5 to about 10, from about 5 to about 20, from about 5 to about 30, from about 5 to about 40, from about 5 to about 50, from about 10 to about 20, from about 10 to about 30, from about 10 to about 40, from about 10 to about 50, from about 20 to about 30, from about 20 to about 40, from about 20 to about 50, from about 30 to about 40, from about 30 to about 50, or from about 40 to about 50 micrometers. In some embodiments, the particulate disclosed herein is of an average size of about 2.5, about 3, about 4, about 5, about 6, about 7, about 8, about 9, about 10, about 11, about 12, about 15, about 20, about 25, about 30, about 35, about 40, about 45, or about 50 micrometers.

In some embodiments, the abrasive disclosed herein comprises discrete particles. In other embodiments, the abrasive is supported by, attached to, or embedded in a matrix. In some embodiments, the matrix comprises a fibrous, porous, non-porous, or adhesive support. In some embodiments, the abrasive and the matrix are bonded together. In other embodiments, the abrasive and the matrix are not bounded. In some embodiments, the matrix supporting an abrasive is sandpaper.

In some embodiments, the composition disclosed herein is a liquid, a solid, a powder, a solution, an emulsion, or a suspension. In some embodiments, the composition is applied in a spray. In some embodiments, the spray is applied by an airbrush. In some embodiments, the spray is applied by a compressed-gas sprayer. In other embodiments, the spray is applied by a canister sprayer, a track sprayer, or a boom sprayer.

In some embodiments, the polynucleotide is provided as part of a cell lysate. In some embodiments, the cell lysate is a bacterial lysate.

In some embodiments, the enzyme is provided as part of a cell lysate or cell culture broth. In some embodiments, the cell lysate is bacterial lysate or fungal lysate.

In some embodiments, the enzyme is dialyzed before being provided in a composition.

In some embodiments, the polynucleotide is in a liquid composition. In other embodiments, the polynucleotide is in a powder composition. In some embodiments, the enzyme is in a liquid composition. In other embodiments, the enzyme is in a powder composition. In some embodiments, the abrasive is provided in a liquid composition. In other embodiments, the abrasive is provided in a powder composition. In other embodiments, the abrasive provided to the plant or plant part is on a fixed substrate. In some embodiments, at least one polynucleotide and at least one enzyme are applied to the exterior surface of a plant or plant part in the same composition. In other embodiments, at least one polynucleotide and at least one enzyme are applied to the exterior surface of a plant or plant part in different compositions. In some embodiments, at least one polynucleotide and at least one enzyme are applied to the exterior surface of a plant or plant part concurrently. In other embodiments, at least one polynucleotide and at least one enzyme are applied to the exterior surface of a plant or plant part separately.

In some embodiments, the concentration of the polynucleotide in the composition is from about 0.005 μg/μl to about 10 μg/μl. In some embodiments, the concentration of the polynucleotide in the composition is from about 0.01 to about 10 µg,/µl, from about 0.05 to about 10 µg/µl, from about 0.1 to about 10 µg/µl, from about 0.5 to about 10 µg/µl, from about 1 to about 10 µg/µl, from about 2 to about 10 µg/µl, from about 3 to about 10 µg/µl, from about 4 to about 10 µg/µl, from 5 to about 10 µg/µl, from about 0.1 to about 5 pg/µl, from about 0.5 to about 5 µg/µl, from about 1 to about 5 µg/µl, or from about 2 to about 5 µg/µl. In some embodiments, the concentration of the at least one polynucleotide in the composition is about 0.005 µg/µl, about 0.01 µg/µl, about 0.02 µg/µl, about 0.03 µg/µl, about 0.04 µg/µl, about 0.05 µg/µl, about 0.1 µg/µl, about 0.2 µg/µl, about 0.3 µg/µl, about 0.4 µg/µl, about 0.5 µg/µl, about 1 µg/µl, about 2 µg/µl, about 3 µg/µl, about 4 µg/µl, about 5 µg/µl, about 6 pg/µl, about 7 µg/µl, about 8 µg/µl, about 9 µg/µl, or about 10 pg/µl.

In some embodiments, the concentration of the enzyme in the composition is from about 10 U/ml to about 10,000 U/ml. In some embodiments, the concentration of the enzyme in the composition is from about 3,000 U/ml to about 5,000 U/ml. In some embodiments, the concentration of the enzyme in the composition is from about 1,000 U/ml to about 6,000 U/ml. In some embodiments, the concentration is about 10 U/ml, about 20 U/ml, about 30 U/ml, about 40 U/ml, about 50 U/ml, about 100 U/ml, about 200 U/ml, about 300 U/ml, about 400 U/ml, about 500 U/ml, about 600 U/ml, about 700 U/ml, about 800 U/ml, about 900 U/ml, about 1,000 U/ml, about 1,500 U/ml, about 2,000 U/ml, about 2,500 U/ml, about 3,000 U/ml, about 3,500 U/ml, about 4,000 U/ml, about 4,500 U/ml, about 5,000 U/ml, about 5,500 U/ml, about 6,000 U/ml, about 6,500 U/ml, about 7,000 U/ml, about 7,500 U/ml, about 8,000 U/ml, about 8,500 U/ml, about 9,000 U/ml, about 9,500 U/ml, or about 10,000 U/ml.

In some embodiments, the compositions of the present disclosure further comprise an osmolyte. In some embodiments, the osmolyte is a naturally occurring organic compound. In some embodiments, the osmolyte is an amino acid, a methylamine, or a polyol. Osmolytes used include but are not limited to sugar alcohols such as sorbitol, mannitol, xylitol, erythrol; glycerol; monosaccharides such as glucose or disaccharides such as sucrose; amino acids such as proline, valine, isoleucine, ectoine, or aspartic acid; trehalose, glycine betaine (betaine), carnitine, taurine, sarcosine, myo-inositol (inositol). In certain embodiments, the osmolyte is selected from the group consisting of sucrose, sorbitol, mannitol, glycerol, polyethylene glycol (PEG), D-proline, L-proline, betaine, and any combination thereof. In some embodiments, the PEG has a molecular weight no more than 5,000 g/mol. In some embodiments, the osmolyte is PEG 300 or PEG 400. In some embodiments, the osmolyte is at a concentration from about 1 mM to about 500 mM. In other embodiments, the osmolyte is at a concentration of from about 10 mM to about 500 mM. In some embodiments, the osmolyte is at a concentration of from about 100 mM to about 500 mM. In some embodiments, the osmolyte is at a concentration of at least 500 mM. In some embodiments, the osmolyte is at a concentration from about 5 mM to about 500 mM, from about 10 mM to about 500 mM, from about 20 mM to about 500 mM, from about 25 mM to about 500 mM, from about 50 mM to about 500 mM, from about 75 mM to about 500 mM, from about 100 mM to about 500 mM, from about 125 mM to about 500 mM, from about 150 mM to about 500 mM, from about 175 mM to about 500 mM, from about 200 mM to about 500 mM, from about 250 mM to about 500 mM, from about 5 mM to about 250 mM, from about 10 mM to about 250 mM, from about 20 mM to about 250 mM, from about 25 mM to about 250 mM, from about 50 mM to about 250 mM, from about 100 mM to about 250 mM, from about 5 mM to about 150 mM, from about 10 mM to about 150 mM, from about 20 mM to about 150 mM, from about 25 mM to about 150 mM, from about 50 mM to about 150 mM from about 5 mM to about 100 mM, from about 10 mM to about 100 mM, from about 20 mM to about 100 mM, from about 25 mM to about 100 mM, and from about 50 mM to about 100 mM. In some embodiments, the osmolyte is at a concentration of about 1 mM, about 2 mM, about 3 mM, about 4 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 110 mM, about 120 mM, about 125 mM, about 150 mM, about 175 mM, about 200 mM, about 250 mM, about 300 mM, about 400 mM, about 500 mM, about 600 mM, about 700 mM, about 800 mM, about 900 mM, or about 1000 mM. In some embodiments, the compositions of the present disclosure comprise at least one polynucleotide and at least one osmolyte, with or without an enzyme or a surfactant. In some embodiments, the compositions of the present disclosure comprise at least two, at least three, or at least four different osmolytes. In some embodiments, the composition further comprises at least one surfactant, or a blend of at least two, at least three, or at least four different surfactants. In some embodiments, the composition further comprises at least one enzyme that is able to disrupt at least one barrier of a plant or plant part. In some embodiments, the composition comprises a mixture of at least two, at least three, or at least four different enzymes.

In some embodiments, the compositions of the present disclosure further comprise a buffering agent. Examples of common buffering agents include, but are not limited to, acetate, MES, citrate, BIS-TRIS, MOPS, phosphate, carbonate, HEPES, tricine, Tris, Bicine, TAPS, taurine, borate, and CAPS.

In some embodiments, the compositions of the present disclosure do not comprise any buffering agent. In one embodiment, at least one non-transcribable polynucleotide and/or at least one enzyme are in a water base formulation.

In some embodiments, the compositions of the present disclosure further comprise pesticide. The pesticide may be, for example, an insecticide, a fungicide, an herbicide, or an nematicide.

Non-limiting examples of insecticides and nematicides include carbamates, diamides, macrocyclic lactones, neonicotinoids, organophosphates, phenylpyrazoles, pyrethrins, spinosyns, synthetic pyrethroids, tetronic and tetramic acids. In particular embodiments insecticides and nematicides include abamectin, aldicarb, aldoxycarb, bifenthrin, carbofuran, chlorantraniliporle, chlothianidin, cyfluthrin, cyhalothrin, cypermethrin, deltamethrin, dinotefuran, emamectin, ethiprole, fenamiphos, fipronil, flubendiamide, fosthiazate, imidacloprid, ivermectin, lambda-cyhalothrin, milbemectin, nitenpyram, oxamyl, permethrin, spinetoram, spinosad, spirodichlofen, spirotetramat, tefluthrin, thiacloprid, thiamethoxam, and thiodicarb.

Non-limiting examples of useful fungicides include aromatic hydrocarbons, benzimidazoles, benzthiadiazole, carboxamides, carboxylic acid amides, morpholines, phenylamides, phosphonates, quinone outside inhibitors (e.g. strobilurins), thiazolidines, thiophanates, thiophene carboxamides, and triazoles. Particular examples of fungicides include acibenzolar-S-methyl, azoxystrobin, benalaxyl, bixafen, boscalid, carbendazim, cyproconazole, dimethomorph, epoxiconazole, fludioxonil, fluopyram, fluoxastrobin, flutianil, flutolanil, fluxapyroxad, fosetyl-Al, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thiabendazole, thifluzamide, thiophanate, tolclofos-methyl, trifloxystrobin, and triticonazole.

In some embodiments, the compositions of the present disclosure further comprise one or more herbicides that can be added to the composition of the present disclosure that provide multi-species weed control or alternative modes of action for difficult to control weed species, for example, members of the herbicide families that include but are not limited to amide herbicides, aromatic acid herbicides, arsenical herbicides, benzothiazole herbicides, benzoylcyclohexanedione herbicides, benzofuranyl alkylsulfonate herbicides, carbamate herbicides, cyclohexene oxime herbicides, cyclopropylisoxazole herbicides, dicarboximide herbicides, dinitroaniline herbicides, dinitrophenol herbicides, diphenyl ether herbicides, dithiocarbamate herbicides, halogenated aliphatic herbicides, imidazolinone herbicides, inorganic herbicides, nitrile herbicides, organophosphorus herbicides, oxadiazolone herbicides, oxazole herbicides, phenoxy herbicides, phenylenediamine herbicides, pyrazole herbicides, pyridazine herbicides, pyridazinone herbicides, pyridine herbicides, pyrimidinediamine herbicides, pyrimidinyloxybenzylamine herbicides, quaternary ammonium herbicides, thiocarbamate herbicides, thiocarbonate herbicides, thiourea herbicides, triazine herbicides, triazinone herbicides, triazole herbicides, triazolone herbicides, triazolopyrimidine herbicides, uracil herbicides, and urea herbicides. In particular, the rates of use of the added herbicides can be reduced in compositions comprising the polynucleotides of the present disclosure. Use rate reductions of the additional added herbicides can be 10-25 percent, 26-50 percent, 51-75 percent or more can be achieved that enhance the activity of the polynucleotides and herbicide composition and is contemplated as an aspect of the present disclosure.

Auxin-like herbicides include benzoic acid herbicide, phenoxy carboxylic acid herbicide, pyridine carboxylic acid herbicide, quinoline carboxylic acid herbicide, pyrimidine carboxylic acid herbicide, and benazolin-ethyl herbicide.

The benzoic acid herbicide group (dicamba (3,6-dichloro-o-anisic acid), chloramben (3-amino-2,5-dichlorobenzoic acid), and TBA (2,3,6-trichlorobenzoic acid)) are effective herbicides for both pre-emergence and post-emergence weed management. Dicamba is one of the many auxin-like herbicides that is a low-cost, environmentally friendly herbicide that has been used as a pre-emergence and post-emergence herbicide to effectively control annual and perennial broadleaf weeds and several grassy weeds in corn, sorghum, small grains, pasture, hay, rangeland, sugarcane, asparagus, turf, and grass seed crops (Crop Protection Chemicals Reference, pp. 1803-1821, Chemical & Pharmaceutical Press, Inc., New York, N.Y., 11th ed., 1995). Dicamba refers to 3,6-dichloro-o-anisic acid or 3,6-dichloro-2-methoxy benzoic acid and its acids and salts. Its salts include isopropylamine, diglycoamine, dimethylamine, potassium and sodium. Dicamba includes for example, commercial formulations without limitation, Banvel™ (as DMA salt, BASF, Research Triangle Park, N.C.), Clarity® (DGA salt, BASF), VEL-58-CS-11™ (BASF) and Vanquish™ (DGA salt, BASF). Dicamba is a useful herbicide as a tank mix, concomitantly, or pre or post treatment with the compositions of the present disclosure.

An auxin-like herbicide also includes a phenoxy carboxylic acid compound, a pyridine carboxylic acid compound, a quinoline carboxylic acid compound, and a benazolin-ethyl compound. Examples of a phenoxy carboxylic acid compound include, but are not limited to 2,4-dichlorophenoxyacetic acid, (4-chloro-2-methylphenoxy) acetic acid, diclorprop (2,4-DP), mecoprop (MCPP), and clomeprop. Examples of pyridine herbicides include, but are not limited to clopryalid, picloram, fluroxypyr, aminocyclopyrachlor and triclopyr. These auxin-like herbicides are useful in a tank mix, concomitantly, or pre or post treatment with the compositions of the present disclosure. Auxin-like herbicides include commercially available formulations, for example, including but not limited to 2,4-D, 2,4-DB (Butyracil) 200, Bakker), MCPA (Rhonox®, Rhomene), mecoprop, dichlorprop, 2,4,5-T, triclopyr (Garton®, Dow AgroSciences, Indianapolis, Ind.), chloramben, dicamba (Banvel®, Clarity®, Oracle®, Sterling®), 2,3,6-TBA, tricamba, clopyralid (Stinger®, Dow Agro Sciences), picloram (Tordon®, Dow Agro Sciences), quinmerac, quinclorac, benazolin, fenac, IAA, NAA, orthonil and fluroxypyr (Vista®, Starane®, Dow AgroSciences), aminopyralid (Milestone®, Dow AgroSciences) and aminocyclopyrachlor (Dupont, Wilmington, Del.).

In some embodiments, the herbicide is glyphosate. "Glyphosate" (N-phosphonomethylglycine) herbicide inhibits the shikimic acid pathway which leads to the biosynthesis of aromatic compounds including amino acids, plant hormones and vitamins. Specifically, glyphosate curbs the conversion of phosphoenolpyruvic acid (PEP) and 3-phosphoshikimic acid to 5-enolpyruvyl-3-phosphoshikimic acid by inhibiting the enzyme 5-enolpyruvylshikimate-3-phosphate synthase (hereinafter referred to as EPSP synthase or EPSPS). For purposes of the present disclosure, the term "glyphosate" should be considered to include any herbicidally effective form of N-phosphonomethylglycine (including any salt thereof) and other forms which result in the production of the glyphosate anion in planta. Glyphosate is an example of an EPSPS inhibitor herbicide. Herbicides are molecules that affect plant growth or development or reproductive ability.

Glyphosate is commercially available in numerous formulations. Examples of these formulations of glyphosate include, without limitation, those sold by Monsanto Company (St Louis, Mo.) as ROUNDUP®, ROUNDUP® ULTRA, ROUNDUP® ULTRAMAX, ROUNDUP® CT, ROUNDUP® EXTRA, ROUNDUP® BIACTIVE, ROUNDUP® BIOFORCE, RODEO®, POLARIS®, SPARK® and ACCORD® herbicides, all of which contain glyphosate as its isopropylammonium salt, ROUNDUP® WEATHERMAX containing glyphosate as its potassium salt; ROUNDUP® DRY and RIVAL® herbicides, which contain glyphosate as its ammonium salt; ROUNDUP® GEOFORCE, which contains glyphosate as its sodium salt; and TOUCHDOWN® herbicide (Syngenta, Greensboro, N.C.), which contains glyphosate as its trimethylsulfonium salt. Various other salts of glyphosate are available for example, dimethylamine salt, isopropylamine salt, trimesium salt, potassium salt, monoammonium salt, and diammonium salt.

In one aspect of the present disclosure, the polynucleotide suppresses the expression of a target gene. In certain embodiments, the polynucleotide suppresses the expression of a target gene in an epidermal cell. In some embodiments, the polynucleotide suppresses the expression of a target gene in a mesophylle cell.

In certain embodiments, the compositions disclosed herein areapplied onto the surface of a leaf. In some embodiments, a liquid composition is applied onto the surface of a leaf at about 1 to about 20 µL formulation per square centimeter (sq-cm) of the leaf area.

In some embodiments, the polynucleotide is applied onto the surface of a plant or plant part at a final concentration from about 0.005 µg/µl to about 10 µg/µl. In some embodiments, the concentration of the polynucleotide in the composition is from about 0.01 to about 10 µg/µl, from 0.05 to about 10 µg/µl, from about 0.1 to about 10 µg/µl, from about 0.5 to about 10 pg/µl, from about 1 to about 10 µg/µl, from about 2 to about 10 pg/µl, from about 3 to about 10 µg/µl, from about 4 to about 10 pg/µl, from 5 to about 10 pg/µl, from about 0.1 to about 5 µg/µl, from about 0.5 to about 5 pg/µl, from about 1 to about 5 µg/µl, or from about 2 to about 5 µg/µl. In some embodiments, the concentration of the polynucleotide in the composition is about 0.005 pg/µl, about 0.01 µg/µl, about 0.02 µg/µl, about 0.03 µg/µl, about 0.04 µg/µl, about 0.05 µg/µl, about 0.1 µg/µl, about 0.2 µg/µl, about 0.3 µg/µl, about 0.4 µg/µl, about 0.5 µg/µl, about 1 pg/µl, about 2 µg/µl, about 3 pg/µl, about 4 pg/µl, about 5 µg/µl, about 6 µg/µl, about 7 µg/µl, about 8 µg/µl, about 9 µg/µl, or about 10 pg/µl.

In some embodiments, the enzyme is applied onto the surface of a plant or plant part at a final concentration of from about 10 U/ml to about 10,000 U/ml. In some embodiments, the final concentration of the enzyme for application is from about 3,000 U/ml to about 5,000 U/ml. In some embodiments, the final concentration of the enzyme for application is from about 1,000 U/ml to about 6,000 U/ml. In some embodiments, the concentration is about 10 U/ml, about 20 U/ml, about 30 U/ml, about 40 U/ml, about 50 U/ml, about 100 U/ml, about 200 U/ml, about 300 U/ml, about 400 U/ml, about 500 U/ml, about 600 U/ml, about 700 U/ml, about 800 U/ml, about 900 U/ml, about 1,000 U/ml, about 1,500 U/ml, about 2,000 U/ml, about 2,500 U/ml, about 3,000 U/ml, about 3,500 U/ml, about 4,000 U/ml, about 4,500 U/ml, about 5,000 U/ml, about 5,500 U/ml, about 6,000 U/ml, about 6,500 U/ml, about 7,000 U/ml, about 7,500 U/ml, about 8,000 U/ml, about 8,500 U/ml, about 9,000 U/ml, about 9,500 U/ml, or about 10,000 U/ml.

In some embodiments, at least one polynucleotide and at least one agent that is able to disrupt at least one of the plant barriers are applied onto the surface of a plant or plant part in the same composition. In other embodiments, at least one polynucleotide and at least one agent that is able to disrupt at least one of the plant barriers are applied onto the surface of a plant or plant part in different compositions. In some embodiments, the different compositions are applied to the plant or plant part concurrently. In other embodiments, the different compositions are applied to the plant or plant part separately.

In some embodiments, at least one polynucleotide and at least one agent that is able to disrupt at least one of the plant barriers are applied onto the surface of a plant or plant part separately. In some embodiments, one is applied immediately after another. In some embodiments, at least one polynucleotide and at least one agent that is able to disrupt at least one of the plant barriers, e.g., at least one enzyme, are applied onto the surface of a plant or plant part at least 10 min, at least 20 min, at least 30 min, at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 15 hours, at least 20 hours, at least 24 hours, at least 36 hours, or at least 48 hours apart.

In some embodiments, at least one polynucleotide is applied onto the surface of the plant or plant part before at least one agent that is able to disrupt at least one of the plant barriers is applied. In some embodiments, the polynucleotide is applied immediately before the enzyme is applied. In some embodiments, the polynucleotide is applied at least 10 min, at least 20 min, at least 30 min, at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 15 hours, at least 18 hours, at least 20 hours, at least 24 hours, at least 30 hours, or at least 36 hours before the enzyme is applied.

In some embodiments, the composition comprising at least one polynucleotide and/or at least one agent that is able to disrupt at least one of the plant barriers is re-applied at least once, at least twice, or at least three times onto the surface of the plant or plant part at an interval of at least 24 hours after the initial application. In some embodiments, the interval of the reapplied mixture is from about 24 hours to about 14 days. In some embodiments, the interval of the reapplied mixture is about 24 hours, about 36 hours, about 48 hours, or about 72 hours. In other embodiments, the interval of the reapplied mixture is from about 1 day to about 14 days, from about 2 days to about 10 days, or from about 2 days to about 5 days. In yet other embodiments, the interval of the reapplied mixture is about 3 days, about 4 days, about 5 days, about 6 days, about 7 days, about 8 days, about 9 days, about 10 days, about 11 days, about 12 days, about 13 days, or about 14 days.

In some embodiments, at least 1%, at least 2%, at least 3%, at least 4%, at least 5%, at least 6%, at least 7%, at least 8%, at least 9%, at least 10%, at least 15%, at least 20%, at least 30%, at least 40%, at least 50%, at least 60%, at least 70%, at least 80%, or at least 90% of the total area on the surface of the plant or plant art is in contact with the composition comprising the polynucleotide.

In some embodiments, suppression of target gene expression by a trigger polynucleotide as provided herein is observed at least one day, at least two days, at least three days, at least four days, at least five days, at least six days, at least seven days, at least eight days, at least nine days, at least ten days, at least one week, at least two weeks, or at least three weeks after the application of the composition comprising the trigger polynucleotide.

In some embodiments, the composition comprising at least one polynucleotide and/or at least one agent that is able to disrupt at least one of the plant barriers is dissolved or suspended in an aqueous solution. In other embodiments, the composition is a dry powder. In some embodiments, the composition is applied using an aerosol or nebulizer. In other embodiments, the aqueous solution is applied using a track sprayer. In some embodiments, the aqueous solution is applied using a sprayer at an air pressure from about 10 to about 50 psi, or from about 20 to about 30 psi. In some embodiments, the aqueous solution is applied at a rate from about 5 to about 40 gallons per acre.

In some embodiments, the compositions of the present disclosure further contain solid and liquid carriers and surface-active agents (e.g. wetters, dispersants or emulsifiers alone or in combination). Surface-active agents that may be present in the polynucleotide compositions of the present disclosure may be of the ionic or non-ionic types, for example sulphoricinoleates, quaternary ammonium derivatives, products based on condensates of ethylene oxide with nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphono-succinates and alkali and alkaline earth metal salts of high molecular weight sulphonic acid derivatives such as sodium and calcium lignosulphonates. Examples of solid diluents or carriers include, but are not limited to, aluminum silicate, talc, calcined magnesia, kieselguhr, tricalcium phosphate, powdered cork, absorbent carbon black and clays such as kaolin and bentonite. Examples of liquid diluents include, but are not limited to, water, acetophenone, cyclohexanone, isophorone, toluene, xylene, and mineral, animal, and vegetable oils. These diluents may be used alone or in any combination thereof. In some embodiments, the polynucleotide compositions or mixture of the present application may also contain conventional adjuvants such as adhesives, protective colloids, thickeners, penetrating agents, stabilisers, sequestering agents, anti-caking agents, coloring agents, and corrosion inhibitors. These adjuvants may also serve as carriers or diluents.

In some embodiments, the compositions of the present disclosure are wettable powders or water dispersible granules. In some embodiments, the polynucleotide compositions or mixture are aqueous suspension concentrates. In some embodiments, the wettable powders (or powder for spraying) may contain from 0% to about 5% of a wetting agent, from about 3% to about 10% of a dispersant agent and/or other additives such as penetrating agents, adhesives, or anti-caking agents and colorings. In some embodiments, the aqueous suspension concentrates, which are applicable by spraying, are prepared in such a way as to obtain a stable fluid product (e.g., by fine grinding) which does not settle out. In some embodiments, the aqueous suspension concentrates contain from 0% to about 10% of suitable additives such as antifoams, corrosion inhibitors, and stabilisers.

The polynucleotide compositions of the present disclosure optionally may further comprise conventional additives such as surfactants, drift reduction agents, softeners, solubility enhancing agents, thickening agents, flow enhancers, foam-moderating agents, freeze protectants, UV protectants, preservatives, antimicrobials, and/or other additives that are necessary or desirable to improve the performance, crop safety, or handling of the composition.

In some embodiments, the polynucleotide composition further comprises a surfactant. In some embodiments, the surfactant is a nonionic surfactant selected from: organosilicone surfactants, polysorbate, cetostearyl alcohol, cetyl alcohol, oleyl alcohol, stearyl alcohol, cocamide DEA, cocamide MEA, polyalkylglucoside, decyl glucoside, lauryl glucoside, octyl glucoside, monolaurin, poloxamer, sorbitan monostearate, sorbitan tristearate, or any combination thereof. Examples of commercially available nonionic surfactants include, but are not limited to, silicones such as Silwet® L-77 from Momentive, alkyl polyglucosides, available under the Agnique PG brand from BASF (formerly Cognis), ethoxylated fatty acids and alcohols, available from Lamberti, BASF, Croda, Akzo Nobel, Stepan, and many other manufacturers, and ethoxylated sorbitan esters available under the Tween® tradename from Croda and as Alkest® TW from Oxiteno.

In some embodiments, the surfactant is selected from Silwet® L-77, Hexaethylene glycol monododecyl ether (HGME), Tween®-20, Tween®-80, Nonanoic acid, Triton™ X-100, Span®80, BREAK-THRU® SP131, BREAK-THRU® SP133, BREAK-THRU® S210, and any combination thereof. In some embodiments, the surfactant is a sorbitan-fatty acid ester or a non-ionic polysorbate fatty acid ester surfactant. In some embodiments, the surfactant in the composition is at a concentration of about 0.01% to about 10%, about 0.05% to about 10%, about 0.1% to about 10%, about 0.2% to about 10%, about 0.5% to about 10%, about 1% to about 10%, about 0.01% to about 5%, about 0.05% to about 5%, about 0.1% to about 5%, about 0.2% to about 5%, about 0.5% to about 5%, about 1% to about 5%, about 0.05% to about 2%, about 0.1% to about 2%, or about 0.5% to about 2%. In some embodiments, the surfactant is at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 1.2%, about 1.5%, about 2%, about 3%, about 4%, about 5%, about 6%, about 7%, about 8%, about 9%, or about 10%.

In some embodiments, the polynucleotide composition comprises a blend of at least two surfactants, at least three surfactants, or at least four surfactants. In some embodiments, the polynucleotide composition comprises at least two surfactants at a ratio from about 10:1 to about 1:10. In some embodiments, the polynucleotide composition comprises at least two surfactants at a ratio from about 8:1 to about 1:8, from about 5:1 to about 1:5, from about 4:1 to about 1:4, from about 3:1 to about 1:3, from about 2:1 to about 1:2, from about 1.5:1 to about 1:1.5, or at a ratio of about 1:1. In one embodiment, the composition comprises a blend of Tween®80 and Span®80 at a ratio of about 3:1.

In some embodiments, the surfactant is a bio-surfactant. A bio-surfactant is a surface-active substance synthesized by living cells. In some embodiments, the bio-surfactant is produced by a microorganism. In certain embodiments, the bio-surfactant is produced by a bacterium or a fungi. Examples of bio-surfactants include, but are not limited to, Lipopeptides (e.g. *Bacillus subtilis* surfactin), glycolipids (e.g., di- and mono-rhamnolipids from *P. aeruginosa*), 1',4'-Sophorolactone 6',6'-diacetate (e.g., from *Candida* sp.), trehalose lipids (from *Rhodococcus* spp.) and mannosylerythritol lipids (*Candida antartica*). In some embodiments, the bio-surfactant is selected from a lipopeptide, a glycolipid, a trehalose lipid, a mannosylerythritol lipid, 1',4'-Sophorolactone 6',6'-diacetate, and any combination thereof.

In some embodiments, the composition disclosed herein further comprises at least one osmolyte, or a mixture of at least two, at least three, or at four different osmolytes. In some embodiments, the one or more osmolytes are selected from sucrose, mannitol, glycerol, and any combination thereof.

In some embodiments, the polynucleotide mixture or polynucleotide composition further comprises a photoprotectant. In some embodiments, the photoprotectant is an anionic photoprotectant. In some embodiments, the photoprotectant is a water-soluble photoprotectant. Examples of photoprotectants include, but are not limited to: Benzophenone-9 (CAS No. 76656-36-5) available as Maxgard 800 from Lycus Ltd. (El Dorado, Ak.) and as Helisorb-11DS from Norquay Technology (Chester, Pa.). Benzophenone-9 is an aromatic di-sulfonate which absorbs primarily in the ultraviolet. Visible anionic dyes with the "FD&C" designation, indicating approval in food, drug and cosmetics, such as FD&C Blue no. 1 and FD&C Green 3 are also photoprotectants. In one specific embodiment, the photoprotectant is Benzophenone 9. In some embodiments, the photoprotectant is at a concentration from about 0.1% to about 5%, from about 0.2% to about 5%, from about 0.5% to about 5%, from about 0.1% to about 2%, or from about 0.5% to about 1.5%. In some embodiments, the photoprotectant is at a concentration of about 0.1%, about 0.2%, about 0.5%, about 1%, about 1.5%, about 2%, about 2.5%, about 3%, about 3.5%, about 4%, about 4.5%, or about 5%.

In some embodiments, the polynucleotide mixture or polynucleotide composition further comprises a biocide. In some embodiments, the biocide is a pesticide. In some embodiments, the biocide is an herbicide.

In some embodiments, the compositions disclosed herein comprise a pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein.

In certain embodiments, the compositions of the present disclosure further comprises a chelator. Examples include, but are not limited to: citric acid, salts of ethylenediamine tetracetic acid (EDTA), and any combination thereof. In some embodiments, the chelator is at a concentration of about 0.01% to about 5%, about 0.01% to about 1%, about 0.01% to about 0.5%, 0.01% to about 0.25%, about 0.02% to about 1%, about 0.02% to about 0.5%, about 0.05% to about 1%, about 0.05% to about 0.5%, or about 0.1% to about 0.25%. In some embodiments, the chelator is at a concentration of about 0.01%, about 0.02%, about 0.03%, about 0.04%, about 0.05%, about 0.06%, about 0.07%, about 0.08%, about 0.09%, about 0.1%, about 0.125%, about 0.15%, about 0.175%, about 0.2%, about 0.225%, about 0.25%, about 0.3%, about 0.35%, about 0.4%, about 0.45%, about 0.5%, about 0.6%, about 0.7%, about 0.8%, about 0.9%, about 1%, about 1.5%, about 2%, about 2.5%, about 3%, about 3.5%, about 4%, about 4.5%, or about 5%.

The polynucleotide mixture or polynucleotide composition can also further comprise a defoamer, such as silicones. One example is Agnique® DFM 111S from BASF.

In certain embodiments, the compositions of the present disclosure further comprise a ribonuclease inhibitor. Examples include, but are not limited to, zinc sulfate, RNAsin®, and any combination thereof.

In certain embodiments, the compositions of the present disclosure further comprise an inhibitor or elicitor of plant immune response in plants. Examples of inhibitors of plant immune response include, but are not limited to, oxalic acid salts, DPI, 2-deoxy-D-glucose (DDG), and any combination thereof. Examples of elicitors of plant immune response include but not limited to: salicylic acid, microbial derived peptides (e.g., alamethicin), proteins, polysaccharides and lipids, and any combination thereof.

In certain embodiments, the compositions of the present disclosure further comprise a cell transfection agent. Examples include but not limited to: lipid nanoparticles, polymers and cell penetrating peptides and endocytosis effectors.

In embodiments, the methods, compositions, and apparatuses described herein are useful for obtaining a phenotype (e.g., improved yield, improved resistance temperature, water, or nutrient stress, improved resistance to pathogens, improved herbicide susceptibility, improved herbicide resistance, and modified nutrient content or appearance) in a plant directly treated by a method as described herein. In other embodiments, the effect of treatment by a method of this disclosure is passed on to subsequent generations, for example in an epigenetic effect. In many embodiments the DNA or RNA employed in the methods is designed to silence a target gene. In related applications the methods can be used to deliver any nucleic acid of interest, including nucleic acids designed for gene editing, e.g., using a CRISPR or Cas9 system.

The present disclosure also provides a spray apparatus for spraying multiple plants or multiple rows of plants, comprising a propellant source, at least one spray nozzle, and a reservoir containing a composition comprising a polynucleotide and at least one abrasive. It also provides an apparatus for introducing a nucleic acid into a whole plant, comprising a) a matrix supporting an abrasive, and b) a nucleic acid. It further provides a method for introducing a nucleic acid into a whole plant comprising, in any order, the steps of: a) mechanical penetration of a surface of a whole plant with a non-particulate microstructure, and b) contacting the surface of the whole plant with a nucleic acid.

The following Examples are presented for the purposes of illustration and should not be construed as limitations.

EXAMPLES

Example 1: Delivery of dsRNA to *Nicotiana benthamiana* 16C-GFP Plants Using a Liquid Formulation with Lipase Enzymes In this example, young *Nicotiana benthamiana* plants (2-3 week old plants) were treated with a formulation containing dsRNA targeting GFP, either in water only or with a buffer solution consisting of 200 mM glycerol, 4 mM MES. Additional-components were 1% pectinase from a stock containing >3800 U/ml (Sigma P2611) and 2% cellulase from a stock containing >700 U/g (1.1-1.3 g/ml, Sigma C2730), with or without lipases as illustrated in Table 1 below. The lipases used were Palatase® 20,000 U/g (Sigma L4277; from *Rhizomucor miehei*) at 300 U/ml; Lipolase® 100,000 U/g (Sigma L0777; from *Thermomyces lanuginosus*) at 300 U/ml; or NovoCor® AD L 6,000 U/g (L3420; from *Candida* sp.) at 300 U/ml. Lipase enzymes were used either alone or in combination as a 3-enzyme cocktail mixture (each lipase at 150 U/ml in the cocktail formulation).

Formulations were applied to plant leaves using a 1-step method, whereby all components were first mixed together and then gently pipetted onto three leaves. An average of 14-17 pit formulation per square centimeter (sq-cm) of leaf area was applied to each treated leaf. In order to get a measurement of surface area to volume ratio for proper formulation delivery, leaves were excised from *N. benthamiana* plants and imaged using Fiji Image J freeware (fiji.sc/How_to_cite_Fiji %3F). The surface area was averaged across the number of leaves imaged. The youngest application leaf was the apical leaf measuring roughly 2-4 mm in length, these leaves had an average surface area of 0.18 sq-cm/leaf and were typically treated with 2-4 µl, formulation. The second type of leaves were slightly larger in size and termed medium sized leaves, measuring in size approximately 0.51 sq-cm/leaf. These leaves were treated with 5-9 µL formulation. The largest leaves treated averaged approximately 1.85 sq-cm/leaf in surface area and were treated with 20 µl formulation per leaf.

A second delivery method employed a 2-step delivery in which the dsRNA was premixed with either water or buffer first and applied to the three youngest leaves by gentle pipetting, followed, 24 hrs later by application of the lipase enzyme/s in water or buffer. In the 2-step application procedure the lipase enzyme concentration was 100 U/ml (single enzymes) or 50 U/ml each when the three enzymes were used as a mixture. The volume applied to the plant leaves was as described above, ~2-4 µL on apical leaves, ~5-9 µL on medium sized leaves and ~18-20 µl on larger leaves with the goal of keeping a consistent volume to surface area ratio. The formulation was spread gently over the top of the leaf with the side of the pipet tip. The dsRNA used targets the GFP in the transgenic *Nicotiana benthamiana* 16C line and consists of a 124 bp dsRNA polynucleotide. Table 2 illustrates the formulation that was applied to the young treated plants. Each treatment consisted of 3 plants.

TABLE 1

Lipases used in delivery of GFP dsRNA to young *Nicotiana benthamiana* plants.

| Plant # | cell wall enzymes | GFP dsRNA (124 bp) | cuticle enzymes | core formulation | Application method: 2-Step? |
|---|---|---|---|---|---|
| 1a | Pectinase 1% | yes | 3-enzyme cocktail 150-450 U/ml | buffer | yes |
| 1b |  |  |  |  | no |
| 2a | Cellulase 2% |  |  | water | yes |
| 2b |  |  |  |  | no |
| 3a |  |  | Palatase ® ~100-300 U/ml | buffer | yes |
| 3b |  |  |  |  | no |
| 4a |  |  |  | water | yes |
| 4b |  |  |  |  | no |
| 5a |  |  | Lipolase ® ~100-300 U/ml | buffer | yes |
| 5b |  |  |  |  | no |
| 6a |  |  |  | water | yes |
| 6b |  |  |  |  | no |
| 7a |  |  | Novocor ® ~100-300 U/ml | buffer | yes |
| 7b |  |  |  |  | no |
| 8a |  |  |  | water | yes |
| 8b |  |  |  |  | no |

TABLE 2

Compositions of the formulations applied to *Nicotiana benthamiana* 16C-GFP plants

| Plant # | μl glycerol (800 mM stock) | μl MES (200 mM stock) | μl pectinase | μl cellulase | 3-enzyme cocktail | Palatase ® (1/10 dil) | Lipolase ® (1/100 dil) | Novocor ® (1/10 dil) | dsRNA trigger (20 μg/μl stock) | H$_2$O | total |
|---|---|---|---|---|---|---|---|---|---|---|---|
| 1b | 28.75 | 2.3 | 1.15 | 2.3 | 49.70 |  |  |  | 23 | 7.80 | 115 |
| 2b |  |  | 1.15 | 2.3 | 49.70 |  |  |  | 23 | 38.85 | 115 |
| 3b | 28.75 | 2.3 | 1.15 | 2.3 |  | 15.13 |  |  | 23 | 42.37 | 115 |
| 4b |  |  | 1.15 | 2.3 |  | 15.13 |  |  | 23 | 73.42 | 115 |
| 5b | 28.75 | 2.3 | 1.15 | 2.3 |  |  | 33.82 |  | 23 | 23.68 | 115 |
| 6b |  |  | 1.15 | 2.3 |  |  | 33.82 |  | 23 | 54.73 | 115 |
| 7b | 28.75 | 2.3 | 1.15 | 2.3 |  |  |  | 50.44 | 23 | 7.06 | 115 |
| 8b |  |  | 1.15 | 2.3 |  |  |  | 50.44 | 23 | 38.11 | 115 |

Plants were observed for phenotype development at 3, 6, 10 and 19 days after treatment (DAT). Suppression of GFP expression was visible as early as 3DAT as evidenced by red chlorophyll fluorescence under blue light (470 nm excitation). Table 3 summarizes the localized and systemic GFP suppression observed in the treated plants.

TABLE 3

Plant totals with localized or systemic GFP suppression

|  |  | WATER |  | BUFFER |  | TOTALS w/suppression |  |
|---|---|---|---|---|---|---|---|
|  | Treatment | # (of 3) w/visible suppression | # Showing Systemic suppression | # (of 3) w/visible suppression | # Showing Systemic suppression | phenotype observed at 3 DAT | Systemic observed at 19 DAT |
| One-Step Application | 3-enzyme Cocktail (1-step) | — | — | 1 | 1 | 1/6 | 1/6 |
|  | Palatase ® (1-step) | 2 | 1 | 3 | 2 | 5/6 | 3/6 |
|  | Lipolase ® (1-step) | 3 | 3 | 3 | 1 | 6/6 | 4/6 |
|  | Novocor ® (1-step) | 1 | — | — | — | 1/6 | — |
| Two-Step Application | 3-enzyme Cocktail (2-step) | 3 | 2 | 1 | 1 | 4/6 | 3/6 |
|  | Palatase ® (2-step) | 1 | — | — | — | 1/6 | — |

TABLE 3-continued

Plant totals with localized or systemic GFP suppression

| | WATER | | BUFFER | | TOTALS w/suppression | |
|---|---|---|---|---|---|---|
| Treatment | # (of 3) w/visible suppression | # Showing Systemic suppression | # (of 3) w/visible suppression | # Showing Systemic suppression | phenotype observed at 3 DAT | Systemic observed at 19 DAT |
| Lipolase ® (2-step) | 3 | 1 | 2 | — | 5/6 | 1/6 |
| Novocor ® (2-step) | 1 | — | — | — | 1/6 | — |
| TOTALS | 14/24 | 7/24 | 10/24 | 5/24 | | |

Plants treated with either the 1-step or 2-step application method developed localized suppression symptoms that were visible as early as 3DAT. Based on the number of plants that exhibited systemic suppression of GFP it appeared that the 1-step application method was trending more effective in delivering the polynucleotide to the plant cells in order to initiate suppression.

Example 2. Suppression of Gene Expression of an Endogenous Gene by Application of a dsRNA Polynucleotide in a Liquid Formulation with a Lipase Enzyme In this example young *Nicotiana benthamiana* 16C-GFP plants (2-3 weeks of age) were treated with a dsRNA (122 bp in length) targeting the endogenous Magnesium chelatase (MgChl) enzyme in the same base formulation as described in Example 1, with either Palatase® or Lipolase® enzyme. Table 4 summarizes the formulations used in this example.

control formulations which contained either GFP trigger (off-target control) or no trigger.

Example 3. GFP Silencing and MgChl Silencing Phenotypes Co-Localized when Using a Mixture of dsRNA Polynucleotides Delivered in Liquid Formulation with a Lipase Enzyme In this example, *Nicotiana benthamiana* 16C-GFP plants (2-3 weeks of age) were treated with a dsRNA (122 bp in length) targeting the endogenous Magnesium chelatase (MgChl) enzyme and a dsRNA (124 bp in length) targeting the transgenic GFP gene in the same base formulation as described in Example 1, with either Palatase or Lipolase enzyme. Table 5 summarizes the formulation used in this experiment.

TABLE 4

Formulations used for the MgChl experiments.

| Component group | Components | TRT1 | TRT2 | TRT3 | TRT4 | TRT5 | TRT6 |
|---|---|---|---|---|---|---|---|
| Base formulation | Glycerol | 200 mM | 200 mM | 200 mM | 200 mM | 200 mM | 200 mM |
| | MES (pH = 5.7) | 4 mM | 4 mM | 4 mM | 4 mM | 4 mM | 4 mM |
| Hydrolytic enzymes | Cellulase | 2% | 2% | 2% | 2% | 2% | 2% |
| | Pectinase | 1% | 1% | 1% | 1% | 1% | 1% |
| | Palatase ® | | 300 U/ml | | 300 U/ml | | 300 U/ml |
| | Lipolase ® | 300 U/ml | | 300 U/ml | | 300 U/ml | |
| | MgChl (dsRNA) | | | 4 µg/µl | 4 µg/µl | | |
| | GFP (dsRNA) | | | | | 2 µg/µl | 2 µg/µl |
| RESULTS (# plants showing CHL KD phenotype) | | 0/12 | 0/12 | 1/6 | 1/6 | 0/6 | 0/6 |

Three leaves per plant were treated with formulation. Each treatment group consisted of three plants. In this example all applications were delivered using the 1-step methodology. Following treatment a MgChl silencing phenotype as evidenced by chlorotic spots on the leaves visible under ambient light was observed as early as 3DAT in formulations containing the MgChl dsRNA, but not in

TABLE 5

Formulation used for delivering MgChl and GFP polynucleotides to *N. benthamiana* plants

| Component group | Components | TRT |
|---|---|---|
| Base formulation | Glycerol | 100-200 mM |
| | MES (pH = 5.7) | 4 mM |

TABLE 5-continued

Formulation used for delivering MgChl and GFP polynucleotides to *N. benthamiana* plants

| Component group | Components | TRT |
|---|---|---|
| Hydrolytic enzymes | Cellulase | 0-2% |
| | Pectinase | 0-1% |
| | Palatase | 150-300 U/ml |
| | Lipolase | 150-300 U/ml |
| Polynucleotides | MgChl + GFP mixture | 4 µg/µl + 2 µg/µl |
| RESULTS (# plants showing CHL knock-down phenotype) | | 19/24 |
| RESULTS (# plants showing GFP knock-down phenotype) | | 22/24 |

Plants were visualized either under UV or ambient light at different time points after treatment. Suppression of gene expression was observed as early as 5DAT. Dark brown/reddish spots were observed on all leaves on all treated plants (3/3) under UV light indicating that GFP expression had been suppressed, while under ambient light chlorotic spots characteristic of MgChl suppression were visible in the same location as the GFP suppression.

0.25% Pectinase. Palatase® and Lipolase® were used at concentrations as shown in Table 6. Tomato leaves most closely resemble an ellipse, so the surface area of the leaf was measured by first adding the leaf diameter in both directions and then multiplying the resulting value by $\pi$ ($\pi$=3.14). The average application volume for tomato leaves was 27 µL per sq-cm of leaf. The following table summarizes the formulations used.

TABLE 6

Compositions of the formulations used in the tomato liquid enzyme delivery protocol

| Component group | Components | Treatment |
|---|---|---|
| Base formulation | Mannitol | 25 mM |
| | MES (pH = 5.7) | 4 mM |
| Hydrolytic enzymes | Cellulase | 0.5% |
| | Pectinase | 0.25% |
| | Palatase | up to 228 U/ml |
| | Lipolase | up to 510 U/ml |
| Polynucleotides | MgChl + GFP cocktail | 4 µg/µL + 2 µg/µl |

Tomato plants were scored for suppression of Magnesium Chelatase gene expression by looking for chlorotic spots in the young treated leaves under ambient light starting with 4DAT. A summary of the experimental results is presented below in Table 7.

TABLE 7

Plants exhibiting suppression of MgChl at 4 days after treatment with dsRNA in a hydrolytic enzymatic formulation

| Treatment # | Mannitol | MES | % Pectinase | % Cellulase | units/ml Palatase | units/ml Lipolase | µg/µl Mg Che dsRNA | µg/µl GFP dsRNA | # plants with Mg Chel phenotype |
|---|---|---|---|---|---|---|---|---|---|
| 1 | 25 mM | 4 mM | 0.5 | 0.25 | 228 | | 4 | | 1/5 |
| 2 | 25 mM | 4 mM | 0.5 | 0.25 | 114 | | 4 | | 3/5 |
| 3 | 25 mM | 4 mM | 0.5 | 0.25 | 57 | | 4 | | 2/5 |
| 4 | 25 mM | 4 mM | | | 228 | | 4 | | 5/5 |
| 5 | 25 mM | 4 mM | | | 114 | | 4 | | 5/5 |
| 6 | 25 mM | 4 mM | | | 57 | | 4 | | 4/5 |
| 7 | 25 mM | 4 mM | 0.5 | 0.25 | | 510 | 4 | | 5/5 |
| 8 | 25 mM | 4 mM | 0.5 | 0.25 | | 225 | 4 | | 2/5 |
| 9 | 25 mM | 4 mM | 0.5 | 0.25 | | 112.5 | 4 | | 3/5 |
| 10 | 25 mM | 4 mM | | | | 510 | 4 | | 2/5 |
| 11 | 25 mM | 4 mM | | | | 225 | 4 | | 3/5 |
| 12 | 25 mM | 4 mM | | | | 112.5 | 4 | | 2/5 |
| 13 | 25 mM | 4 mM | 0.5 | 0.25 | | | 4 | | 2/5 |
| 14 | 25 mM | 4 mM | 0 | 0 | | | 4 | | 5/5 |
| 15 | 25 mM | 4 mM | 0 | 0 | | | | 4 | 0/5 |
| 16 | 25 mM | 4 mM | 0 | 0 | | | 4 | | 3/5 |
| 17 | untreated | | 0 | 0 | | | 0 | | 0/5 |

Example 4. Suppression of Gene Expression of an Endogenous Gene in Tomato by Application of a dsRNA Polynucleotide in a Liquid Formulation with a Lipase Enzyme In this example young tomato plants (*Solanum lycopersicum* cv. Celebrity, 2-3 week stage) were treated with a dsRNA targeting the endogenous Magnesium chelatase (MgChl; 122 bp dsRNA polynucleotide) enzyme or with a dsRNA targeting GFP (124 bp dsRNA polynucleotide) as an off target control. The base buffer formulation contained 25 mM Mannitol and 4 mM MES as well as 0.5% Cellulase and Tomato plants treated with a base buffer solution, dsRNA targeting MgChl and the hydrolytic enzyme Palatase® had a high number of symptomatic results evidenced by the chlorotic spots on young developing leaves visible under ambient light (treatments #4, 5 and 6). Localized suppression of MgChl was observed in 5/5 plants treated with 228 U/ml Palatase (treatment #4,). Localized suppression of MgChl was also observed with Lipolase® (treatments #10-12). Formulations of cellulase and pectinase (treatment #7, 510 U/ml) showed suppression of MgChl in 5/5 treated plants.

Example 5. A Liquid Formulation Comprising a dsRNA, a Lipase Enzyme and a Surfactant is Sufficient for Delivery and Suppression of Gene Expression in Planta In the example outlined below in Table 8, *Nicotiana benthamiana* 16C seedlings were treated with a formulation containing a lipase enzyme, a surfactant and a dsRNA targeting the transgenic GFP gene. The volume applied is the same as outlined in Example 1 above and the stage of the leaves treated for the application is as in Examples 1 and 4.

TABLE 8

Formulations used and the results observed in *N. benthamiana* 16C seedlings treated with dsRNA targeting GFP, Palatase ® and Silwet L77.

| Treatment | Palatase ® U/ml | Surfactant | dsRNA | Plant species | Observation |
|---|---|---|---|---|---|
| 1 | 2257 | Silwet ® L-77 (0.05%) | GFP (124 bp) 4 µg/µl | *N. benthamiana* 16C | 3/3 plants with GFP silencing phenotype |

Beginning with 3DAT all three treated plants showed a local suppression phenotype as evidenced by red chlorophyll fluorescence under blue light (470 nm excitation) indicating suppression of GFP expression.

Example 6. Application of a Topical Formulation for Gene Suppression Using Spray methodology In this example a topical formulation containing hydrolytic lipase enzymes mixed with dsRNA for gene suppression was delivered using a sprayer onto tobacco *Nicotiana benthamiana* 16C seedlings. *Nicotiana benthamiana* 16C seedlings (2 weeks of age) were treated with formulation containing hydrolytic lipase in buffer solution containing dsRNA either by hand application (control) using a pipette or by spraying. Eight (8) seedlings at the 4 leaf (4 L) and four (4) seedlings at the 2 leaf (2 L) emerged leaves stage were sprayed with formulation using a MiniAir compressor Model TC207 piston type with a Master Airbrush model G233-SET. Air pressure was set at 20-30 psi. Seedlings at the 4 L stage were sprayed across leaf 3, 4 and seedling apex by holding the sprayer about 5 cm away from the seedling. Seedlings at the 2 L stage were sprayed across the whole plant. Composition of formulations applied by hand included 2500 or 5000 U/ml of the lipase Palatase® in a base formulation containing 50 mM glycerol, 4 mM MES (pH 5.7) and dsRNA targeting GFP (124 bp dsRNA polynucleotide) or dsRNA targeting endogenous MgChl (122 bp dsRNA polynucleotide) at 4 mg/ml. The composition of the formulations and the results observed is summarized in Table 9 below.

TABLE 9

Formulations and results for delivery of liquid formulation using spray methodology

| Treatment ID | Application method | Base formulation | Lipase Units/ml | Lipase | dsRNA | Summary # plants with local silencing/# treated plants (2 L) | # plants with local silencing/# treated plants (4 L) |
|---|---|---|---|---|---|---|---|
| 1 | Sprayed | 50 mM Glycerol + 4 mM MES | 2500 | Palatase ® | GFP | 3/4 | 2/8 |
| 2 | Sprayed | 50 mM Glycerol + 4 mM MES | 5000 | Palatase ® | GFP | 3/4 | 4/8 |
| 3 | Sprayed | 50 mM Glycerol + 4 mM MES | 2500 | Palatase ® | MgChl | 0/4 | 3/8 |
| 4 | Sprayed | 50 mM Glycerol + 4 mM MES | 5000 | Palatase ® | MgChl | 2/4 | 2/8 |

GFP silencing spots were observed under UV light as early as 4 days after treatment. Magnesium chelatase chlorotic spots were observed under ambient light. Localized symptom development was observed in all but one treatment (treatment #3), and systemic silencing was observed in one plant for each of treatments 1 and 2. The most plants exhibiting local silencing were observed in treatment #2 consisting of the highest concentration of Palatase (5000 U/ml) tested in combination with dsRNA targeting GFP.

Example 7. A Bacterial Lysate from *E. coli* K12 Engineered to Produce a dsRNA Hairpin Targeting GFP and Spiked with Lipase Enzyme is Sufficient to Suppress Transgene Expression In this example, *E. coli* K12 strain was modified to express a 660 bp dsRNA hairpin targeting GFP. Young *N. benthamiana* 16C plants (2-3 weeks old) that overexpress GFP, were topically treated with the liquid lysate resulting from *E. coli* K12::GFP in the presence or absence of Palatase® enzyme. Table 10 summarizes the composition of the microbial formulations used in this experiment.

TABLE 10

Microbial based formulation composition used in *N. benthamiana* 16C topical applications

| Components | Treatment 1 | Treatment 2 |
|---|---|---|
| *E. coli* lysate::GFP | 118.5 µl | 118.5 µl |
| Palatase ® | 10 µl (1520 U/ml) | 30 µl (4560 U/ml) |
| dH₂O | 21.5 µl | 1.5 µl |

Each treatment consisted of three plants. The formulation was applied to the plants and the plants were monitored daily for suppression of GFP symptom development. As early as 3 days after treatment (3 DAT) localized GFP silencing foci (evidenced by the red chlorophyll fluorescence upon exposure to UV light (470 nm)) were observed in the plants inoculated with treatments #1 and #2 with stronger symptoms being observed for plants treated with the formulation in treatment #2.

Example 8. Enhancement of Suppression of Gene Expression of a Transgene by Application of a dsRNA Polynucleotide in a Liquid Formulation with a Commercially Available Surfactant and a Lipase Enzyme In this example young 2-3 weeks of age and older 3-4 week *Nicotiana benthamiana* 16C-GFP plants were treated with a dsRNA targeting the transgenic GFP transcript (124 bp in length) in a base formulation containing different commercially available surfactants as described in Table 11 below, with either Palatase® or Lipolase® enzyme. Commercially available surfactants used in this example were Silwet® L-77, Hexaethylene glycol monododecyl ether (HGME), Tween®-20, nonanoic acid and Triton™ X-100.

TABLE 11

Formulations used to evaluate GFP silencing efficacy with compositions including commercially available surfactants and lipase enzymes.

| Component group | Components | 1 | 2 | 3 | 4 | 5 | 6 | 7 | 8 | 9 | 10 | 11 | 12 |
|---|---|---|---|---|---|---|---|---|---|---|---|---|---|
| Base formulation | Glycerol (mM) | 50 | 50 | 50 | 50 | 50 | 50 | 50 | 50 | 50 | 50 | 50 | 50 |
| | MES (pH = 5.7) (mM) | 4 | 4 | 4 | 4 | 4 | 4 | 4 | 4 | 4 | 4 | 4 | 4 |
| | Silwet ® L77 (%) | | 0.05 | | | | | | | 0.05 | | | |
| | HGME (%) | | | 0.1 | | | | | | | 0.1 | | |
| | Tween ®-20 (%) | | | | 0.1 | | | | | | | 0.1 | |
| | Nonanoic acid (%) | | | | | 0.1 | | | | | | | 0.1 |
| | Triton ™ X-100 (%) | | | | | | 0.1 | | | | | | 0.1 |
| Hydrolytic enzymes | Lipolase ® (U/ml) | | | | | | | 5134 | 5134 | 5134 | 5134 | 5134 | 5134 |
| | Palatase ® (U/ml) | 2257 | 2257 | 2257 | 2257 | 2257 | 2257 | | | | | | |
| Polynucleotide | GFP (dsRNA) (µg/µl) | 4 | 4 | 4 | 4 | 4 | 4 | 4 | 4 | 4 | 4 | 4 | 4 |

Three leaves and apical meristematic region per plant were treated with formulation. In this example all applications were delivered using the 1-step methodology. Following treatment GFP silencing phenotype was observed as evidenced by dark red spots observed on the leaves under blue light (470 nm) and using a combination of green (Green 11, Tiffen) and yellow (Yellow 12, Tiffen) filters. Images for phenotypic characterization were taken at 14 DAT and the results are summarized in Table 12.

TABLE 12

GFP silencing efficacy results from experiments testing formulations composition including commercially available surfactants and lipase enzymes

| Treatment ID | # Plants with phenotype (n = 3) | | Average number of leaves with phenotype per plant | |
|---|---|---|---|---|
| | 2-3 week old seedling | 3-4 week old seedling | 2-3 week old seedling | 3-4 week old seedling |
| TRT1 | 2 | 3 | 1.5 | 2 |
| TRT2 | 1 | 3 | 1 | 1 |

TABLE 12-continued

GFP silencing efficacy results from experiments testing formulations composition including commercially available surfactants and lipase enzymes

| Treatment ID | # Plants with phenotype (n = 3) | | Average number of leaves with phenotype per plant | |
|---|---|---|---|---|
| | 2-3 week old seedling | 3-4 week old seedling | 2-3 week old seedling | 3-4 week old seedling |
| TRT3 | 1 | 0 | 1 | 0 |
| TRT4 | 1 | 3 | 1 | 2 |
| TRT5 | 2 | 3 | 1.5 | 3 |
| TRT6 | 3 | 3 | 1.3 | 1.3 |
| TRT7 | 2 | 3 | 1.5 | 1.3 |
| TRT8 | 2 | 2 | 1 | 1 |
| TRT9 | 0 | 0 | 0 | 0 |
| TRT10 | 2 | 2 | 2 | 2 |
| TRT11 | 3 | 2 | 1 | 3 |
| TRT12 | 0 | 3 | 0 | 1.7 |

Treatment of plants using nonanoic acid (treatment #5) in combination with Palatase (2257 U/ml) produced silencing in both really young (2-3 week old) and slightly older (3-4 week old) treated seedlings.

Example 9. Liquid Formulations Containing Lipases Isolated from Other Microorganisms can Deliver dsRNA to GFP into N. benthamiana 16C Plants In this example commercially available lipases isolated from a number of microorganisms were tested for their ability to deliver dsRNA in formulation to young N. benthamiana plants (2-3 week old plants). Two experiments were carried out, both utilizing the 1-step delivery method using hand application of the formulation. In both experiments the base formulation contained 4 mM MES, and 4 mg/ml of the dsRNA GFP trigger. The lipases were obtained as powder from Sigma and resuspended in 1×PBS. The final enzyme concentration ranged from approximately 20 U/ml to approximately 2283 U/ml. In this experiment 6 plants were tested per treatment. Table 13 summarizes the concentrations and results obtained from testing.

TABLE 13

Lipases used in formulation studies for delivery of dsRNA to N. benthamiana and observed results

| Enzyme | Parent Species | Concentration (U/ml) | #plants with Phenotype Experiment #1 |
|---|---|---|---|
| Lipase | Rhizopus oryzae (Sigma#62305) | 200 | 4/6 |
| Amano Lipase A | Aspergillus niger (Sigma#534781) | 1000 | 5/6 |
| Amano Lipase M | Mucor javanicus (Sigma#534803) | 200 | 4/6 |
| Amano Lipase G | Penicillium camemberti (Sigma#534838) | 1000 | 3/6 |
| Lipase | Candida rugosa (Sigma#L8525) | 2160 | 3/6 |
| Lipase | Rhizopus niveus (Sigma#62310) | 100 | 0/6 |
| Lipase | Mucor miehei (Sigma#L9031) | 2283 | 2/6 |
| Lipase | Rhizopus oryzae | 20 | 1/6 |
| Amano Lipase A | Aspergillus niger | 100 | 2/6 |
| Amano Lipase M | Mucor javanicus | 20 | 1/6 |
| Amano Lipase G | Penicillium camemberti | 100 | 1/6 |
| Lipase | Candida rugosa | 216 | 1/5 |
| Lipase | Rhizopus niveus | 100 | 0/6 |
| Lipase | Mucor miehei | 228 | 1/6 |

Robust effects were observed in plants treated with lipase formulations from A. niger (5/6 plants with GFP silencing phenotype), R. oryzae and M. javanicus (in both cases 4/6 plants observed with silencing phenotype).

In the second delivery experiment the concentration of lipase in the formulation was doubled (2×/treatment) and a subset of lipases listed in Table 13 were further examined for their delivery ability. In this experiment three plants were tested per treatment. The results of these treatments are summarized in Table 14.

TABLE 14

Results of treatment of N. benthamiana with formulations containing lipases from different microorganisms and dsRNA.

| Enzyme | Parent Species | Concentration (U/ml) | #plants with Phenotype-Experiment #2 |
|---|---|---|---|
| Lipase | Rhizopus oryzae | 400 | 3/3 |
| Amano Lipase M | Mucor javanicus | 400 | 3/3 |
| Amano Lipase G | Penicillium camemberti | 2000 | 2/3 |
| Lipase | Candida rugosa | 4320 | 2/3 |
| Lipase | Mucor miehei | 4565 | 2/3 |

Treatment with lipases from R. oryzae and M javanicus at 400 U/ml showed silencing of GFP expression in 3/3 plants tested.

Example 10. A Liquid Formulation Containing a Lipase and dsRNA Based in Water is Sufficient to Suppress Expression of a Transgene In this example, young N. benthamiana 16C seedling (2-3 week old plants) were topically treated with a formulation containing differing Lipolase® or Palatase® concentrations and dsRNA targeting GFP in a water base as described in Table 15. The formulation was applied using the 1-step application protocol to the apical area of the two youngest emerged leaves. Three plants were treated for each enzymatic concentration.

TABLE 15

Water based formulation composition used in N. benthamiana 16C seedlings and results

| Base Formulation | Enzyme | Concentration (U/ml) | # of plants with suppression phenotype (n = 3) |
|---|---|---|---|
| Water | Lipolase ® | 200 | 2 |
| | | 400 | 3 |
| | | 800 | 1 |
| | Palatase ® | 200 | 3 |
| | | 400 | 3 |
| | | 800 | 3 |

The treatment with Palatase® enzyme resulted in three plants out of three with the suppression phenotype for each of the tested enzyme concentrations.

Example 11. Microbial Lysate Expressing a Cutinase, Lipase and/or a Plant Cell Wall Hydrolyzing Enzyme and dsRNA Trigger is Sufficient to Suppress a Transgene or Suppress Expression of an Endogenous Gene In this example, young *N. benthamiana* 16C, tomato or *Arabidopsis thaliana* seedlings (2-3 week old plants) are topically treated with a microbial lysate or liquid culture broth obtained from a phyto-pathogenic or saprophytic fungus or from a bacteria expressing cutinolytic (cutinase) and/or lipolytic (lipase) esterases and/or plant cell wall hydrolases, including but not limited to cellulases and pectinases, and dsRNA targeting transgenic GFP or the endogenous MgChl gene. The cutinolytic (cutinase) and/or lipolytic (lipase) esterases and/or plant cell wall hydrolases may be expressed naturally by the phyto-pathogenic or saprophytic fungus or the bacteria or may be expressed from a transgene. An example of a bacteria lysate or liquid culture broth includes, but is not limited to, lysate or liquid culture broth obtained from *Botrytis cinerea*. One or more of: an osmolyte, such as Mannitol and/or glycerol; a buffer, such as MES, PBS and/or Tris-HCl; a ribonuclease inhibitor, such as $Zn_2SO_4$ and/or RNAsin®; and a surfactant, such as Silwet® L77, Tween™-20, Triton™ X-100 and/or Nonanoic acid, may be added to the lysate or liquid culture broth.

The treatments with lysate or liquid culture broth containing the hydrolytic enzyme result in the suppression phenotype in the majority of the plants tested, indicating that the hydrolytic enzyme provided in microbial lysate or liquid culture broth is effective in delivering the dsRNA to a plant.

Example 12. Gene Suppression by Application of a dsRNA Polynucleotide in a Formulation with a Bio-Surfactant and a Lipase In this example, young *N. benthamiana* 16C, tomato, or *Arabidopsis thaliana* seedlings (2-3 week old plants) are topically treated with a dsRNA targeting transgenic GFP or the endogenous MgChl gene in a base formulation containing different bio-surfactants as described in Table 16 below, with either Palatase® or Lipolase® enzyme.

TABLE 16

Compositions comprising bio-surfactants used in *N. benthamiana* 16C, tomato and *Arabidopsis thaliana* seedlings

| Component group | Components | Concentration range |
|---|---|---|
| Base formulation - Osmolyte | Mannitol and/or glycerol | 25 to 200 mM |
| Base formulation - Buffer | MES (pH = 5.7) and/or PBS (pH = 7) and/or Tris-HCl (pH = 8) | 4-20 mM |
| Base formulation - Ribonuclease inhibitor | $Zn_2SO_4$ and/or RNAsin ® | 0.5 µM to 10 mM |
| Based formulation - Bio-surfactant | Surfactin from *Bacillus subtilis*, and/or di- and mono-rhamnolipids from *P. aeruginosa*, and/or 1',4'-Sophorolactone 6',6'-diacetate from *Candida* sp. | 0% to 0.5% |

TABLE 16-continued

Compositions comprising bio-surfactants used in *N. benthamiana* 16C, tomato and *Arabidopsis thaliana* seedlings

| Component group | Components | Concentration range |
|---|---|---|
| Hydrolytic enzymes | Palatase ® or Lipolase ® | 1000 to 6000 U/ml |
| Polynucleotide | MgChl (22 to 122 bp) and/or GFP dsRNA (22 to 124 bp) or bacterial lysate containing GFP dsRNA (660 bp) | 2 to 4 µg/µl for dsRNA |

The treatments with bio-surfactants together with Palatase® and/or Lipolase® in the formulation result in the suppression phenotype in the majority of the plants treated.

Example 13. Gene Suppression is Enhanced by the Addition of Specific Osmolytes in a Formulation with a Lipase In this example, young *N. benthamiana* 16C seedlings (2-3 week old plants) were topically treated with a dsRNA targeting transgenic GFP in a base formulation containing different osmolytes as described in Table 17 below, with or without Palatase® enzyme. The polynucleotide used was GFP dsRNA (124 bp) at a concentration of 2 µg/µL for each treatment. The formulation was applied using the 1-step application protocol to the apical area of the two youngest emerged leaves. Three plants were treated for each osmolyte. Plants were observed for development of suppression phenotype. All leaves were harvested from the plants at 10 day post-application and the suppression percentage was quantified using Image J image analysis software (an open platform for scientific image analysis available at: fiji.sc/Downloads#Fiji). This method quantifies the color discoloration area (representative of amount of silencing) as a percent, compared to the total leaf area.

TABLE 17

Compositions comprising osmolytes used in *N. benthamiana* 16C with Palatase ®

| Component/ Treatment | Palatase ® (U/mL) | Osmolyte (mM) | % Leaf area with GFP silencing |
|---|---|---|---|
| MES (pH = 5.7) | No enzyme | 0 | 0.00 |
| MES (pH = 5.7) | 500 | Mannitol 100 | 1.05 |
| MES (pH = 5.7) | 250 | Mannitol 100 + Sorbitol 25 | 0.25 |
| MES (pH = 5.7) | No enzyme | Mannitol 50 | 0.00 |
| MES (pH = 5.7) | No enzyme | Mannitol 100 | 0.10 |
| MES (pH = 5.7) | No enzyme | Sorbitol 50 | 0.10 |
| MES (pH = 5.7) | No enzyme | Sorbitol 100 | 1.90 |
| MES (pH = 5.7) | No enzyme | Glucose 50 | 0.22 |
| MES (pH = 5.7) | No enzyme | Glucose 100 | 0.08 |
| MES (pH = 5.7) | No enzyme | Glycerol 50 | 0.04 |
| MES (pH = 5.7) | No enzyme | Glycerol 100 | 0.00 |
| MES (pH = 5.7) | No enzyme | PEG400 50 | 0.00 |
| MES (pH = 5.7) | No enzyme | PEG400 100 | 0.00 |
| MES (pH = 5.7) | No enzyme | D-Proline 50 | 0.15 |
| MES (pH = 5.7) | No enzyme | D-Proline 100 | 0.59 |
| MES (pH = 5.7) | No enzyme | L-Proline 50 | 0.01 |
| MES (pH = 5.7) | No enzyme | L-Proline 100 | 0.29 |
| MES (pH = 5.7) | No enzyme | Betaine 50 | 0.88 |
| MES (pH = 5.7) | No enzyme | Betaine 100 | 0.02 |

The results indicated while a variety of osmolytes had some effect on GFP suppression, Sorbitol by itself had the strongest effect on suppression of GFP.

Example 14. Gene Suppression is Achieved with a Formulation Containing a Minimum of 80 mM Sorbitol and a Lipase In this example, Palatase® enzyme was dialyzed in PBS (pH 7.0) buffer and the protein concentration was determined. After dialysis, the Palatase® enzyme concentration in the solution was determined to be approximately ⅓ of the concentration of the initial commercial stock. The dialyzed Palatase® was then added to the base formulations at a volume equivalent to 1,500-4,500 U/mL of the commercial Palatase® enzyme to account for the dilution during the dialysis. Additionally, it was determined that the concentration of sorbitol in the commercial Palatase® was approximately 2400 mM and only about 3.86 mM sorbitol was present after dialysis. Young N benthamiana 16C seedlings (2-3 week old plants) were topically treated with a dsRNA targeting transgenic GFP in a base formulation containing different concentrations of the osmolyte Sorbitol as described in Table 18 below, with Palatase® enzyme or with dialyzed Palatase®. The polynucleotide used was GFP dsRNA (124 bp dsRNA) at a concentration of 2 µg/µL for each treatment. All formulations were in MES pH5.7 buffer. The formulation was applied using the 1-step application protocol to the apical area of the two youngest emerged leaves. Three plants were treated for each Sorbitol concentration. At ten days after the topical treatment, leaves of equal stage were harvested from each treated plant and quantified for percent GFP suppression compared to the total leaf area as described in Example 13.

TABLE 18

Compositions comprising Sorbitol with or without Palatase enzyme and results

| Enzyme (U/mL) | Sorbitol (mM) | % total leaf area with GFP silencing phenotype |
|---|---|---|
| Palatase ® 750 U/mL | 75 | 0.71 |
| No Palatase | 0 | 0.00 |
| No Palatase | 5 | 0.00 |
| No Palatase | 10 | 0.00 |
| No Palatase | 20 | 0.03 |
| No Palatase | 40 | 0.01 |
| No Palatase | 80 | 8.2 |
| No Palatase | 100 | 1.07 |
| No Palatase | 125 | 0.13 |
| Dialyzed Palatase 1500 U/mL | 0 | 0.01 |
| Dialyzed Palatase 1500 U/mL | 5 | 0.14 |
| Dialyzed Palatase 1500 U/mL | 10 | 0.02 |
| Dialyzed Palatase 1500 U/mL | 20 | 0.07 |
| Dialyzed Palatase 1500 U/mL | 40 | 0.00 |
| Dialyzed Palatase 1500 U/mL | 80 | 1.82 |
| Dialyzed Palatase 1500 U/mL | 100 | 0.86 |
| Dialyzed Palatase 1500 U/mL | 125 | 0.21 |
| Dialyzed Palatase 3000 U/mL | 100 | 6.71 |
| Dialyzed Palatase 4500 U/mL | 100 | 4.01 |
| Dialyzed Palatase 3000 U/mL | 0 | 0.00 |
| Dialyzed Palatase 4500 U/mL | 0 | 3.6 |

Suppression was observed in plants treated with only Sorbitol and without Palatase® enzyme. However, the most consistent suppression (all plants exhibited suppression) was seen when a combination of at least 80 mM Sorbitol and Palatase® were applied to the plants. The most effective combination for gene suppression appeared to be 3000 U/mL Palatase® with the addition of 100 mM Sorbitol. The experiment was repeated three additional times with similar results.

Example 15. The Non-Ionic Polysorbate Surfactant Tween-80 Enhances Activity of Palatase® Based Topical Applications In this example, young N. benthamiana 16C plants (2-3 weeks) were topically treated with dsRNA polynucleotide trigger (124 bp dsRNA trigger) targeting GFP in a formulation containing an osmolyte with or without a surfactant and emulsifier blend and with or without dialyzed Palatase® as described in Example 14. The surfactant:emulsifier used was Tween 80:Span 80 (both from Croda, Industrial Chemicals, USA). The formulation was applied using the 1-step protocol. The experiment and results are described in Table 19.

TABLE 19

Compositions comprising Tween80:Span80 with or without dialyzed Palatase enzyme

| Dialyzed Palatase (U/mL) | Sorbitol (mM) | Surfactant:Emulsifier blend | % Leaf area with GFP silencing |
|---|---|---|---|
| 0 | 0 | None | 0.00 |
| 0 | 0 | Tween 80 only | 0.00 |
| 0 | 0 | Tween80:Span80 @3:1 | 0.00 |
| 0 | 0 | Tween80:Span80 @3:1 | 0.00 |
| 0 | 0 | Tween80:Span80 @3:1 | 0.01 |
| 0 | 0 | Tween80:Span80 @3:1 | 0.00 |
| 0 | 80 | None | 0.70 |
| 0 | 80 | Tween 80 only | 1.50 |
| 0 | 80 | Tween80:Span80 @3:1 | 0.59 |
| 0 | 80 | Tween80:Span80 @3:1 | 0.04 |
| 0 | 80 | Tween80:Span80 @3:1 | 0.92 |
| 0 | 80 | Tween80:Span80 @3:1 | 1.43 |
| 4500 | 0 | None | 0.20 |
| 4500 | 0 | Tween 80 only | 0.17 |
| 4500 | 0 | Tween80:Span80 @3:1 | 0.00 |
| 4500 | 0 | Tween80:Span80 @3:1 | 0.01 |
| 4500 | 0 | Tween80:Span80 @3:1 | 0.04 |
| 4500 | 0 | Tween80:Span80 @3:1 | 0.00 |
| 4500 | 80 | None | 0.52 |
| 4500 | 80 | Tween 80 only | 4.21 |
| 4500 | 80 | Tween80:Span80 @3:1 | 5.11 |
| 4500 | 80 | Tween80:Span80 @3:1 | 2.30 |
| 4500 | 80 | Tween80:Span80 @3:1 | 2.19 |
| 4500 | 80 | Tween80:Span80 @3:1 | 4.13 |

The results indicated that suppression could be achieved using a minimal formulation with 80 mM Sorbitol, Tween80 and dialyzed commercial Palatase® enzyme. Similarly, a combination of surfactant:emulsifier in the presence of 80 mM Sorbitol and with the additional of dialyzed Palatase® was effective at producing a suppression phenotype.

Example 16. Gene Suppression of Herbicidal Gene Targets by Application of a dsRNA Polynucleotide Trigger In this example, young N benthamiana 16C plants (2-3 weeks) were topically treated with dsRNA polynucleotide triggers to herbicide target genes in a base formulation containing an osmolyte as described in Table 20 below, with commercial Palatase® enzyme. The surfactants tested were Tween-80 (Croda) or BREAK-THRU® SP131 or BREAK-THRU® SP133 (both from Evonik). The dsRNA polynucleotides tested target essential genes in plant biosynthetic pathways. Three separate genes were targeted, all from N benthamiana: 1.) Glycine decarboxylase (N.b. LDH1; a 150 bp dsRNA trigger), 2.) A 20s Protease (N.b.20sProt; a 153 bp dsRNA trigger), and 3.) Cellulose synthase (N.b.CesAl; a 148 bp dsRNA trigger). The dsRNA targeting the essential genes were applied either individually or in combination as outlined in Table 21. The formulation was applied using the 1-step protocol. Plants were observed for development of phenotype. Results are summarized in the third column of Table 21.

TABLE 20

Compositions comprising herbicide targets used in topical application of N. benthamiana 16C seedlings.

| Component group | Components | Concentration range |
|---|---|---|
| Base formulation - Surfactant | Tween-80 or BREAK-THRU® SP131 or BREAK-THRU® SP133 | 0.1-0.75% |
| Base formulation - Buffer | MES (pH = 5.7) | 4 mM |
| Hydrolytic enzymes | Palatase® | 750 U/ml |
| Polynucleotide | 1.) N.b.LDH1(150 bp) or 2.) N.b.20sProtease (153 bp) or 3.) N.b.CesA1 (148 bp) | 2 to 4 µg/µl dsRNA |

TABLE 21

Topical application of essential gene targets and results

| Surfactant type and concentration | Trigger | Total leaf area relative to GFP control |
|---|---|---|
| 0.75% Tween-80 | GFP | 100.0% |
| | LDH1 | 71.8% |
| | 20SPROT | 60.6% |
| | CESA1 | 65.4% |
| | LDH1/20SPROT | 62.2% |
| | LDH1/CESA1 | 66.3% |
| | 20SPROT/CESA1 | 56.2% |
| | LDH1/20SPROT/CESA1 | 61.7% |
| 0.1% BREAK-THRU® SP131 | GFP | 100.0% |
| | LDH1 | 114.2% |
| | 20SPROT | 120.0% |
| | CESA1 | 94.4% |
| | LDH1/20SPROT | 102.1% |
| | LDH1/CESA1 | 93.7% |
| | 20SPROT/CESA1 | 100.2% |
| | LDH1/20SPROT/CESA1 | 84.8% |
| 0.1% BREAK-THRU® SP133 | GFP | 100.0% |
| | LDH1 | 76.4% |
| | 20SPROT | 81.2% |
| | CESA1 | 91.3% |
| | LDH1/20SPROT | 82.8% |
| | LDH1/CESA1 | 115.8% |
| | 20SPROT/CESA1 | 101.2% |
| | LDH1/20SPROT/CESA1 | 99.0% |

All surfactants additions to the base formulation resulted in dramatic reduction of plant total leaf area, with the BREAK-THRU® SP131 and BREAK-THRU® SP133 surfactants being slightly more efficacious. An improved effect on leaf area reduction was observed when a combination of different dsRNAs targeting the plant essential genes was applied.

Example 17: Gene Suppression in the Presence of an Organo-Silicone Surfactant by Pre-Incubation of Lipase Enzyme with a Sorbitan-Fatty Acid Ester or a Non-Ionic Polysorbate Fatty Acid Ester Surfactant In this example, N. benthamiana 16C plants (2-3 weeks) were topically treated with a midmer dsRNA polynucleotide trigger (124 bp) targeting GFP. Commercial Palatase® stock was pre-incubated for 1 hour at room temperature in the presence of the components listed in Table 22. Following this pre-incubation step, the commercial Palatase® or the pre-incubated stock were added up to a concentration of 2,500 U·ml$^{-1}$ to a base formulation of 4 mM MES (pH=5.7), 4 mg·ml$^{-1}$ dsRNA trigger, and with the organosilicone super spreader surfactants Silwet L77 or Break-through S210 (BT-S210) at the concentrations listed on Table 22. Control formulations without enzyme contained 250 mM Sorbitol. A total volume of 300 µL of formulation was applied to either the adaxial and abaxial surface of the leaves of 3 seedlings per treatment using a hand held air brush sprayer at 20 PSI pressure at a distance of about 10 cm from the leaves. Plants were imaged under blue light 10 days after treatment and results reported as relative leaf area showing GFP silencing phenotype (% GFP).

TABLE 22

Palatase pre-incubation and base formulation composition and efficacy reported as relative leaf area (%) with GFP silencing phenotype

| Palatase ® pre-incubation mix | Palatase ® | Sorbitol | Surfactants | % GFP |
|---|---|---|---|---|
| | | 250 mM | | 0.0% |
| | | 250 mM | Silwet L77 @ 0.30% | 0.0% |
| | | 250 mM | Silwet L77 @ 0.45% | 0.0% |
| | 2500 U · ml$^{-1}$ | | | 0.0% |
| | 2500 U · ml$^{-1}$ | | Silwet L77 @ 0.30% | 0.0% |
| | 2500 U · ml$^{-1}$ | | Silwet L77 @ 0.45% | 0.6% |
| 0.05% Sorbitan mono-palmitate + 0.025% F127 | 2500 U · ml$^{-1}$ | | | 1.4% |
| 0.05% Sorbitan mono-palmitate + 0.025% F127 | 2500 U · ml$^{-1}$ | | Silwet L77 @ 0.15% | 0.0% |
| 0.05% Sorbitan mono-palmitate + 0.025% F127 | 2500 U · ml$^{-1}$ | | Silwet L77 @ 0.20% | 0.1% |

TABLE 22-continued

Palatase pre-incubation and base formulation composition and efficacy reported as relative leaf area (%) with GFP silencing phenotype

| Palatase ® pre-incubation mix | Palatase ® | Sorbitol | Surfactants | % GFP |
|---|---|---|---|---|
| 0.05% Sorbitan mono-palmitate + 0.025% F127 | 2500 U · ml$^{-1}$ | | Silwet L77 @ 0.30% | 2.9% |
| 0.05% Sorbitan mono-palmitate + 0.025% F127 | 2500 U · ml$^{-1}$ | | Silwet L77 @ 0.40% | 0.7% |
| 0.05% Sorbitan mono-palmitate + 0.025% F127 | 2500 U · ml$^{-1}$ | | Silwet L77 @ 0.45% | 0.5% |
| 0.10% Span ®80 | 2500 U · ml$^{-1}$ | | | 3.1% |
| 0.10% Span ®80 | 2500 U · ml$^{-1}$ | | Silwet L77 @ 0.15% | 0.0% |
| 0.10% Span ®80 | 2500 U · ml$^{-1}$ | | Silwet L77 @ 0.20% | 0.0% |
| 0.10% Span ®80 | 2500 U · ml$^{-1}$ | | Silwet L77 @ 0.30% | 1.7% |
| 0.10% Span ®80 | 2500 U · ml$^{-1}$ | | Silwet L77 @ 0.40% | 0.1% |
| 0.10% Span ®80 | 2500 U · ml$^{-1}$ | | Silwet L77 @ 0.45% | 2.7% |
| 0.05% Sorbitan mono-palmitate + 0.025% F127 | 2500 U · ml$^{-1}$ | | BT-S210 @ 0.55% | 0.0% |
| 0.10% Span ®80 | 2500 U · ml$^{-1}$ | | BT-S210 @ 0.55% | 3.7% |

The most efficacious suppression was observed in the presence of 0.1% Span®80 and 0.55% of the surfactant BT-S210.

In a separate experiment, N benthamiana 16C plants (2-3 weeks) were topically treated with a midmer dsRNA polynucleotide trigger (124 bp) targeting GFP. Commercial Palatase® stock (C-PAL) or a dialyzed commercial stock (D-PAL) were pre-incubated for 1 hr at room temperature in the presence of components listed on Table 23. Then, commercial Palatase® or the pre-incubated stock were added up to a concentration of 2,500 U·ml$^{-1}$ to a base formulation of 4 mM MES (pH=5.7), 3 mg·ml$^{-1}$ dsRNA trigger, and 0.3% of the organosilicone super spreader surfactant Silwet L77 (Table 2). D-PAL was added to the same base formulation at a volume equivalent to 3,500 or 7,500 U·ml$^{-1}$ of the C-PAL to account for lipase concentration dilution during dialysis process (Table 23). Control formulations without enzyme had 250 mM Sorbitol. Control formulation for pre-incubation mix without Palatase® received an equivalent volume of the pre-incubation mix as the treatments with pre-incubated C-PAL. A total of 500 μL of formulation was applied to the adaxial and abaxial surface of leaves of 3 seedlings per treatment using a hand held air brush sprayer at 20 PSI pressure at a distance of about 10 cm from seedlings leaves. Plants were imaged under blue light 10 days after treatment and results reported as relative leaf area showing GFP silencing phenotype (% GFP).

TABLE 23

Palatase pre-incubation and base formulation composition and efficacy reported as relative leaf area (%) with GFP silencing phenotype

| Palatase ® pre-incubation mix | Palatase ® | Sorbitol | Silwet L77 | % GFP |
|---|---|---|---|---|
| | C-PAL @ 2500 U · ml$^{-1}$ | | | 12.2% |
| | C-PAL @ 2500 U · ml$^{-1}$ | | 0.30% | 0.1% |
| 0.1% Span ®80 | C-PAL @ 2500 U · ml$^{-1}$ | | | 10.6% |
| | | 250 mM | 0.30% | 0.0% |
| 0.1% Span ®80 | | 250 mM | 0.30% | 0.0% |
| 0.1% Span ®80 | C-PAL @ 2500 U · ml$^{-1}$ | | 0.30% | 0.2% |
| 0.1% Span ®80 | D-PAL @ 3750 U · ml$^{-1}$ | 250 mM | 0.30% | 0.5% |
| 0.1% Span ®80 | D-PAL @ 7500 U · ml$^{-1}$ | 250 mM | 0.30% | 4.0% |

The addition of 0.1% Span®80 to commercial or dialyzed enzyme provided the best suppression effect.

Example 18: Gene Suppression is Enhanced by Formulations Containing a Xanthan Gum and a Fungal Phospholipase A1

In this example, N. benthamiana 16C plants (2-3 weeks of age) were topically treated with 2 midmer dsRNA polynucleotide triggers, one targeting GFP and the other the endogenous Magnesium chelatase (MgChl) gene. In addition to the components detailed in Table 24, all formulations used to deliver this mixture of triggers also contained 4 mM MES buffer (pH=5.7) and 1 mM of Retro-2, an endosomal release agent (Sigma). Lipases used included in these formulations included commercially available Palatase® (C-PAL), Amano® lipase G (AL-G), Thermomyces lanuginosus Phospholipase A1 (Tl-PLA1) and the diatomaceous earths immobilized Amano® lipase PS (iAL-PS, from Burkholderia cepacia). Commercial xanthan gum (XG) was used at concentrations ranging from 0% to 0.2%. A total of 400 μl of formulation was applied to 4 seedlings per treatment using a hand held air brush sprayer at 20 PSI pressure at a distance of about 10 cm from seedlings leaves. Plants were imaged under blue and white light 11 days after treatment.

TABLE 24

Formulation composition and efficacy reported as % relative leaf area showing either MgChl or GFP silencing phenotype

| Enzyme(s) | iAL-PS | Sorbitol | SMP::F127 | XG | % GFP | % MgChl |
|---|---|---|---|---|---|---|
| C-PAL + AL-G each @ 1500 U · ml$^{-1}$ | 0 mg · ml$^{-1}$ | 0 mM | 1.0%:0.5% | 0.00% | 0.0 | 0.0 |
| C-PAL + AL-G each @ 1500 U · ml$^{-1}$ | 10 mg · ml$^{-1}$ | 0 mM | 1.0%:0.5% | 0.00% | 2.5 | 0.8 |
| C-PAL + AL-G each @ 1500 U · ml$^{-1}$ | 10 mg · ml$^{-1}$ | 0 mM | 1.0%:0.5% | 0.05% | 5.8 | 1.4 |
| C-PAL + AL-G each @ 1500 U · ml$^{-1}$ | 10 mg · ml$^{-1}$ | 0 mM | 1.0%:0.5% | 0.10% | 5.3 | 1.6 |
| C-PAL + AL-G each @ 1500 U · ml$^{-1}$ | 10 mg · ml$^{-1}$ | 0 mM | 1.0%:0.5% | 0.20% | 6.2 | 2.2 |
| Tl-PLA1 @ 250 U · ml$^{-1}$ | 0 mg · ml$^{-1}$ | 150 mM | 1.0%:0.5% | 0.00% | 0.0 | 0.0 |
| Tl-PLA1 @ 250 U · ml$^{-1}$ | 10 mg · ml$^{-1}$ | 150 mM | 1.0%:0.5% | 0.00% | 4.6 | 2.7 |
| Tl-PLA1 @ 250 U · ml$^{-1}$ | 10 mg · ml$^{-1}$ | 150 mM | 1.0%:0.5% | 0.05% | 12.5 | 4.0 |
| Tl-PLA1 @ 250 U · ml$^{-1}$ | 10 mg · ml$^{-1}$ | 150 mM | 1.0%:0.5% | 0.10% | 17.6 | 5.8 |
| Tl-PLA1 @ 250 U · ml$^{-1}$ | 10 mg · ml$^{-1}$ | 150 mM | 1.0%:0.5% | 0.20% | 10.6 | 6.9 |

The most efficacious suppression was observed in formulations containing 0.2% xantham gum. In addition to xantham gum, formulations containing, *Thermomyces lanuginosus* Phospholipase A1 (Tl-PLA1) used in conjunction with diatomaceous earth immobilized Amano® lipase PS (iAL-PS, from *Burkholderia cepacia*) provided suppression.

Example 19: Gene Suppression is Enhanced by Formulations Containing a Phospholipase A1 or a Mix of Phospholipase A1 and Lipase In this example, *N. benthamiana* 16C plants (2-3 weeks old seedlings) were topically treated with a combination of 2 midmer dsRNA polynucleotide triggers, one targeting GFP and the other the endogenous Magnesium chelatase (MgChl) gene. In addition to the components detailed on Table 25, all formulations used to deliver this trigger mix contained 4 mM MES buffer (pH=5.7), 10 mg·ml$^{-1}$ immobilized Amano lipase PS and 0.15% xanthan gum. Lipases used included a commercially available *Thermomyces lanuginosus* Phospholipase A1 at 550 u·ml$^{-1}$ and a PBS buffer dialyzed commercial Palatase® stock (D-PAL, 1X=0.137 mg total protein·ml$^{-1}$). A total of 400 µl of formulation was applied to 4 seedlings per treatment using a hand held air brush sprayer at 20 PSI pressure at a distance of about 10 cm from seedlings leaves. Plants were imaged under blue and white light 11 days after treatment.

TABLE 25

Formulation composition and efficacy reported as % relative leaf area showing either MgChl or GFP silencing phenotype

| Enzyme(s) | Sorbitol | CaCl$_2$ | SMP | Surfactant | % GFP | % MgChl |
|---|---|---|---|---|---|---|
| No | 150 mM | 0 mM | 0.375% | 0.375% Tween®40 | 0.6 | 0.1 |
| No | 150 mM | 0 mM | 0.375% | 0.375% Tween®60 | 3.2 | 0.8 |
| No | 150 mM | 0 mM | 0.375% | 0.375% Tween®80 | 0.6 | 0.1 |
| No | 150 mM | 2 mM | 0.375% | 0.375% Tween®40 | 0.8 | 0.1 |
| No | 150 mM | 2 mM | 0.375% | 0.375% Tween®60 | 1.5 | 0.2 |
| No | 150 mM | 2 mM | 0.375% | 0.375% Tween®80 | 1.2 | 0.2 |
| No | 150 mM | 4 mM | 0.375% | 0.375% Tween®40 | 8.0 | 1.6 |
| No | 150 mM | 4 mM | 0.375% | 0.375% Tween®60 | 0.7 | 0.1 |
| No | 150 mM | 4 mM | 0.375% | 0.375% Tween®80 | 0.3 | 0.0 |
| No | 150 mM | 8 mM | 0.375% | 0.375% Tween®40 | 0.1 | 0.0 |
| No | 150 mM | 8 mM | 0.375% | 0.375% Tween®60 | 0.1 | 0.0 |
| No | 150 mM | 8 mM | 0.375% | 0.375% Tween®80 | 0.0 | 0.0 |
| Tl-PLA1 | 0 mM | 0 mM | 0.375% | 0.375% Tween®40 | 8.9 | 2.2 |
| Tl-PLA1 | 0 mM | 0 mM | 0.375% | 0.375% Tween®60 | 1.9 | 0.4 |
| Tl-PLA1 | 0 mM | 0 mM | 0.375% | 0.375% Tween®80 | 9.9 | 3.1 |
| Tl-PLA1 + 1X D-PAL | 0 mM | 0 mM | 0.375% | 0.375% Tween®40 | 8.2 | 2.0 |

TABLE 25-continued

Formulation composition and efficacy reported as % relative leaf area showing either MgChl or GFP silencing phenotype

| Enzyme(s) | Sorbitol | CaCl$_2$ | SMP | Surfactant | % GFP | % MgChl |
|---|---|---|---|---|---|---|
| Tl-PLA1 + 2X D-PAL | 0 mM | 0 mM | 0.375% | 0.375% Tween ®40 | 9.1 | 2.2 |
| Tl-PLA1 | 0 mM | 2 mM | 0.375% | 0.375% Tween ®40 | 5.0 | 1.1 |
| Tl-PLA1 | 0 mM | 2 mM | 0.375% | 0.375% Tween ®60 | 4.6 | 1.1 |
| Tl-PLA1 | 0 mM | 2 mM | 0.375% | 0.375% Tween ®80 | 3.4 | 0.6 |
| Tl-PLA1 + 1X D-PAL | 0 mM | 2 mM | 0.375% | 0.375% Tween ®40 | 3.3 | 1.0 |
| Tl-PLA1 + 2X D-PAL | 0 mM | 2 mM | 0.375% | 0.375% Tween ®40 | 5.5 | 1.4 |
| Tl-PLA1 | 0 mM | 4 mM | 0.375% | 0.375% Tween ®40 | 1.0 | 0.2 |
| Tl-PLA1 | 0 mM | 4 mM | 0.375% | 0.375% Tween ®60 | 1.9 | 0.3 |
| Tl-PLA1 | 0 mM | 4 mM | 0.375% | 0.375% Tween ®80 | 3.3 | 1.1 |
| Tl-PLA1 + 1X D-PAL | 0 mM | 4 mM | 0.375% | 0.375% Tween ®40 | 14.2 | 4.3 |
| Tl-PLA1 + 2X D-PAL | 0 mM | 4 mM | 0.375% | 0.375% Tween ®40 | 10.0 | 2.9 |
| Tl-PLA1 | 0 mM | 8 mM | 0.375% | 0.375% Tween ®40 | 5.3 | 0.9 |
| Tl-PLA1 | 0 mM | 8 mM | 0.375% | 0.375% Tween ®60 | 1.1 | 0.2 |
| Tl-PLA1 | 0 mM | 8 mM | 0.375% | 0.375% Tween ®80 | 0.2 | 0.0 |
| Tl-PLA1 + 1X D-PAL | 0 mM | 8 mM | 0.375% | 0.375% Tween ®40 | 2.1 | 0.5 |
| Tl-PLA1 + 2X D-PAL | 0 mM | 8 mM | 0.375% | 0.375% Tween ®40 | 13.3 | 3.6 |

On average, treatments that included a phospholipase A1 or mix of lipase and phospholipase A1 (enzyme plus osmolyte) showed a 3.9× and 5.5× greater leaf area silencing of GFP and MgChl respectively over formulations containing equivalent levels of osmolyte only.

Example 20: Delivery of dsRNA to *Amaranthus palmeri* Plants Using a Liquid Formulation with Lipase Enzymes In this example, young *Amaranthus palmeri* or *Amarnthus cruentus* plants (2-3 week old plants) were treated with a formulation containing a short dsRNA targeting Magnesium chelatase (MgChl) or as a negative control a dsRNA targeting GFP in buffer solution consisting of 150 mM proline, 4 mM MES (pH 5.7) or 50 mM sucrose, 4 mM MES (pH 5.7). Additional components were 510 U/mL lipolase from a stock containing >100,000 U/ml Lipolase® 100,000 U/g (Sigma L0777), 50 mg/ml Amano lipase PS-IM (immobilized on diatomaceous earth) (Aldrich 709603) with 0.75% xanthan gum from *Xanthomonas campestris* (Sigma G1253), and a surfactant (0.75% sorbitan monopalmitate (Aldrich388920) in 0.375% F127 (Pluronic® F-127 Sigma 2443) and 0.25% Tween®80) or 0.04% Silwet L-77 as illustrated in Table 26 below.

TABLE 26

Formulations and the delivery methods applied to the young treated plants. Each treatment consisted of 4 plants.

| Treatment # | osmolyte | cuticle enzymes | Surfactant | Species used | Application method: 2 step? |
|---|---|---|---|---|---|
| 1 | sucrose | None | 0.04% Silwet L-77 | both | yes |
| 2 | sucrose | | | | yes |
| 3 | sucrose | Lipolase ® ~510 U/ml | | palmeri | no |
| 4 | sucrose | plus Amano lipase PS-IM | | palmeri | no |
| 5 | proline | Lipolase ® ~510 U/ml | 0.375% SMP and 2.5% Tween80 | palmeri | no |
| 6 | proline | plus Amano lipase PS-IM | | palmeri | no |

Formulations were applied to plant leaves using a 1-step method, whereby components were first mixed together, incubated for 1 hour and then sprayed onto two leaves and the apical meristem of each plant. 200 ul was sprayed on with an art brush gravity fed sprayer at 20 psi on to four plants. The air brush was held about 1 to 2 cm above the leaf surface while spraying.

A second delivery method employed 2-steps where the formulation was gently dropped on to the leaves with a pipette. The formulation was spread gently over the top of the leaf with the side of the pipet tip, allowed to dry and then the surface of the leaves were gently abraded with a cotton swab coated with 360 mesh silicon carbide particles. In this method, 10 ul of the formulation was applied to leaves 3 and 4 and the meristem of each of four plants.

seen in both application methods at 2 DAT. Based on the number of plants that exhibited localized suppression of MgChl, it's earlier visibility and stronger suppression it appeared that the 2-step application method was trending more effective in delivering the polynucleotide to the plant cells in order to initiate suppression.

Example 21. A Combination of Enzymatic and Particle Assisted Delivery is Effective at Delivering dsRNA to *Amaranthus palmeri* Plants In this example, young *Amaranthus palmeri* plants (3-4 week old) were treated with dsRNA polynucleotide targeting the Magnesium Chelatase (MgChl) gene sequence (54 bp in length) and the plants were observed for development of a

TABLE 27

Compositions of the formulations applied to *Amaranath* plants

| Treatment # | mM L proline | amanolipase PS-IM on diat earth at 50 mg/ml stock with 0.75% xanthan gum | Final units/ml Lipolase | mM MES pH 5.7 | Trigger at 4 µg/uL | % silwet L-77 | Mixed SMP and Tween ® 80 Surfactant | Application method |
|---|---|---|---|---|---|---|---|---|
| 1 | | | | | MgChl | 0.04 | | 2-step |
| 2 | | | | | GFP | 0.04 | | 2-step |
| 3 | | 50 | 510 | | MgChl | 0.04 | | 1-step |
| 4 | | 50 | 510 | | GFP | 0.04 | | 1-step |
| 5 | 150 | 50 | 510 | 4 | MgChl | | yes | 1-step |
| 6 | 150 | 50 | 510 | 4 | GFP | | yes | 1-step |

Plants were observed for phenotype development at 1, 2, 5, and 7 days after treatment (DAT). Suppression of MgChl expression was visible as early as 1 DAT in the 2 step application method as evidenced by yellow spots showing in green chlorophyll under white light. MgChl suppression was easily visible at 2 DAT on the 2-step and 1-step plants treated with the respective trigger. There was no yellowing on any plant treated with the GFP trigger on any of the days after treatment. Table 28 summarizes the localized MgChl suppression observed in the treated plants.

chlorotic phenotype indicative of gene suppression. The plants were propagated in a growth chamber held at 25° C. with a 16 hour day length regime. Plants were treated either with a liquid formulation containing Palatase® enzyme or by abrasion of the plant abaxial surface, a method termed Particle Assisted Delivery (PAD). For the PAD method of delivery a spray suspension of 2.5 mg/mL of dsRNA in a mixture of 20 mg/mL of a 1:1 mixture of Celite 512 and 360 grit Silicon Carbide particles (C512/360SiC) was applied to the plants. Similarly, the two delivery methodologies were

TABLE 28

Suppression of MgChl expression in *Amaranth* spp.

| Treatment # | mM sucrose | amanolipase PS-IM on diat earth at 50 mg/ml stock with 0.75% xanthan gum | Final units/mL Lipolase | mM MES pH 5.7 | Trigger | % silwet L-77 | Mixed SMP and Tween ® 80 Surfactant | Application method | # of plants (out of 4) showing silencing/strength of silencing | | | |
|---|---|---|---|---|---|---|---|---|---|---|---|---|
| | | | | | | | | | Day 1 | Day 2 | Day 5 | Day 7 |
| 1 | 50 | | | | MgChl | 0.04 | | 2-step | 3, very slight | 4, moderate | 4, strong | 4, strong |
| 2 | 50 | | | | GFP | 0.04 | | 2-step | 0, none | 0, none | 0, none | 0, none |
| 3 | 50 | 50 | 510 | | MgChl | 0.04 | | 1-step | 0, none | 4, slight | 4, slight | 4, moderate |
| 4 | 50 | 50 | 510 | | GFP | 0.04 | | 1-step | 0, none | 0, none | 0, none | 0, none |
| 5 | | 50 | 510 | 4 | MgChl | | yes | 1-step | 0, none | 4, slight | 4, moderate | 4, moderate |
| 6 | | 50 | 510 | 4 | GFP | | yes | 1-step | 0, none | 0, none | 0, none | 0, none |

Plants treated with the 2-step application method developed localized suppression symptoms that were barely visible as early as 1 DAT. The MgChl suppression was clearly combined in what is termed enzymatic-Particle Assisted Delivery (e-PAD). In both the PAD and e-PAD methods the spray suspension slurry was in a base formulation containing 4 mM MES (pH 5.7). Additionally, the osmolytes mannitol or sorbitol were added to the dsRNA solution in a base solution containing either Silwet L-77 (0.1% vol/vol) or Tween 80 (0.75% vol/vol) as outlined in Table 29. The results were scored at seven days after treatment. The experiment was repeated five times.

TABLE 29

Compositions comprising applications of dsRNA, osmolytes, surfactants and enzyme-particle mixtures in *Amaranthus palmeri* and results.

| Treatment | dsRNA | Osmolyte (mM) | Palatase (U/mL) | % Surfactant (vol/vol) | Phenotype (5 Reps) |
|---|---|---|---|---|---|
| 1 | MgChl | 0 | 0 | Silwet L77 (0.1) | 5/5 |
| 2 | MgChl | 0 | 0 | Silwet L77 (0.1) | 3/5 |
| 3 | MgChl | Mannitol (75) | 0 | Silwet L77 (0.1) | 5/5 |
| 4 | MgChl | Sorbitol (75) | 0 | Silwet L77 (0.1) | 4/5 |
| 5 | MgChl | 0 | 325 | Silwet L77 (0.1) | 2/5 |
| 6 | MgChl | 0 | 625 | Silwet L77 (0.1) | 2/5 |
| 7 | MgChl | 0 | 925 | Silwet L77 (0.1) | 0/5 |
| 8 | MgChl | 0 | 325 | Tween 80 (0.75) | 3/5 |
| 9 | MgChl | 0 | 625 | Tween 80 (0.75) | 2/5 |
| 10 | MgChl | 0 | 925 | Tween 80 (0.75) | 2/5 |

The combination of mannitol or sorbitol and Particle Assisted Delivery (PAD) gave the best response in terms of observed leaf chlorosis. A higher dose of Palatase did not seem to be more effective in symptom development. Tween 80 surfactant appeared to have a slightly better trend in effecting symptoms than Silwet L-77.

Example 22. Particulate-Assisted Delivery of Trigger Polynucleotides Using Aluminum Oxide Particles This example illustrates non-limiting embodiments of methods, apparatuses, and compositions useful for delivering a nucleic acid into a plant or cells or tissues of a plant. More specifically, this example describes silencing a target gene by way of particulate-assisted delivery of a nucleic acid such as an RNA "trigger" or silencing element into a plant. The methods generally involve treatment of the surface of a plant (or of plant cells or tissues) with an abrasive or particulate, and with a nucleic acid.

In this example, four dsRNA "triggers" (silencing elements) of 50, 78, 124, and 249 base-pairs (bp), and targeting green fluorescent protein (GFP) were used to silence the GFP gene in a transgenic *Nicotiana benthaminiana* line (16c) expressing GFP. For each trigger, 420 micrograms of total RNA were dissolved in 210 microliters; 10 microliters were removed for later analysis and the remaining 200 microliters was added to 200 milligrams of aluminum oxide (~220 mesh) particles in a 15 milliliter culture tube. The preparation was incubated overnight at 37 degrees Celsius, then centrifuged at 250 rpm with the cap off. One milliliter of 100% ethanol was added to transfer the RNA-coated aluminum oxide particles into a weighing tray; excess liquid was removed by pipette and the particles allowed to air-dry. Each preparation of the dry particles was loaded into the chamber of an airbrush and sprayed at 45-65 pounds per square inch (psi) onto a single leaf of each of six plants. Local silencing in the treated leaf was observed in 3 of the 6 plants sprayed with the 124 bp dsRNA trigger, but not in the plants treated with the 50 or 78 bp dsRNA triggers. No silencing was observed in plants treated with the 249 bp dsRNA trigger but these results were not considered based on subsequent analysis of trigger quality. Systemic GFP silencing (outside of the treated leaves) was not observed in this experiment.

Example 23. Particulate-Assisted Delivery of Trigger Polynucleotides Using Aluminum Oxide Particles This example illustrates non-limiting embodiments of methods, apparatuses, and compositions useful for delivering a nucleic acid into a plant or cells or tissues of a plant. More specifically, this example describes silencing a target gene by way of particulate-assisted delivery of a nucleic acid such as an RNA "trigger" or silencing element into a plant.

In another example, 1500 micrograms of dsRNA trigger in 1 milliliter water was added to 200 milligrams of aluminum oxide (320 mesh (20.1-23.1 micrometers) or 400 mesh (15.5-17.5 micrometers)) in a 6-well plate and incubated overnight at room temperature on a shaker (150 rpm). One milliliter of 100% ethanol was added to transfer the RNA-coated aluminum oxide particles into a weighing tray; excess liquid was removed by pipette and the particles allowed to air-dry. Each preparation of the dry particles was loaded into the chamber of an airbrush and sprayed at 55 pounds per square inch (psi) onto leaves of nine transgenic *Nicotiana benthaminiana* 16c plants. Results are provided in Table 30. Local silencing in the treated leaf was observed in nearly all plants treated with the GFP dsRNA trigger, with less efficient GFP silencing observed in the plants treated with the GFP/PDS fusion dsRNA trigger (which contains the intact sequence of the GFP dsRNA trigger at its 3' end). The larger particle size (320 mesh) provided better silencing efficiency than the smaller particles (400 mesh). Systemic GFP silencing (outside of the treated leaves) was not observed in this experiment.

TABLE 30

| dsRNA trigger size (base pairs) | Target gene | Aluminum oxide mesh size | Number of plants where GFP silencing was observed |
|---|---|---|---|
| 124 | GFP | 320 | 9/9 |
| 124 | GFP | 400 | 7/9 |
| 300 | GFP/PDS fusion | 320 | 5/9 |
| 300 | GFP/PDS fusion | 400 | 2/9 |

Example 24. Systemic Silencing of Target Gene by Particulate-Assisted Delivery of a Nucleic Acid Using Aluminum Oxide or Silicon Carbide Particles This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as an RNA "trigger" or silencing element into a plant.

In another example, 1.5 milligrams of total RNA (124 bp dsRNA) were coated onto aluminum oxide or silicon carbide particles and applied using an airbrush spray (65 psi) onto 9 two- to three-week-old transgenic *Nicotiana* benthaminiana 16c plants. Phenotype was recorded 17 days after the treatment. Plants showing GFP silencing (red spots/sectors under ultraviolet light) on sprayed leaves only were scored as displaying local silencing. Plants additionally showing GFP silencing (red spots/sectors under ultraviolet light) in parts of the plants other than the sprayed leaves were scored as displaying systemic silencing; in this experiment the systemic silencing was observed as a vasculature-associated GFP silencing pattern in newly grown leaves. Results are provided in Table 31.

TABLE 31

| Particulate type | Particulate mesh size | Number of plants displaying local silencing | Number of plants displaying systemic silencing | Number of plants displaying no silencing |
|---|---|---|---|---|
| $Al_2O_3$ | 320 | 8/9 | 1/9 | 0/9 |
| $Al_2O_3$ | 360 | 7/9 | 1/9 | 1/9 |
| SiC | 320 | 8/9 | 1/9 | 0/9 |
| SiC | 360 | 6/9 | 3/9 | 0/9 |

Example 25. Systemic Silencing of Target Gene by Particulate-Assisted Delivery of a Nucleic Acid Using Silicon Carbide Particles This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as an RNA "trigger" or silencing element into a plant.

In another example, different RNA triggers designed to silence GFP were compared. Several triggers were blunt-ended dsRNAs; one was a single-stranded miRNA precursor transcript designed to self-hybridize and be processed to produce a mature miRNA targeting GFP. For each RNA trigger, 1.5 milligrams of total RNA were coated onto SiC particles. Each individual RNA trigger was dissolved in water to make up 1 milliliter, added to 200 milligrams SiC (320 mesh) in a well of a 6-well plate. The plate was placed in a fume hood to air-dry with gentle shaking. After the plate was completely dry, 100% ethanol was added to transfer the RNA-coated SiC particles into a weighing tray; excess liquid was removed by pipette and the particles allowed to air-dry overnight. The dried RNA-coated particles were transferred to 2-milliliter microcentrifuge tubes, ground briefly in the tubes, and applied using an airbrush spray (60 psi) onto 9 three-week-old transgenic Nicotiana benthaminiana 16c plants. Local silencing was observed beginning at 4-5 days after treatment. Phenotype was recorded at 9 days (for local silencing) and at 19 days (for systemic silencing) after treatment. In this experiment, systemic silencing was again observed as a vasculature-associated GFP silencing pattern in newly grown leaves. Results are provided in Table 32.

TABLE 32

| dsRNA trigger size (base pairs) | Target gene | Number of plants displaying local silencing | Number of plants displaying systemic silencing | Number of plants displaying no silencing |
|---|---|---|---|---|
| 50 | GFP | 4/9 | 0/9 | 5/9 |
| 78 | GFP | 8/9 | 2/9 | 1/9 |
| 124 | GFP | 9/9 | 5/9 | 0/9 |
| 125 | GFP | 4/9 | 0/9 | 5/9 |
| 249 | GFP | 3/9 | 0/9 | 6/9 |
| 355 | GFP | 1/9 | 0/9 | 8/9 |
| 258 | PDS | 0/9 | 0/9 | 9/9 |
| — | (none) | 0/9 | 0/9 | 9/9 |
| — | (none) | 0/9 | 0/9 | 9/9 |

Example 26. Particulate-Assisted Delivery of a DNA Viral Vector

This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as DNA viral vector into a plant.

A viral vector was used to silence either a green fluorescent protein (GFP) transgene or an endogenous phytoene desaturase (PDS) target gene in treated plants. Plasmid A1 targeting PDS or plasmid A2 targeting GFP was combined with plasmid B (ToGMoV DNA-B in the pUC19 vector) to produce a VIGS system. 250 micrograms of either plasmid A1 or plasmid A2 was added to 250 micrograms plasmid B in 600 microliters water. The DNA mixtures were each added to 150 milligrams of aluminum oxide particles (400 mesh or 600 mesh) in wells of a 6-well plate and incubated overnight at room temperature on a shaker (150 rpm) in a fume hood to air dry. After the plate was completely dry, 1 milliliter of 70% ethanol was added to transfer the RNA-coated aluminum oxide particles into a weighing tray; excess liquid was removed by pipette and the particles allowed to air-dry. Each preparation of the dried DNA-coated particles was applied using an airbrush spray (55 psi) onto six transgenic Nicotiana benthaminiana 16c plants. Results are shown in Table 33. The results demonstrate that particle-assisted delivery of a viral vector results in systemic silencing of transgenes or endogenous genes expressed in a whole plant. This technique is useful in other applications, such as in virus resistance assays, as the method does not involve Agrobacterium-mediated infection.

TABLE 33

| Plasmid ID | Target gene | Aluminum oxide mesh size | Number of plants displaying systemic PDS silencing | Number of plants displaying systemic GFP silencing |
|---|---|---|---|---|
| A1 | PDS | 400 | 5/6 | — |
| A2 | GFP | 400 | — | 4/6 |
| A1 | PDS | 600 | 1/6 | — |
| A2 | GFP | 600 | — | 6/6 |

Example 27. Systemic Silencing of Target Gene by Abrasion of a Plant Surface This example illustrates non-limiting embodiments of methods, apparatuses, and compositions useful for delivering a nucleic acid into a plant or cells or tissues of a plant. More specifically, this example describes systemic silencing of a target gene by way of abrasion of a plant surface with particulates to disrupt the cuticle or epidermis, thereby delivering a nucleic acid such as an RNA "trigger" or silencing element into a plant.

Double-stranded RNA was labelled with Cy3 as a fluorescent marker and coated onto SiC particles (320 mesh) which were then sprayed onto a leaf. The leaf was imaged with confocal fluorescence microscopy 1 day after treatment. The images obtained showed that the fluorescently labelled particles were located at the bottom of "craters" formed by the particle impact some layers deep in the leaf epidermis and suggested that, while most of the fluorescence was still associated with the particles, some of the fluorescence diffused into adjacent undamaged cells. The images suggest that the nucleic acid on the particles is not delivered directly into cells in the manner seen with gene gun delivery using much smaller particles, but by diffusion into cells adjacent to the larger particles used here with relatively low-pressure delivery.

Example 28. Comparison of Varying Distances Between Airbrush Nozzle and Plant Surface This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as an RNA "trigger" or silencing element into a plant.

This experiment compared varying distances between airbrush nozzle and plant surface. 1.5 milligrams of blunt-ended dsRNA targeting GFP was coated onto 100 milligrams of silicon carbide (360 mesh) and air dried overnight. After drying, the mixture was ground to singulate the particles, and loaded into a G78 airbrush mounted to a ring stand. Transgenic *Nicotiana benthaminiana* 16c plants were each sprayed with three 1-second bursts at 3, 5, and 7 centimeters nozzle-to-leaf distance). Phenotype (GFP silencing) was visually assessed using blue light excitation 7 days after treatment. In addition, GFP expression was quantified in the red (silenced) and green (non-silenced) sectors using qPCR. Results: the 3-centimeter spray distance damaged the plants and resulted in little silencing; approximately equivalent silencing was observed with the 5- and 7-centimeter spray distances. The qPCR measurements demonstrated that GFP expression was correlated to visual phenotype (FIG. 1).

Example 29. Sequential Application of RNA and Particulate Abrasive

This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as an RNA "trigger" or silencing element into a plant.

An experiment to test sequential application of RNA and particulate abrasive was performed. Blunt-ended dsRNA targeting GFP was dissolved in water at 1, 5, and 10 milligrams/milliliter, with a silicone surfactant (0.1% Silwet L77) added to aid spreading on the leaf surface. 20 microliters of the RNA solution was applied to three leaves of transgenic *Nicotiana benthaminiana* 16c plants and allowed to dry briefly. Dry uncoated silicon carbide (360 mesh) particles were sprayed onto the RNA-coated leaves at 60 psi using a G78 airbrush mounted to a ring stand at 5 centimeters nozzle-to-leaf distance from the plants. GFP silencing was assessed visually using blue light excitation at 7 days after treatment. Leaf damage prevented full interpretation of the dsRNA rate data, but GFP silencing was observed using this sequential method, where applying an RNA to the surface of the plant is followed by abrading the surface of a plant with a particulate of a size greater than about 2.5 micrometers.

Example 30. Comparison of the Silencing Efficiency of a Single-Step Application of RNA-Coated Particulates and a Two-Step Sequential Application This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as an RNA "trigger" or silencing element into a plant.

This experiment compared the silencing efficiency of a single-step application of RNA-coated particulates and a two-step sequential application. The effects of mannitol and a surfactant were also examined.

For single-step application of dry, RNA-coated particulates, 1.5 milligrams of a blunt-ended dsRNA trigger targeting GUS or of a blunt-ended dsRNA trigger targeting GFP were dissolved in either water or 200 millimolar mannitol. 100 milligrams SiC particles (360 mesh) were added to the RNA solutions, and the mixture was air dried overnight. The dry RNA-coated particles were sprayed at 60 psi in three 1-second bursts onto the leaves of transgenic *Nicotiana benthaminiana* 16c plants using a G78 airbrush mounted to a ring stand at 5 centimeters nozzle-to-leaf distance from the plants. For two-step sequential application, the dsRNA triggers were dissolved in water, with or without 0.2% Silwet L77, and with or without 200 millimolar mannitol. Twenty microliters of RNA solution was applied to each of three leaves of transgenic *Nicotiana benthaminiana* 16c plants and allowed to dry briefly. Dry uncoated silicon carbide (360 mesh) particles were sprayed onto the RNA-coated leaves at 60 psi using a G78 airbrush mounted to a ring stand at 5 centimeters nozzle-to-leaf distance from the plants. GFP silencing was assessed visually using blue light excitation at 7 days after treatment. The silencing frequency of dry coated particles and sequential application was found to be approximately the same. The addition of mannitol had no effect in the single-step application of dry, RNA-coated but had a positive effect on the two-step sequential application, by apparent reduction in leaf damage.

Example 31. Comparison of the Silencing Efficiency of Different Particulate Abrasives in a Two-Step Sequential Application Method This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as an RNA "trigger" or silencing element into a plant.

This experiment compared the silencing efficiency of different particulate abrasives in a two-step sequential application method, where applying an RNA to the surface of the plant is followed by abrading the surface of a plant with a particulate of a size greater than about 2.5 micrometers.

Particulate abrasives tested included silicon carbide (SiC, angular), aluminum oxide ($Al_2O_3$, angular), soda lime glass ("SLG", round) and diatomaceous silica ("diatomaceous earth", "DE", angular) particles with various size ranges. Non-limiting examples of particulate abrasives useful in the methods and compositions disclosed herein are provided in Table 34 below.

TABLE 34

| Abrasive | Composition | Median Size (micrometers) |
|---|---|---|
| 280 mesh SiC | silicon carbide | 33.0-36.0 |
| 320 mesh SiC | silicon carbide | 26.3-29.2 |
| 360 mesh SiC | silicon carbide | 20.1-23.1 |
| 400 mesh SiC | silicon carbide | 15.5-17.5 |
| 500 mesh SiC | silicon carbide | 11.3-13.3 |
| 600 mesh SiC | silicon carbide | 8.0-10.0 |
| CELITE 560 | diatomaceous silica | 95.7 |
| CELITE 545 | diatomaceous silica | 46.5 |
| CELITE 503 | diatomaceous silica | 33.9 |
| CELITE 512 | diatomaceous silica | 23.9 |
| CELITE 577 | diatomaceous silica | 20.8 |
| CELITE S | diatomaceous silica | 7.3 |
| glass microsphere | soda lime glass | 10-22 |
| glass microsphere | soda lime glass | 22-27 |
| glass microsphere | soda lime glass | 27-32 |
| glass microsphere | soda lime glass | 32-38 |
| glass microsphere | soda lime glass | 38-45 |
| glass microsphere | soda lime glass | 45-53 |
| glass microsphere | soda lime glass | 53-63 |
| 240 mesh $AlO_3$ | aluminum oxide | >37 |
| 280 mesh $AlO_3$ | aluminum oxide | 33-36 |
| 320 mesh $AlO_3$ | aluminum oxide | <37 |
| 360 mesh $AlO_3$ | aluminum oxide | 20.1-23.1 |
| 400 mesh $AlO_3$ | aluminum oxide | 15.5-17.5 |
| 500 mesh $AlO_3$ | aluminum oxide | 11.3-13.3 |
| 600 mesh $AlO_3$ | aluminum oxide | 8.0-10.0 |
| 800 mesh $AlO_3$ | aluminum oxide | 5.3-.73 |

Blunt-ended dsRNA triggers targeting GFP or magnesium chelatase were diluted to 5 milligrams/milliliter in 200 millimolar mannitol containing 0.05% Silwet L77. Fifteen microliters of RNA solution was hand applied using a pipette onto two leaves of transgenic *Nicotiana benthaminiana* 16c plants and allowed to dry briefly. Dry uncoated particles were sprayed in three 1-second bursts onto the RNA-coated leaves at 60 psi using a G78 airbrush mounted to a ring stand at 7 centimeters nozzle-to-leaf distance from the plants. GFP silencing was assessed visually using blue light excitation at 7 days after treatment. The results comparing visual silencing efficacy for the different particulates is depicted in FIG. 2. Under the conditions in this experiment, the greatest silencing with lowest leaf damage generally resulted from use of particles of about 10 to about 25 micrometers in size. The use of larger particles also resulted in GFP silencing but also caused heavier leaf damage. The use of smaller particles resulted in less silencing and less leaf damage. Particulate shape (angular or round) had little effect on silencing efficiency. Density appeared to be an important factor as little silencing was observed with diatomaceous silica, the least dense particle tested.

Example 32. Comparison of the Silencing Efficiency of Single-Step and Two-Step Application Methods This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as an RNA "trigger" or silencing element into a plant.

This experiment compared the silencing efficiency of a single-step application of RNA-coated particulates and a two-step sequential application. The GFP silencing efficacy of a 124 bp dsRNA trigger and of a 22 bp dsRNA trigger was also compared.

In the single-step method, the dsRNA trigger was diluted in water and added to 200 milligrams SiC (400 mesh), air dried overnight with gentle agitation, ground gently and sieved through 270 mesh. Thirty microliters of an aqueous solution of 0.05% Silwet L77, 200 millimolar mannitol was applied by hand to the top two expanded leaves and terminal leaf of transgenic *Nicotiana benthaminiana* 16c plants; the dry dsRNA-coated particles were sprayed in three 1-second bursts onto the Silwet L77/mannitol-coated leaves at 60 psi using a G78 airbrush mounted to a ring stand at 7 centimeters nozzle-to-leaf distance from the plants. To estimate the amount of dsRNA delivered, three 1-second bursts of the dry dsRNA-coated particles were sprayed into 100 microliters of water in a centrifuge tube which was then vortexed, and the dsRNA concentration estimated by UV spectrometry.

In the two-step method, the dsRNA trigger was diluted in water. Silwet L77 and mannitol was added to the dsRNA solution to final concentrations of 0.05% and 200 millimolar, respectively. Thirty microliters of the dsRNA solution was applied by hand to the top two expanded leaves and terminal leaf of transgenic *Nicotiana benthaminiana* 16c plants; the treated leaves were allowed to air dry 10 minutes. SiC (400 mesh) particles were sprayed in three 1-second bursts onto the Silwet L77/mannitol-coated leaves at 60 psi using a G78 airbrush mounted to a ring stand at 7 centimeters nozzle-to-leaf distance from the plants.

GFP silencing was assessed visually using blue light excitation at 7 days after treatment. In this experiment, GFP silencing efficiency for the single-step and two-step application methods appeared to be similar, and, while on a mass basis the 22 bp dsRNA trigger was more efficient than the 124 bp dsRNA trigger, the efficiency was similar when compared on a mole basis.

Example 33. Comparison of the Silencing Efficiency of Various Single-Step and Two-Step Application Methods This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as an RNA "trigger" or silencing element into a plant.

This experiment compared the silencing efficiency of a single-step application of RNA-coated particulates, a two-step sequential application, a single-step high-pressure spray application of RNA without particulates, and a single-step high-pressure spray application of an RNA/particulate suspension. A commercial spray tip fitted in a track sprayer was used.

Blunt-ended dsRNA triggers targeting GFP or magnesium chelatase were diluted to 5 milligrams/milliliter in 200 millimolar mannitol containing 0.05% Silwet L77. For the RNA/particulate suspensions, diatomaceous silica (Celite 512) or SiC (360 mesh) was added to the above RNA solutions at 20 milligrams/milliliter. The RNA preparations were sprayed onto transgenic *Nicotiana benthaminiana* 16c plants at either 60 or 85 psi using a canister sprayer fitted with a TeeJet 40005E flat fan nozzle positioned 7 centimeters from the plants. The plants sprayed at 60 psi were sprayed a second time with dry uncoated particles applied at 80 psi with a canister sprayer fitted with a TeeJet DG110015 nozzle 10 centimeters from the plants. GFP silencing was assessed visually using blue light excitation at 7 days after treatment. Silencing efficiency was very low in the plants sprayed only with RNA solutions (no particulates). Silencing using either the RNA/Celite or RNA/SiC suspensions was observed for both GFP and magnesium chelatase; for GFP the silencing efficacy was less than that resulting from a two-step sequential application, but for magnesium chelatase the silencing efficacy was comparable. These results indicate that a single-step application of an RNA/particulate suspension is efficacious and can be advantageously used with commercial spraying equipment.

Example 34. Systemic Silencing of a Target Gene by Particulate-Assisted Delivery of a Nucleic Acid into Maize This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of an RNA "trigger" into maize plants.

This experiment demonstrates silencing of a GFP transgene in maize (*Zea mays*). A 121 bp dsRNA targeting GFP was diluted to 5 milligrams/milliliter in water containing 0.05% Silwet L77. Thirty microliters of the RNA solution was applied to a single corn (*Zea mays*) leaf and allowed to dry briefly. Dry uncoated silicon carbide particles (280, 320, 360, and 400 mesh) were sprayed at 60 psi on the dsRNA-coated leaves using a G78 airbrush mounted to a ring stand 5 centimeters from the plants. GFP silencing was assessed visually using blue light excitation at 7 days after treatment. GFP silencing was observed in plants sprayed with 280, 320, and 360 mesh SiC. The silenced sectors manifested as a long stripe (in one plant treated with 360 mesh SiC) or multiple small spots (in two plants treated respectively with 280 and 320 mesh SiC). Silenced and non-silenced sectors were sampled in the leaves and GFP expression was measured. GFP expression was reduced by about 30 to about 50 percent in silenced sectors compared to non-silenced sectors was observed in both silenced sector types (stripe and spots).

Example 35. Particulate-Assisted Delivery of a Nucleic Acid Using Cotton Swabs as Matrix to Support an Abrasive This example illustrates non-limiting embodiments of methods, apparatuses, and compositions useful for delivering a nucleic acid into a plant or cells or tissues of a plant. More specifically, this example describes systemic silencing of a target gene by various methods including contacting a plant surface with a matrix supporting an abrasive. In these experiments, cotton swabs supporting a particulate abrasive, uncoated or coated with dsRNA trigger, are used to abrade a plant surface and deliver a dsRNA trigger to the plant.

In a first experiment, dry dsRNA-coated particles were prepared by mixing 100 milligrams of silicon carbide (360 mesh) particles per 1 milliliter of formulations containing 1.5 milligrams/milliliter 78 bp dsRNA against GFP in: a) water, b) 4 millimolar MES buffer, c) 200 millimolar mannitol, or, d) 4 millimolar MES buffer and 200 millimolar mannitol. The dsRNA-SiC mixtures were air dried overnight on a rotational shaker. A cotton swab was loaded with the dry, dsRNA-coated SiC particles by pressing the swab into the prepared SiC particles, and then used to gently abrade the upper leaf surface of approximately 4-week old transgenic *Nicotiana benthaminiana* 16c plants by gently rolling the swab along the leaf surface with the leaf supported from below by the worker's finger. GFP silencing was assessed visually using blue light excitation at 7 days after treatment. In this experiment, addition of 200 millimolar mannitol to the dsRNA formulation prevented leaf dehydration after abrasion using cotton-swab rolling with dsRNA coated SiC particles. Addition of 4 millimolar MES and 200 millimolar mannitol to the dsRNA formulation enhanced frequency of GFP silencing foci in the treated leaves.

In a second experiment, dry dsRNA-coated SiC particles were manufactured by prepared by mixing 100 milligrams of silicon carbide (360 mesh) particles per 1 milliliter of an aqueous dsRNA solution at the following trigger concentrations: a) 1.5 milligrams/milliliter of a 78 bp dsRNA trigger against GFP, b) 1.5 milligrams/milliliter of a 76 bp dsRNA trigger against the *N. benthamiana* 16C magnesium chelatase, and c) a mix of both triggers at 0.75 milligrams/milliliter each. The dsRNA-SiC mixtures were air dried overnight on a rotational shaker. A cotton swab was loaded with the dry, dsRNA-coated SiC particles by pressing the swab into the prepared SiC particles, and then used to gently abrade the upper leaf surface of approximately 4-week old transgenic *Nicotiana benthaminiana* 16c plants by gently rolling the swab along the leaf surface with the leaf supported from below by the worker's finger. The same dry, dsRNA-coated SiC particle preparations were delivered to a second set of plants using an airbrush. Silencing was assessed visually using ambient light or blue light excitation at 7 days after treatment. In this experiment, GFP and magnesium chelatase silencing foci were observed in treated leaves with all particle coating protocols and delivery methods. The expected gene-target-specific phenotypes were observed in plants treated with a single dsRNA trigger, and phenotype co-localization was observed in plants treated with both dsRNA triggers.

In a third experiment, efficacy of three different two-step sequential delivery methods using the cotton-swab rolling technique was tested in *N. benthamiana* 16C seedlings. In these methods, the dsRNA trigger is applied to the plant surface prior to abrasion of the plant surface with uncoated particulates supported on a cotton swab.

The two-step sequential delivery methods tested were:

(a) Method 1: the dsRNA formulation was pipetted onto the leaf surface and spread with a pipette tip to ensure uniform coverage, followed by abrasion by rolling a cotton-swab carrying uncoated SiC particles;

(b) Method 2: leaves were abraded by rolling a cotton-swab carrying uncoated SiC particles, followed by pipette delivery and spreading of the dsRNA formulation; and (c) Method 3: the cotton swab was first submerged in the dsRNA formulation, and then rolled over uncoated SiC particles, and finally gently rolled on the leaf surface.

Three liquid formulations of a 78 bp dsRNA trigger against GFP were tested: 2 milligrams/milliliter dsRNA in water; 2 milligrams/milliliter dsRNA in 200 millimolar mannitol and 20 millimolar MES; and 0.0125 milligrams/milliliter dsRNA in a Lipofectamine® formulation. For each treatment, a total of 20 microliters dsRNA formulation was applied per treated leaf of approximately 4-week old transgenic *Nicotiana benthaminiana* 16c plants (three plants per treatment). Silencing was assessed visually using blue light excitation at 4 and 7 days after treatment. In this experiment, all three delivery methods and all dsRNA formulations produced GFP silencing foci in treated leaves. Plants treated by Method 1 maintained normal leaf growth and displayed a higher frequency of GFP silencing foci per treated leaf. The frequency of GFP silencing foci was significantly greater in plants treated with a dsRNA concentration of 2 milligrams/milliliter, compared to plants treated with dsRNA of 0.0125 milligrams/milliliter in the Lipofectamine® formulation. Addition of 200 millimolar mannitol and 20 millimolar MES increased frequency of GFP silencing foci across delivery treatment types.

Example 36. Particulate-Assisted Delivery of a Nucleic Acid Using Sandpaper

This example illustrates non-limiting embodiments of methods, apparatuses, and compositions useful for delivering a nucleic acid into a plant or cells or tissues of a plant. More specifically, this example describes systemic silencing of a target gene by various methods including contacting a plant surface with a matrix supporting an abrasive. In these examples, sandpaper serves as a matrix supporting a particulate abrasive, and is used to abrade a plant surface and deliver a dsRNA trigger to the plant.

Sandpapers for wet sanding were used to deliver a 78 bp dsRNA trigger against GFP into approximately 3-week old transgenic *Nicotiana* benthaminiana 16c plants. Three different grit sizes were used: P180, P600, and P2500, which have an average particle size diameter of 82, 25.8, and 8.4 micrometers, respectively. The sandpaper was supported by a ¾-inch diameter PVC tube to facilitate gentle rolling on the surface of the treated leaves. Formulations of the dsRNA at a final concentration of 2 milligrams/milliliter were prepared in water or in aqueous 0.05% Silwet L77. Ten or 20 microliters of dsRNA formulation were pipetted onto the surface of two leaves per plant, and spread with a pipette tip to ensure uniform coverage, followed by abrasion by gently rolling the sandpaper over the treated leaf surface. For comparison, additional plants were treated only with the dsRNA formulation (no abrasion), or with the dsRNA formulation followed by abrasion with a cotton swab supporting SiC particles (360 mesh). Silencing was assessed visually using blue light excitation at 4 and 7 days after treatment.

The results are summarized as follows. No signs of leaf damage or turgor loss was observed in treated *Nicotiana benthaminiana* leaves. Treated plants showed no signs of wilting or severe leaf damage immediately after treatment or 1 day after treatment. The observed frequency of GFP silencing foci depended on sandpaper grit size; plants abraded with the 600 sandpaper roller had greater frequency of GFP silencing foci than plants abraded with other sandpaper grit sizes with the cotton swab supporting uncoated SiC particles. In a two-step sequential application (dsRNA applied first, followed by abrasion), abrasion with sandpaper was found to be more efficient in inducing GFP silencing foci than abrasion with a cotton swab supporting uncoated SiC particles, independently of the dsRNA formulation or timing of abrasive treatment.

Results from these and similar experiments provided further inferences. Silencing activity was observed to be retained in plants where the dsRNA-treated leaf was left for a day prior to abrasion; a stronger phenotype and more frequent GFP silencing foci were observed when the dsRNA formulation was left to dry on the surface of the leaf for at least 20 minutes prior to abrasion. Experiments with a "flat" roller, which gave reduced silencing efficacy, suggested that leaf surface abrasion and not pressure alone is the mechanism for dsRNA delivery. Sequential abrasive methods have shown consistently high efficacy levels and success rate. Systemic GFP silencing was observed in sandpaper-abraded *N. benthamiana* 16C plants grown under different conditions and in different locations, approximately 10-13 days after treatment, independent of the dsRNA trigger size used. Efficacy of mechanical abrasion methods was also demonstrated against endogenous gene targets including magnesium chelatase, PAT1, and PDS.

Similar experiments demonstrating localized target gene silencing induced by particle-assisted nucleic acid delivery were carried out in *Arabidopsis thaliana*. The sandpaper abrasion method was modified for developing *Arabidopsis thaliana* leaves from small plants grown in 24-well blocks. Round-tip tweezers were modified by wrapping one end with a paper pad and laboratory film (Parafilm M® Bemis NA, Neenah, Wis.) (to support the leaf and prevent leaf damage), and attaching sandpaper to the other end with double-sided sticky tape. Similarly, methods using a cotton-swab rolling technique for abrasion can also be used on *Arabidopsis thaliana* seedlings.

Similar experiments were also carried out in a transgenic tomato line expressing GFP. GFP and magnesium chelatase silencing foci were observed in tomato seedlings treated with a two-step sequential method including dsRNA application followed by sandpaper abrasion. The frequency of putative GFP silencing foci was low (1-2 foci per treated leaves) but was present in 6 to 7 of 10 treated tomato seedlings. Magnesium chelatase silencing foci was observed with low frequency in treated tomato seedlings, tomato seedlings treated with mixed dsRNA triggers displayed the expected co-localized GFP and magnesium chelatase silencing foci.

Example 37. Delivery of dsRNA Triggers by Sandpaper Abrasion

This example illustrates non-limiting embodiments of methods, apparatuses, and compositions useful for delivering a nucleic acid into a plant or cells or tissues of a plant. More specifically, this example describes systemic silencing of a target gene by applying a relatively small (22 base-pair) dsRNA trigger to a plant surface, followed by abrasion with a matrix supporting particulate abrasives.

This example describes systemic silencing of GFP in transgenic *Nicotiana benthaminiana* 16c plants by a 22 bp dsRNA trigger in combination with sandpaper abrasion. Non-specific dsRNA was used as a control in the experiment. The dsRNA was dissolved in water to 1 milligram/milliliter final concentration and a total of 20 microliters dsRNA was applied to 2 young leaves on individual transgenic *Nicotiana benthaminiana* 16c plants. The treated leaves were abraded with a 600 sandpaper roller. Samples for Northern blot analysis of GFP mRNA levels were collected at 24 and 48 hours after treatment. Silencing was assessed visually using blue light excitation at 2, 5, 8, and 13 days after treatment. A reduction of GFP mRNA expression in the dsRNA-treated plants was observed at 1 day after treatment, and strong GFP expression reduction observed at 2 days after treatment. Localized GFP silencing was observed on treated leaves at 2 days after treatment, and the localized silencing phenotype became much clearer and stronger from 5 days after treatment onward. Systemic GFP silencing was observed on untreated young leaves at 10 to 13 days after treatment.

In a similar experiment, 22 bp dsRNA trigger targeting an endogenous gene, magnesium chelatase, was used. The dsRNA was dissolved in water to 1 milligram/milliliter final concentration and a total of 20 microliters dsRNA was applied to 2 young leaves on individual transgenic Nicotiana benthaminiana 16c plants. The treated leaves were abraded with a 600 sandpaper roller. Silencing was assessed visually under visible light at 2, 5, 8, and 13 days after treatment. Localized silencing was observed as the expected chlorophyll-deficient phenotype in leaves treated with the dsRNA.

Example 38. Delivery of dsRNA Triggers by Abrasion

This example illustrates non-limiting embodiments of methods, apparatuses, and compositions useful for delivering a nucleic acid into a plant or cells or tissues of a plant. More specifically, this example describes systemic silencing of a target gene by treatment with a dsRNA targeting the promoter region of the target gene, followed by abrasion with a matrix supporting particulate abrasives.

The region upstream of the transgenic GFP insert from Nicotiana benthaminiana 16c was cloned and sequenced. The size of the sequenced region is 2278 bp and contains an 835 bp region encoding the cauliflower mosaic virus (CaMV) 35S promoter. An upstream expression cassette containing a nos terminator is located 698 bp from the 5' end of the CaMV 35S promoter. Three dsRNA triggers, ranging in size from 122-127 bp, were designed to match the DNA sequence from 3' end of the CaMV 35S promoter region: CaMV.35S-1, CaMV.35S-2, CaMV.35S-3, and (as a control) a 124 bp dsRNA targeting the coding region of GFP. The dsRNA was dissolved in water to 4 milligram/milliliter final concentration and a total of 10-20 microliters dsRNA was applied to leaves 3 and 4 from 2 week-old plants transgenic Nicotiana benthaminiana 16c plants. After the RNA was aliquoted on the leaves, a pipette tip was used to evenly spread the RNA over the surface of the adaxial side of each leaf. The RNA solution was allowed to dry for 30 minutes and then the top of the leaf was abraded once with P600 sandpaper glued to a dowel that was rolled over the leaf. The plants were then placed in a growth chamber set for 263 micromoles of light set for 14 hour/10 hour (light/dark cycle) with a temperature setting of 23 degrees Celsius/18 degrees Celsius (day/night). Silencing was assessed visually using blue light excitation at 7 days after treatment. The first 2 triggers closest to the end of the promoter, CaMV.35S-1 and CaMV.35S-2, produced a strong silencing phenotype with many small silencing foci on the treated leaves. CaMV.35S-3 produced the weakest phenotype with only slight levels of silencing in only a few areas. The control dsRNA targeting the coding region of GFP gave the strongest phenotype with many large silencing spots that merge to cover most of the treated leaves.

Example 39. Delivery of RNA Triggers by Different Abrasives

This example illustrates non-limiting embodiments of methods, apparatuses, and compositions useful for delivering a nucleic acid into a plant or cells or tissues of a plant. More specifically, this example describes systemic silencing of a target gene by treatment with a nucleic acid, followed by abrasion with a particulate that disrupts cells in the cuticle or epidermis or both cuticle and epidermis of the plant.

Double-stranded RNA was fluorescently labelled with Cy3 and coated onto SiC particles (320 mesh) or soda lime glass beads of three size ranges (10-22, 22-27, and 35-45 micrometer). Control particles were made in the same way but without Cy3 labelling. The dry dsRNA-coated SiC or glass beads were sprayed onto leaves and central axis of 3-week old Nicotiana benthaminiana 16c plants at 65 psi using a G78 airbrush mounted to a ring stand at 5-7 centimeters nozzle-to-leaf distance from the plants. Equipment was cleaned with ethanol between treatments to minimize cross-contamination.

For live imaging studies regions of interest (silenced spots identified as red areas under UV light) were removed with 4-5 millimeter biopsy punches and the live tissues were imaged with confocal fluorescence microscopy. In addition, tissue samples were fixed with paraformaldehyde, cryoprotected with sucrose, mounted in OCT medium, and cryosectioned for epifluorescent and bright-field imaging. These microscopic studies demonstrated that the sprayed particles primarily impacted epidermal cells.

Similar microscopic studies were performed on tomato leaves treated with a two-step sequential method including dsRNA application followed by abrasion with sandpapers of different grit sizes. The results demonstrated that silencing efficiency increased in the grit size order P200<P400<P2000 (i.e., from coarser to finer grits), indicating that the most efficacious sandpapers have grit sizes that can disrupt the leaf cuticle and only compromise or partially compromise the epidermal cell layer but do not cause deeper damage.

Example 40. Comparison of the Silencing Efficiency of Sandpapers of Different Grit Sizes and the Use of RNase Inhibitor This example illustrates non-limiting embodiments of methods, apparatuses, and compositions useful for delivering a nucleic acid into a plant or cells or tissues of a plant. More specifically, this example describes systemic silencing of a target gene by treatment with a dsRNA, followed by abrasion with a matrix supporting particulate abrasives.

This experiment compared the silencing efficiency of sandpapers of different grit sizes in a two-step sequential application. The effects of nuclease inhibitors were also examined.

Three dsRNA formulations were prepared. The base formulation contained 124 bp dsRNA trigger at 2 milligram/milliliter, 200 millimolar mannose, 4 millimolar MES buffer final concentration in water. A second formulation was identical to the base formulation but included 4.8 millimolar $Zn_2SO_4$ as an RNase inhibitor. A third formulation was identical to the base formulation but included 3.7% RNasin® Ribonuclease Inhibitor (Promega Corporation, Madison, Wis.) as an RNase inhibitor. A total of 10 or 20 microliters dsRNA was applied to two leaves of 3-week old plants transgenic Nicotiana benthaminiana 16c plants. After the RNA was aliquoted on the leaves, a pipette tip was used to evenly spread the RNA over the surface of the adaxial side of each leaf. The RNA solution was allowed to dry for 30 minutes and then the top of the leaf was abraded once with sandpaper of two different grit sizes (P180 or P600) attached to a ¾-inch PVC tube that was rolled over the leaf. Silencing was assessed visually using blue light excitation at 7 days after treatment. Results are provided in Table 35.

TABLE 35

| Sandpaper grit | RNase inhibitor | Average number of GFP silencing loci per leaf | Standard error |
|---|---|---|---|
| P600 | None | 50 | 15 |
| P600 | Zn$_2$SO$_4$ | 78 | 13 |
| P600 | RNasin ® | 66 | 12 |
| P180 | None | 4 | 2 |
| P180 | Zn$_2$SO$_4$ | 9 | 3 |
| P180 | RNasin ® | 6 | 2 |

These results show that across all formulations, P600 abraded leaves had ~10× more GFP silencing foci per leaf than those abraded with a coarser P180 sandpaper. Independently of the sandpaper grit used, formulations including an RNase inhibitor had more GFP silencing foci per leaf. The effect of nuclease inhibitor on increasing number of GFP silencing foci per leaf was relatively stronger for the coarser P180 sandpaper abraded leaves than for the P600 abraded leaves. At the concentrations used, Zn$_2$SO$_4$ had the strongest effect on increasing the number of GFP silencing foci per leaf.

Example 41. Delivery of dsRNA Triggers in Preventing Systemic Infection of a Virus This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as DNA viral vector into a plant. This example demonstrates the effect of directly applied dsRNA triggers in preventing systemic infection of TSWV.

An experiment was conducted to assess the capacity of dsRNA triggers applied without bacterial lysate to prevent infection with tomato spotted wilt virus (TSWV) in *Nicotiana benthamiana*. GFP silencing served as a tracer for trigger delivery and processing. Two 298 bp chimeric dsRNA triggers were produced; the first trigger TSWV-GFP-TSWV included two dsRNA regions targeting GFP flanking a dsRNA region targeting the TSWV N-gene, and the second trigger GFP-TSWV-GFP included two dsRNA regions targeting the TSWV N-gene flanking a dsRNA region targeting GFP. The blunt-ended 141 bp dsRNA trigger targeting GFP was used as a control.

The chimeric and control dsRNA triggers were applied directly to *N. benthamiana* 16c plants showing 3 true leaves (approximately 26 days after germination), followed by abrasion with 600 grit sandpaper. Local silencing of GFP was observed on the treated leaves in all treatments 4 days after treatment; at this time, TSWV was rub-inoculated onto the leaves showing local GFP silencing. Fourteen days after TSWV challenge, plants were assessed for development of TSWV symptoms. All plants treated with the GFP trigger alone were strongly symptomatic for TSWV. Less than 20% of plants treated with the chimeric GFP/TSWV dsRNA triggers were obviously infected with TSWV. Similar results occurred in a similar experiment where plants were inoculated with TSWV 7 days after treatment, demonstrating that direct application of the chimeric dsRNA triggers protected plants from TSWV infection for at least 7 days after treatment.

Example 42. Delivery of dsRNA Triggers Targeting Non-Coding Regulatory Regions of a Gene This example illustrates non-limiting embodiments of methods, apparatuses, and compositions useful for delivering a nucleic acid into a plant or cells or tissues of a plant. More specifically, this example describes systemic silencing of a target gene using a dsRNA trigger targeting a non-coding regulatory region of the gene to be silenced, and heritability of the phenotype in a progeny plant.

The sequence of the promoter region of the chalcone synthase chs (A) gene in *Petunia hybrida* was published by Van der Meer et al. (1990) Plant Mol. Biol., 15:95-190. A 258 bp blunt-ended dsRNA trigger targeting the upstream promoter region was produced. The dsRNA trigger is applied to *Petunia hybrida* leaves with abrasion, using any of the single-step or two-step methods described in the preceding working Examples. The treated leaves are regenerated into R0 plants. R0 plants displaying the expected phenotype of white flowers are selected. The white flower phenotype is heritable by an epigenetic effect in plants of the subsequent generation.

Example 43. Delivery of Nucleic Acids for In Vivo Editing of a Plant Gene

This example illustrates non-limiting embodiments of methods, apparatuses, and compositions useful for delivering a nucleic acid into a plant or cells or tissues of a plant. More specifically, this example describes use of a method including application of nucleic acids to the surface of a plant, followed by abrasion with a particulate, whereby the nucleic acids are delivered to the plant and result in in vivo editing or sequence replacement of a gene in the plant.

Methods for in vivo editing or sequence replacement of a gene are known in the art, for example through the use of zinc-finger nucleases, CRISPR, and Cas9. See, for example, Townsend et al. (2009) Nature, 459:442-446; Qi et al. (2012) Nature Biotechnol., 30:1002-1007; Cong et al. (2013) Science, 339:819-823; and Hsu et al. (2013) Nature Biotechnol., 31:827-834. In this example, nucleic acids for in vivo editing are used with methods similar to those described herein in the preceding Examples to modify the sequences of an endogenous gene in a plant.

Specific amino acid point mutations of the endogenous acetolactate synthase genes (ALS SuRA and SuRB) in tobacco (*Nicotiana tabacum*), which share highly conserved coding regions, result in resistance to certain herbicides. Three such amino acid point mutations are P191A (conferring resistance to chlorsulphuron), W568 L (conferring resistance to both chlorsulphuron and imazaquin), and S647T (conferring resistance to imazaquin), for which the corresponding nucleotide mutations have been reported (depicted in FIG. 1b of Townsend et al. (2009) Nature, 459: 442-446).

Three nucleic acids are prepared: (1) a CAS9 expression DNA plasmid; (2) a synthetic ssRNA containing a fused target sequence/guide RNA, wherein the target RNA includes about 20 nucleotides of the selected region to be edited in vivo, fused to a guide RNA; and (3) a donor DNA (provided as either a plasmid or as a dsDNA fragment) including a replacement sequence selected from P191A, W568 L, and S647T, plus additional 5' and 3' flanking sequence as needed. The three nucleic acids are applied to *Nicotiana tabacum* leaves with abrasion, using any of the single-step or two-step methods described in the preceding working Examples. Herbicide-resistant R0 tobacco plants are regenerated from treated leaves on selective media containing the appropriate herbicide.

What is claimed is:

1. A method for delivering a polynucleotide from the exterior surface of a plant or plant part into the interior of a plant cell, comprising
   a) applying onto the surface of the plant or plant part at least one agent that is able to disrupt at least one barrier of the plant or plant part, and
   b) applying onto the surface of the plant or plant part one or more polynucleotides,
   wherein the at least one agent comprises a lipase enzyme,
   wherein steps a) and b) are carried out concurrently or sequentially in any order, and
   wherein the method further comprises applying onto the surface of the plant or plant part one or more osmolytes selected from the group consisting of sorbitol, mannitol, D-proline, and L-proline.

2. The method of claim 1, wherein the method further comprises applying onto the surface of the plant or plant part one or more surfactants, and
   wherein the polynucleotides, the enzyme, the osmolytes, and the surfactants are applied concurrently, or sequentially in any order and grouped in any combination thereof.

3. The method of claim 1, wherein the polynucleotide is a non-transcribable polynucleotide.

4. The method of claim 3, wherein the polynucleotide is selected from the group consisting of single-stranded DNA, single-stranded RNA, double-stranded DNA, double-stranded RNA, and an RNA/DNA hybrid.

5. The method of claim 1, wherein the polynucleotide comprises a sequence that is identical to, or complementary to, 21 or more contiguous nucleotides of a target sequence or an RNA transcribed from the target sequence.

6. The method of claim 1, wherein the polynucleotide encodes a site-specific enzyme or one or more RNA components of an RNA-guided nuclease.

7. The method of claim 1, wherein the at least one agent further comprises one or more enzymes selected from the group consisting of cellulase, hemicellulase, pectinase, cutinase, and any combination thereof.

8. The method of claim 2, wherein the one or more surfactants are nonionic surfactants.

* * * * *